United States Patent [19]

Crowe et al.

[11] Patent Number: 5,876,961

[45] Date of Patent: Mar. 2, 1999

[54] PRODUCTION OF ANTIBODIES

[75] Inventors: James Scott Crowe; Alan Peter Lewis, both of Beckenham, England

[73] Assignee: Glaxo Wellcome Inc., Research Triangle Park, N.C.

[21] Appl. No.: 378,939

[22] Filed: Jan. 26, 1995

Related U.S. Application Data

[63] Continuation of Ser. No. 952,640, which is a continuation of PCT/GB92/01282 Jul. 14, 1992, abandoned.

[30] Foreign Application Priority Data

| Jul. 15, 1991 | [GB] | United Kingdom | 9115284 |
| Mar. 23, 1992 | [GB] | United Kingdom | 9206284 |
| Aug. 1, 1994 | [GB] | United Kingdom | 9116594 |

[51] Int. Cl.⁶ .............................. C12N 15/13; C12N 1/20; C12P 21/00
[52] U.S. Cl. .................. 435/69.1; 435/320.1; 435/172.1; 435/252.3; 435/240.1; 935/66; 935/22
[58] Field of Search .............................. 435/172.1, 23.52, 435/703, 69.1, 320.1, 252.3, 240.1; 935/22, 66

[56] References Cited

U.S. PATENT DOCUMENTS

| 4,296,024 | 10/1981 | McAleer et al. . |
| 4,997,764 | 3/1991 | Favers . |

FOREIGN PATENT DOCUMENTS

| 2035381 | 1/1991 | Canada . |
| 2035384 | 1/1991 | Canada . |
| 131878 | 1/1985 | European Pat. Off. . |
| 314161 | 5/1989 | European Pat. Off. . |
| 365997 | 5/1990 | European Pat. Off. . |
| 2113715 | 6/1986 | United Kingdom . |
| 8202060 | 6/1982 | WIPO . |
| 8701131 | 2/1987 | WIPO . |
| 8900607 | 1/1989 | WIPO . |
| 9104336 | 4/1991 | WIPO . |
| 9107492 | 5/1991 | WIPO . |
| 9100342 | 1/1992 | WIPO . |
| 9302108 | 2/1993 | WIPO . |

OTHER PUBLICATIONS

Gillies, S.D. et al. *Bio/Technology* 7: 799–804 (1989) "Expression of human anti–tetanus toxoid antibody in transfected murine myeloma cells".

Nakatani, T. et al. *Bio/Technology* 7: 805–810 (1989) "Functional expression of human monoclonal antibody genes directed against pseudomonal exotoxin A in mouse myeloma cells".

Page et al., *Bio/Technology* 9(1), Jan. 1991, pp. 64–68.

Boss et al., *Nucleic Acids Res.* 12(9), 1984, pp. 3791–3807.

"IDEC Uses Monkeys to Produce New–Human Antibodies," *Genetic Technology News* 12:5, May 1992, pp. 2–3.

Larrick et al., *Bio/Technology* 7:9, Sep. 1989, pp. 934–938.

Levy et al., *Gene* 54, 1987, pp. 167–173.

Ehrlich et al., 1990, 1:23, Human Antibod. Hybridomas, Potential . . . Fragments.

Hird et al., Genes & Cancer, 1990, pp. 183–189, Immunotherapy . . . Antibodies.

Osband et al., 1989 Immunol. Today, Problems . . . Immunotherapy.

Harris et al., 1993, Tibtech, 11:43, Therapeutic . . . Age.

*Primary Examiner*—Frank C. Eisenschenk
*Attorney, Agent, or Firm*—Nixon & Vanderhye PC

[57] ABSTRACT

This invention relates to the preparation of recombinant primate antibodies by DNA technology; Micro-RNA techniques for production of the same; recombinant non-human primate antibodies; formulations containing the same; the use of such antibodies in the prophylaxis and treatment of humans, and diagnostic uses of such antibodies.

14 Claims, 11 Drawing Sheets

FIG. 2A.

```
                                              -19
                                               M   D   W   T   W   R   F   L
         TCTAAAGAAGCCCCTGGGAGCACAGCTCATCACCATGGACTGGACCTGGAGGTTCCTC  58
                                               SIGNAL⇒

1                   5
    F   V   V   A   A   A   T   G   V   Q   S   Q   M   Q   V   V   Q   S   G   A
    TTTGTGGTGGCAGCAGCTACAGGTGTCCAGTCCCAGATGCAGGTGGTGCAGTCTGGGGCT  118
                                            FR1⇒

10              15              20              25
    E   V   K   K   P   G   S   S   V   T   V   S   C   K   A   S   G   G   T   F
    GAAGTAAAGAAGCCTGGGTCCTCGGTGACGGTCTCCTGCAAGGCATCTGGAGGCACCTTC  178

30  31  32  33  34  35          40              45
    S   N   Y   A   I   S   W   V   R   Q   A   P   G   Q   G   L   E   W   M   G
    AGCAACTATGCTATCAGCTGGGTGCGACAGGCCCCTGGACAAGGGCTTGAGTGGATGGGA  238
        CDR1⇒              FR2⇒

50  51  52  a  53  54  55  56  57  58  59  60  61  62  63  64  65
    G   I   I   P   L   F   G   T   P   T   Y   S   Q   N   F   Q   G   R   V   T
    GGGATCATCCCTCTTTTTGGTACACCAACCTACTCACAGAACTTCCAGGGCAGAGTCACG  298
    CDR2⇒                                                          FR3⇒

70              75              80      82  a   b   c  83          85
    I   T   A   D   K   S   T   S   T   A   H   M   E   L   T   S   L   R   S   E
    ATTACCGCGGACAAATCCACCAGCACAGCCCACATGGAGCTGACTAGCCTGAGATCTGAG  358

90                  95  96  97  98  99 100  a   b   c   d   e
    D   T   A   V   Y   Y   C   A   T   D   R   Y   R   Q   A   N   F   D   R   A
    GACACGGCCGTGTATTACTGTGCGACAGATCGCTACAGGCAGGCAAATTTTGACCGGGCC  418
                                        CDR3⇒ f   g   h   i   k 101 102         105             110             115
    R   V   G   W   F   D   P   W   G   Q   G   T   L   V   T   V   S   S   A   S
    CGGGTTGGCTGGTTCGACCCCTGGGGCCAGGGCACCCTGGTCACCGTCTCCTCAGCCTCC  478
                            FR4⇒                                      CH1⇒

120             125             130 133     135
    T   K   G   P   S   V   F   P   L   A   P   S   S   K   S   T   S   G   G   T
    ACCAAGGGCCCATCGGTCTTCCCCCTGGCACCCTCCTCCAAGAGCACCTCTGGGGGCACA  538

140             145             150         154 156     162
    A   A   L   G   C   L   V   K   D   Y   F   P   E   P   V   T   V   S   W   N
    GCGGCCCTGGGCTGCCTGGTCAAGGACTACTTCCCCGAACCGGTGACGGTGTCGTGGAAC  598

165         169 171         175                 180 182
    S   G   A   L   T   S   G   V   H   T   F   P   A   V   L   Q   S   S   G   L
    TCAGGCGCCCTGACCAGCGGCGTGCACACCTTCCCGGCTGTCCTACAGTCCTCAGGACTC  658

185             190             195                 200 203 205
    Y   S   L   S   S   V   V   T   V   P   S   S   S   L   G   T   Q   T   Y   I
    TACTCCCTCAGCAGCGTGGTGACCGTGCCCTCCAGCAGCTTGGGCACCCAGACCTACATC  718
```

FIG. 2B.

```
        210              215              220  222 225       228 232
    C  N  V  N  H  K  P  S  N  T  K  V  D  K  K  V  E  P  K  S
    TGCAACGTGAATCACAAGCCCAGCAACACCAAGGTGGACAAGAAAGTTGAGCCCAAATCT  778
                                                       HINGE→

235              240              245              250
    C  D  K  T  H  T  C  P  P  C  P  A  P  E  L  L  G  G  P  S
    TGTGACAAAACTCACACATGCCCACCGTGCCCAGCACCTGAACTCCTGGGGGGACCGTCA  838
                          C_H 2→

255              260              265              270
    V  F  L  F  P  P  K  P  K  D  T  L  M  I  S  R  T  P  E  V
    GTCTTCCTCTTCCCCCCAAAACCCAAGGACACCCTCATGATCTCCCGGACCCCTGAGGTC  898

275              280              285              290  292
    T  C  V  V  V  D  V  S  H  E  D  P  E  V  K  F  N  W  Y  V
    ACATGCGTGGTGGTGGACGTGAGCCACGAAGACCCTGAGGTCAAGTTCAACTGGTACGTG  958

295  299 300         305              310         314 317
    D  G  V  E  V  H  N  A  K  T  K  P  R  E  E  Q  Y  N  S  T
    GACGGCGTGGAGGTGCATAATGCCAAGACAAAGCCGCGGGAGGAGCAGTACAACAGCACG  1018

320              325              330              335
    Y  R  V  V  S  V  L  T  V  L  H  Q  D  W  L  N  G  K  E  Y
    TACCGTGTGGTCAGCGTCCTCACCGTCCTGCACCAGGACTGGCTGAATGGCAAGGAGTAC  1078

340              345              350         355  357
    K  C  K  V  S  N  K  A  L  P  A  P  I  E  K  T  I  S  K  A
    AAGTGCAAGGTCTCCAACAAAGCCCTCCCAGCCCCCATCGAGAAAACCATCTCCAAAGCC  1138

360  363 365              370              375    378  381
    K  G  Q  P  R  E  P  Q  V  Y  T  L  P  P  S  R  D  E  L  T
    AAAGGGCAGCCCCGAGAACCACAGGTGTACACCCTGCCCCCATCCCGGGATGAGCTGACC  1198
       C_H 3→

385              390              395         400  402
    K  N  Q  V  S  L  T  C  L  V  K  G  F  Y  P  S  D  I  A  V
    AAGAACCAGGTCAGCCTGACCTGCCTGGTCAAAGGCTTCTATCCCAGCGACATCGCCGTG  1258

405     408 410    414 415           420              425
    E  W  E  S  N  G  Q  P  E  N  N  Y  K  T  T  P  P  V  L  D
    GAGTGGGAGAGCAATGGGCAGCCGGAGAACAACTACAAGACCACGCCTCCCGTGCTGGAC  1318

430  433 435              440              445         450
    S  D  G  S  F  F  L  Y  S  K  L  T  V  D  K  S  R  W  Q  Q
    TCCGACGGCTCCTTCTTCCTCTACAGCAAGCTCACCGTGGACAAGAGCAGGTGGCAGCAG  1378

455              460              465              470
    G  N  V  F  S  C  S  V  M  H  E  A  L  H  N  H  Y  T  Q  K
    GGGAACGTCTTCTCATGCTCCGTGATGCATGAGGCTCTGCACAACCACTACACGCAGAAG  1438

475
    S  L  S  L  S  P  G  K  *
    AGCCTCTCCCTGTCTCCGGGTAAATGAGTGCGACGGCCGGCAAGCCCCCGCTCCCCGGGC  1498

TCTCGCGGTCGCACGAGGATGCTTGGCACGTACCCCGTGTACATACTTCCCGGGCGCCCA  1558

GCATGGAAATAAAGCACCCAGCGCTGCCCTGGGCCCCTGCGAAAAAAAAAAAAAAAAAA  1617
```

FIG. 3A.

```
                                              -19
                                               M   A   W   A   L   L   L   L   T
        CAAGAGGCAGCGCTCTCGGGACGTCTCCACCATGGCCTGGGCTCTGCTGCTCCTCACC  58
                                              SIGNAL⇒

1                 5               9  11
   L    L   T   Q   D   T   G   S   W   A   Q   S   A   L   T   Q   P   A   S   V
        CTCCTCACTCAGGACACAGGGTCCTGGGCCCAGTCTGCCCTGACTCAGCCTGCCTCCGTG  118
                        FR1⇒

15                  20           24  25  26  27   d   e   f  28
   S   G   S   P   G   Q   S   I   T   I   S   C   T   G   T   N   N   D   V   G
        TCTGGGTCTCCTGGACAGTCGATCACCATCTCCTGCACTGGAACCAACAATGATGTTGGG  178
                                              CDR1⇒

29  30  31  32  33  34  35                  40                  45
    S   Y   N   L   V   S   W   Y   Q   Q   H   P   G   K   A   P   K   I   M   I
        AGTTATAACCTTGTCTCCTGGTACCAGCAGCACCCAGGCAAAGCCCCCAAAATCATGATT  238
                 FR2⇒

50  51  52  53  54  55  56               60                  65
    Y   E   V   S   K   R   P   S   G   V   S   N   R   F   S   G   S   K   S   G
        TATGAGGTCAGTAAGCGGCCCTCAGGGGTTTCTAATCGCTTCTCTGGCTCCAAGTCTGGC  298
           CDR2⇒                         FR3⇒

70                  75                  80                  85
    N   T   A   S   L   T   I   S   G   L   Q   A   E   D   E   A   D   Y   Y   C
        AACACGGCCTCCCTGACAATCTCTGGGCTCCAGGCTGAGGACGAGGCTGATTATTACTGC  358

89  90  91  92  93  94  95   a  96  97              100                 106  a
    C   S   Y   A   G   S   Y   T   V   V   F   G   G   G   T   K   L   T   V   L
        TGCTCATATGCAGGTAGTTACACTGTGGTTTTCGGCGGAGGGACCAAACTGACCGTCCTA  418
        CDR3⇒                                 FR4⇒

107         110             115                 120                 125
    G   Q   P   K   A   A   P   S   V   T   L   F   P   P   S   S   E   E   L   Q
        GGTCAGCCCAAGGCTGCCCCCTCGGTCACTCTGTTCCCGCCCTCCTCTGAGGAGCTTCAA  478
         Cλ⇒

130                 135                 140                 145
    A   N   K   A   T   L   V   C   L   I   S   D   F   Y   P   G   A   V   T   V
        GCCAACAAGGCCACACTGGTGTGTCTCATAAGTGACTTCTACCCGGGAGCCGTGACAGTG  538

150                 155                 160                 165
    A   W   K   A   D   S   S   P   V   K   A   G   V   E   T   T   T   P   S   K
        GCCTGGAAGGCAGATAGCAGCCCCGTCAAGGCGGGAGTGGAGACCACCACACCCTCCAAA  598

168 170                 175                 180                 185
    Q   S   N   N   K   Y   A   A   S   S   Y   L   S   L   T   P   E   Q   W   K
        CAAAGCAACAACAAGTACGCGGCCAGCAGCTATCTGAGCCTGACGCCTGAGCAGTGGAAG  658

190                 195             200 203         205
    S   H   R   S   Y   S   C   Q   V   T   H   E   G   S   T   V   E   K   T   V
        TCCCACAGAAGCTACAGCTGCCAGGTCACGCATGAAGGGAGCACCGTGGAGAAGACAGTG  718
```

FIG. 3B.

```
     210            215
   A  P  T  E  C  S  *
GCCCCTACAGAATGTTCATAGGTTCTAAACCCTCACCCCCCCACGGGAGACTAGAGCTG  778

CAGGATCCCAGGGGAGGGGTCTCTCCTCCCACCCCAAGGCATCAAGCCCTTCTCCCTGCA  838

CTCAATAAACCCTCAATAAATATTCTCATTGTCAATCACAAAAAAAAAAAAAAAAAAAA  898

AAAA  902
```

FIG. 4A.

```
                                                       CDR1
                                                  ****************
                    10                    20      27 a b c
Human   GACATCCAGATGACCCAGTCTCCATCCTCCCTGTCTGCATCTGTAGGAGACAGAGTCACCATCACTTGCCGGGCAAGTCAG
CynoK1  -------T---C-----------------T--------------G----------------------C---A-------
CynoK2  -------T---C-----------------T--------------G----------------------C---A-------
CynoK4  -------T---C-----------------------T-A------------------------G----T---A---G---A
CynoK5  -------T---C---------------------CT-----C-C-TCAG--C-T------GTCG-C-T-----T-C----
CynoK9  -------T---C-----------------T----------------------G--------------C---A-------
CynoK12 -------T---C---------------------------------------------G----------C---T-------
CynoK14 -------T---C--------------------------------------T--TC----A----T--------G------
CynoK15 -------T---C-------------------------------------------------G---------T--------
CynoK18 -------T---C---------------------------------------------G-----------C----T------
CynoK20 -------T---C---------------------------------------------G-----------C----T------
Rabbit  -C-C---GT---------A--------G-------G-------G----C---------------AG----C---G-----
Mouse   ----TGT---------T-----A-T-T----TG---TGA-A-C-A-TA-G-AG---------T-G----ACT--CTC-G--AGCCTTTAT CDR2
        **************                              **************
        d e f      30                    40                    50
Human   AGCATTAGCAATTATTTAAATTGGTATCAACAGAAACCAGGGAAAGCCCCTAAGCTCCTGATCTATGCTGCATCCAGTTTG
CynoK1  -G--------------------G-----------G-----------------G-----------------T---------
CynoK2  -G--------C---------G---------------------------------------T-----TA----AA-------
CynoK4  -----C-------------------------------------------------ATT----------AGG---------
CynoK5  
CynoK9  -G-------------G--------G---G-------A----T---------------------C---C-T---T---AG-TT----ACCG-
CynoK12 GA--------A----GTC------G-------------------------------------C---AAG---
CynoK14 
CynoK15 -G---C------G-------------G-----------A---T-----G---------------------G---------
CynoK18 -G--------A------GCC----G---------CA-------------------------C-GC-T--C-------G---C---
CynoK20 -G--------A------GCC----G-------------------------------C-GC-T--C-------G---C---
Rabbit  -G--------A------GCC----G------------------GA-----A-C-T-T----A--G-------A---GG---
Mouse   -A----TA--GC-C---GGC----C---GA---------------------------------A--C-GG------ACCGA
TCAAGCAAACA-AAGTGC-C---C
```

CDR3

|  | | | | | | 90 | | | | | 95a | | | | | 100 | | | | | | | | | | |
|---|---|---|---|---|---|---|---|---|---|---|---|---|---|---|---|---|---|---|---|---|---|---|---|---|---|---|
| Human | T | Y | Y | C | Q | Q | S | Y | S | T | L | * | * | * | * | * | I | T | F | G | Q | G | T | R | L | E | I | K |
| CynoK1 | V | - | - | - | - | H | - | - | D | - | P | Y | - | - | - | - | - | - | - | - | - | - | K | K | V | - | - | R |
| CynoK2 | - | - | - | - | - | - | - | - | - | - | P | Y | - | - | - | - | - | - | - | G | - | - | K | K | V | - | - | R |
| CynoK4 | V | - | - | - | - | - | - | - | G | Y | P | L | - | - | - | - | - | - | - | G | - | - | K | K | V | - | - | R |
| CynoK5 | - | - | - | - | M | - | - | - | R | S | P | W | - | - | - | - | - | - | - | - | - | - | K | K | V | R | R | R |
| CynoK9 | - | - | - | - | L | - | - | - | G | - | P | Y | S | - | - | - | - | - | - | - | - | - | K | K | V | - | - | R |
| CynoK12 | D | - | - | - | - | T | - | K | T | H | P | R | - | - | - | - | - | - | - | - | - | - | K | K | V | - | - | R |
| CynoK14 | V | - | - | - | M | - | - | - | S | - | P | F | - | - | - | P | - | - | - | - | - | - | K | K | V | D | - | R |
| CynoK15 | - | - | - | - | E | - | - | Y | N | T | P | Y | S | - | - | - | - | - | - | G | - | - | K | K | V | - | - | R |
| CynoK18 | - | - | - | - | - | - | - | - | D | N | P | F | - | - | - | - | - | - | - | - | - | - | K | K | I | - | - | R |
| CynoK20 | - | - | - | - | - | - | - | Y | N | Y | P | R | S | - | - | - | - | - | - | G | - | - | K | K | V | - | - | R |
| Rabbit | - | - | - | - | L | - | - | S | S | D | T | L | - | - | - | A | - | - | - | - | - | - | E | E | - | - | L | C |
| Mouse | H | - | - | - | A | - | - | F | - | Y | P | L | - | - | - | - | - | - | - | A | - | - | - | K | - | - | L | R |

FIG. 6.

```
                 110                 120                 130
Human       ACTGTGGCTGCACCATCTGTCTTCATCTTCCCGCCATCTGATGAGCAGTTGAAATCTGGAACTGCCTCTGTTGTGTGCCTGCTGAATAAC
Cynomolgus  G--------------------------------------------G--T---G-----------------T-----------------
Rabbit      GA-CCAAT---G---TA------C---C--------A------C---T---C-A---A---A-T-A-CA-C----G--GCA-----A
Mouse       G---AT-------A----A-C-------------CAG------A------------A-C-----GG-----A--C-----T--CT-----C 140                 150                 160
Human       TTCTATCCCAGAGAGGCCAAAGTACAGTGGAAGGTGGATAACGCCCTCCAATCGGGTAACTCCCAGGAGAGTGTCACAGAGCAGGACAGC
Cynomolgus  --------------------------GC----A---------GGT------A---A---A------------------------------
Rabbit      ---CG------AT--CAT--CC--CACC----------G---AAA-----CA-A-CGG-AT-G--A-C----ACA----CC----AG-CC
Mouse       -------C----A---CAT----T---CA-------A-T---GG-AGTGAA-G-CAAAA-G-CAAAA-G-GT--T-A-C---TGG--T--T------

170                 180                 190
Human       AAGGACAGCACCTACAGCCTCAGCAGCACCCTGAGCGCTGAGCAAAGCAGACTACGAGAAACACAAAGTCTACGCCCTGCGAAGTCACCCAT
Cynomolgus  -----A----------------G-------------------------GCA-A----C----GT-----T---------T-----------
Rabbit      G-A---T-T------A-------------T---T-A----C-G---A-C-GC---GC--G---A------G--GGT-
Mouse       --A------------A-G---------C------T---C----G-AC--G--T--ACG----T--CAG----TA----T--G-C---T--C 200                 210
Human       CAGGGCCTGAGCTCGCCCCGTCACAAAGAGCTTCAACAGGGGAGAGTGTTAG
Cynomolgus  --------------------------C------------------------
Rabbit      --CAA-TC-G----AG-GA--GTCC---------T----T--C--------
Mouse       A--ACATCA-CT---A---A-TGTC-----------------AAT-------
```

FIG. 7.

```
                110                 120                 130                 140                 150
Human       T V A A P S V F I F P P S D E Q L K S G T A S V V C L L N N F Y P R E A K V Q W L V D N A
Cynomolgus  A - - - - - - - - - - - - E D - V - - - - V - - - - - - - - - - - - - - K - - - E
Rabbit      D P H - - - - - L L - - - A D - T T - T V T H - V A - - K - - N D - - I - T K I - D G
Mouse       A D - - - - - - S - - - - S - - T - T - - - I - - - F - - - - - - - - T - I - G S 160                 170                 180                 190
Human       L Q S G N S Q E S V T Q Q D S K D S T Y S L S S T L T L S K A D Y E K H K L Y A C E V T H
Cynomolgus  - K T D - - - - - - - E - - - - - - - - - - - - - - - - - S T - - - Q S - - - - - - -
Rabbit      H - Q S - H E - - - P - S - - - - N - - - - - N - T - T - - I Q - - N S - N V - - - V -
Mouse       E R Q N G V L - - - D - P E - - - - - - - - M - - - - T - D E - - - R - S V - - - A 200                 210
Human       Q G L S S P V T K S F N R G E C
Cynomolgus  - - - - - - - - - - - - - - - -
Rabbit      N S G - - A I V Q - - - - - D -
Mouse       K T S T - - I V - - - - - N - -
```

PRODUCTION OF ANTIBODIES

This is a continuation of application Ser. No. 07/952,640, filed Dec. 1, 1992 now abandoned, which is a continuation of PCT/GB92/01282, filed Jul. 14, 1992.

This invention concerns the production of recombinant primate antibodies by DNA technology, their expression in eukaryotic cell lines and the use of such antibodies in the therapeutic and prophylactic treatment of human beings.

Antibodies, or immunoglobulins, are proteinaceous bifunctional molecules. One region, which is highly variable between different antibodies, is responsible for binding to an antigen, for example, the many different infectious agents that the body may encounter, whilst the second, constant region is responsible for binding to the Fc receptors of cells and also activates complement, a complex system of proteins responsible for cell lysis. In this way, antibodies represent a vital component of the immune response of mammals in destroying foreign microorganisms and viruses.

Antibodies are divided into different classes on the basis of the structure of the constant region. In humans for example, five major structural classes can be identified immunoglobulin G or IgG, IgM, IgA, IgD and IgE. Each class is distinguished on the basis of its physical and biological characteristics which relate to the function of the immunoglobulin in the immune system. IgGs can be further divided into four subclasses: IgG1, IgG2, IgG3 and IgG4, based on differences in the heavy chain amino acid composition and in disulphide bridging (see below for explanation), giving rise to differences in biological behaviour. A description of the classes and subclasses is set out in "Essential Immunology" by Ivan Roitt, Blackwell Scientific Publications.

An antibody molecule is composed of two light chains and two heavy chains that are held together by interchain disulphide bonds. Each light chain is linked to a heavy chain by disulphide bonds and the two heavy chains are linked to each other by disulphide bonds. Each heavy chain has at one end a variable domain followed by a number of constant domains, and each light chain has a variable domain at one end and a constant domain at the other end. The light chain variable domain is aligned with the variable domain of the heavy chain. The light chain constant domain is aligned with the first constant domain of the heavy chain. The remaining constant domains of the heavy chains are aligned with each other. The constant domains in the light and heavy chains are not involved directly in binding the antibody to the antigen.

The variable domains of each pair of light and heavy chains form the antigen binding site. They have the same general structure with each domain comprising a framework of four regions, whose sequences are relatively conserved, connected by three complementarity determining regions (CDRs). The four framework regions largely adopt a beta-sheet conformation and the CDRs form loops connecting, and in some cases comprising part of, the beta-sheet structure. The CDRs are held in close proximity by the framework regions and, with the CDRs from the other domain, contribute to the formation of the antigen binding site.

The antibody chains are encoded by genes at three separate loci on different chromosomes. One locus encodes the heavy chain isotypes and there are separate loci for the κ and λ light chains, although a B-lymphocyte only transcribes from one of these light chain loci. The genes which encode antibody variable domains are generated during B-lymphocyte ontogeny by a process of recombination involving the joining of the V,D and J gene regions. A single B-lymphocyte will only use one heavy chain and one light chain recombined variable domain to ensure that it only has one antigen specificity. So only one allele of the heavy chain and one allele of the light chain are expressed by a single B-lymphocyte. This is known as allelic exclusion.

The exposure of an animal to an antigen by infection or immunisation, results in the production of different antibodies with different specificities and affinities. An antiserum obtained from the immunised animal will, therefore, be heterogeneous and contain a pool of antibodies produced by many different lymphocyte clones. Antibodies thus obtained are referred to as polyclonal antibodies and this polyclonal nature has been a major drawback in the use of antibodies in therapeutic applications and in diagnostic assays.

A major step forward occurred in 1975 when Kohler and Milstein (*Nature*, 1975, 256, 495–497) reported the successful fusion of spleen cells from mice immunized with an antigen with cells of a murine myeloma line. The resulting hybrid cells, termed hybridomas, have the properties of antibody production derived from spleen cells and of continuous growth derived from the myeloma cells. Each hybridoma synthesizes and secretes a single antibody to a particular determinant of the original antigen. To ensure that all cells in a culture are identical, i.e. that they contain the genetic information required for the synthesis of a unique antibody species, the hybridomas resulting from cell fusion are cloned and subcloned. In this way, the cloned hybridomas produce homogeneous antibodies of the original animal species from which the spleen cells were derived.

The ability to produce monoclonal antibodies has revolutionised the diagnosis of many diseases and provides the possibility of prevention and immunotherapy of numerous pathological disorders. Unfortunately, foreign antibodies namely antibodies of non-human species, such as a mouse or a rat, administered repeatedly to a human for vaccination or treatment, will be recognised by the individual's immune system and are likely to cause an undesirable anti-globulin response. This anti-antibody response is due to the foreign origin of the constant domains and the four framework regions. The result of this response is likely to be the neutralising of the therapeutic antibody, and the triggering of harmful anaphylactic or allergic reactions. Furthermore, non-human monoclonal antibodies do not fix human complement particularly well and are less likely to trigger non-specific mechanisms of cell clearance such as antibody—dependent cell—mediated cytotoxcity (ADCC), in view of the differences in effector function of the constant region of the antibody. Non-human monoclonals are therefore not as effective as human antibodies in clearing infected or diseased cells. And so, for a therapeutic antibody to be effective and to remain in the circulation without raising an anti-antibody response, it must be able to escape recognition by the recipient's immune system.

One solution to this problem is to form chimeric antibodies as described in Morrison et al (*P.N.A.S.*, 1984, 81, 6851–6855); and Neuberger et al (*Nature*, 1985, 314, 268–270), where the variable region of a foreign species derived from a hybridoma as described above, is grafted to the constant region of human antibody. However, in this situation the variable region remains foreign to the recipient; thus, it may be recognised and may still pose a significant immunogenicity problem. The humanisation of an antibody, as described in Jones et al (*Nature*, 1986, 321 522–525); and Riechmann et al (*Nature* 1988, 332, 323–327), in which the CDRs of a foreign antibody species are grafted onto a human antibody framework, does alleviate many of these problems. However, the CDR-grafting of antibodies is a complicated process and the resultant antibody may require further modification to maintain its binding affinity. It is therefore clear that to avoid recognition by the human immune system, the optimum form of antibody is a human antibody or an antibody which is substantially identical to a human antibody.

Anecdotal reports have suggested that apes (e.g. chimpanzees) and monkeys (e.g. cynomolgus, rhesus, aotus) which are commonly used as laboratory animals, have immune responses sufficiently close to those of humans to provide good models of infection. It has also been suggested that their antibodies may be sufficiently homologous to human antibodies to overcome some of the problems faced with, for example, rodent antibodies. There is no published evidence of this and few if any non-human primate cell lines are available for testing. The process of obtaining such antibodies is therefore exceedingly problemmatic. Cell lines have been produced from human lymphocytes but such lines have low stability, do not readily form hybrids which might be more stable, and usually produce low yields of antibodies when cultured in vitro. Primate cells may also harbour foreign infectious nucleic acid, for example, from a virus, which poses problems of cross-infection of the human to be treated. Lengthy purification and/or sterilisation procedures must be applied before the antibody produced therefrom is in an acceptable form for administration to humans.

European patent Publication No. 314161 discloses a process for the production of human immunoglobulin in a eukaryotic host cell. The host cell is transfected with operably linked first and second genes which code for human heavy chain variable and constant regions respectively. The host cell is also transfected with operably linked genes coding for variable and constant regions of a human light chain. This transfected cell is cultured and recombinant human immunoglobulins, having variable regions of the desired binding specificity, can be recovered from the cell culture. However, this process poses a number of problems: i) a large quantity of lymphocytes is required for recovery of sufficient genomic DNA to carry out the process. The specification discloses, the removal of $1-2 \times 10^8$ lymphocytes from which 121 $\mu$g of genomic DNA were retrieved; ii) all four alleles (two for the heavy chain and two for the light chain) are retrieved in the genomic DNA and require extensive sequencing and selection by cloning, expression and binding studies, to obtain the functional pairing of genes (one for heavy chain and one for the light chain) for further processing; iii) poor expression levels of antibody are achieved by culturing the host cells transfected by the described process. The specification discloses yields of 6.7–34.5 $\mu$g/ml which average out at 20 $\mu$g/ml, and using a construct including a cytomegalovirus (CMV) expression enhancer only 1 $\mu$g/ml.

International Publication WO91/04336 also discloses a process for the production of human monoclonals through the recovery of genomic DNA.

It is quite clear that this process suffers from the same disadvantages described above for EP314161.

The advent of PCR has allowed the generation of cDNA clones from mRNA derived from small numbers of cells. Although PCR remains a very powerful tool, the requirement for knowledge of the sequences of the 5' and 3' end of the target cDNA sequence hampers the use of this technique for the generation of cDNA clones from mRNA coding for proteins with varied sequences, especially secreted products with diverse leader sequences such as the human antibody family. Although many human H chain sequences have been reported [Kabat E. A. et al. Sequences of Proteins of Immunological Interest, 4th Ed, US Dept. of Health and Human Services, US Govt. Printing Service 1987], and the PCR primers are designed from the consensus sequences of these, not all human V regions will be amplified using these primers due to the 3' bases being incompatible to elongation by Taq polymerase.

The present invention therefore provides a new process involving conventional recombinant cDNA cloning technology to facilitate the rescue of complete human, heavy and light chain antibody genes and their expression in eukaryotic cells using high level eukaryotic expression vectors for the immortalisation of functional antibodies.

Furthermore, the inventors have been able to demonstrate that cDNA cloned from a non-human primate peripheral blood lymphocyte and the antibody chain produced therefrom, does in fact show sufficient homology to a human antibody chain sequence to provide potentially useful therapeutic agents. The invention therefore includes a process for the rescue of non-human primate heavy and light chain antibody genes and their expression as described above.

The invention therefore provides a process for the production of a recombinant primate antibody comprising:

(i) selecting a primate lymphocyte-derived cell line that is capable of expressing a desired antibody;

(ii) isolating RNA from the cell line and separating mRNA from the other RNAs so isolated;

(iii) synthesising cDNA from the mRNA and inserting the cDNA into a cloning vector;

(iv) transforming a host cell with the vector containing the cDNA to obtain a library;

(v) screening the library for cDNA encoding the antibody heavy and light chain genes;

(vi) inserting the cDNA encoding the genes into an expression vector;

(vii) transfecting a host cell with the expression vector containing the cDNA; and (viii) culturing the transfected host cell and isolating the desired antibody.

The term 'primate' is taken to mean prosimians (e.g. Lemurs), new world monkeys (e.g. aotus), old world monkeys (e.g. cynomolgus), apes (e.g. chimpanzees) and humans.

Reference to a primate lymphocyte-derived cell line, means a cell line derived from a single primate lymphocyte which will produce a single antibody. The cell line must be sufficiently stable to enable recovery of RNA and so is preferably stabilised or immortalised using conventional viral transformation and/or hybridoma technology (as described in Methods of Hybridoma Transformation, Bartal and Hirsaut (eds), Humana Press, Clifton, N.H. 1985). Such cell lines may be obtained from depositories such as the Amercian Type Culture Collection of Rockville Md., USA.

The cell line may be produced by removing lymphocytes, namely lymphoblastoid cells or, B-lymphocytes, from the peripheral blood lymph nodes or from the spleen for example from an individual (human or non-human primate) known to have recovered from or be in remission from a disease state; from an individual known to be infected with a pathogenic organism or suffering from cancer or an autoimmune disease but who does not manifest full disease symptoms; from an individual who has been vaccinated or innoculated with antigen and has mounted an antibody response; from healthy individuals followed by screening for useful antibody. Examples of disease states include an infection by a pathogenic organism (eg virus or bacteria), wherein removal of lymphocytes preferably takes place within two to three months post recovery or during the phase of high antibody titre, or an individual who has received vaccination against an antigen, for example, of a pathogenic organism, wherein removal of lymphocytes preferably takes place within two to three months post immunisation. Individuals in whom a pathogenic organism, such as a virus, can be detected but who do not progress to a full disease state, may also provide an extremely useful source of antibody-producing cells. Clearly, it is possible when using non-human primates to inoculate with a pathogenic organism rather than an attenuated form of the organism which is frequently the form used for vaccination of humans. The immune response to this organism may well be far greater, thus providing a better source of antibody-producing cells, than from the vaccinated individual.

A cell line may also be produced by removing lymphocytes from an individual who is known to be suffering from a disease state such as cancer or an autoimmune disease and can be demonstrated to be making an antibody response directed against either tumor cells or self antigens. Lymphocytes may also be obtained from an individual who is identified as showing spontaneous remission of his or her cancer or who has been vaccinated with tumor antigens, and has mounted an antibody response. An alternative approach for the identification of useful lymphocytes involves screening cohorts of individuals known to be at risk of developing cancer through exposure to certain environmental factors or through a genetic predisposition; for example, "cancer families" which display a greater than average occurance of cancer within the population. These cohorts may be screened, in particular, for individuals who do not develop cancer as a result of their ability to raise antibody to the tumor antigens. It may also be possible to screen healthy individuals for anti-tumor antibodies based on a theory that cancerous cells are present in all individuals, the immune system is generally able to mount a response, namely, by the production of antibodies, to remove the mutated cells before a cancerous state is reached. If this is so, useful lymphocytes may be obtainable from any individual. The lymphocytes so identified may then be stablised by viral transformation and/or fusion as described below.

Viral transformation is preferably carried out using Epstein Barr Virus (EBV). Most peripheral blood B-lymphocytes have a receptor for EBV and when infected by the virus these cells are transformed with the accompanying expression of the EBV nuclear antigen (EBNA). However, only around 20% of cells are "immortalised" in vitro and these are in general only small non-activated B cells. Plasma cells (activated B-cells) lack the EBV receptor so resistance to EBV infection appears to increase with maturity reducing the effectivity of viral transformation by this route when the recovered lymphocytes are mature.

For viral transformation using EBV it is therefore preferable to use non-plasma cell peripheral blood lymphocytes. To establish a cell line, supernatant from a cell line producing the virus such as B95.8 (Miller et al 1972 Proc. Natl. Acad. Sci. USA 69 383–387) generally contains sufficient infectious virus particles. In practice, pellets of up to $10^7$ cells are suspended in approximately 1 ml of the viral culture supernatant and incubated at 37° C. for about 1 hour. This allows attachment of the virus to specific receptors on B-cells and cell penetration. It is preferable to agitate the container gently to prevent sedimentation. The cells so infected can then be cultured and the genes for the desired antibody can be cloned.

An alternative or an additional step to viral transformation is to fuse to myeloma cells to provide stabilisation (Crawford, D. H. 1985 Human Hybridomas and Monoclonal Antibodies Ed. E. G. Engelman, S. K. H. Foung, J. Larrick and A. Raubitschek pp 37–50 or Roder J. C. et al The Epstein-Barr virus-hybridoma technique ibid pp 55–67). The myeloma is optionally a heterohybridoma preferably of mouse/human origin. A suitable heterohybridoma can be generated for example from an antibody secreting cell-line such as HT01. Suitable cells can be selected on the basis of their sensitivity to hypoxanthine aminopterin and thymidine by subjecting them to sequential passage through medium containing 8-azaguanine as they are aminopterin sensitive.

In order to use such a heterohybridoma, the genes encoding endogenous human heavy and light chains must be deleted, otherwise the final cell line will be capable of producing more than one antibody and will not contain heavy and light chains for the desired antibody alone. This can be achieved by subjecting the cells to a 90% lethal dose of ultra-violet irradiation and selecting for suitable colonies by cytoplasmic staining with anti-human Ig and chromosome number namely polyploid with between 60–140 mouse chromosomes.

It is also advantageous to select vigorously growing cells. This may be achieved by passaging through the peritoneal cavity of a 2,6,10,14-tetramethylpentadecane (or pristane) primed mouse.

Final selection for growth, karyotype and fusability is then carried out, karyotype being the most important. The ideal heterohybridoma contains mainly mouse chromosomes.

Selection of a target lymphocyte cell line may be carried out by screening for the production of antibody which has affinity to the desired antigen, and antibody functionality.

Testing for affinity can be achieved by immunoassay techniques for example radioimmunoassay or Enzyme Linked Immunosorbent Assay (ELISA). Immunoassay techniques such as these use the specific interaction of antibody with antigen to provide information about antigenic specificity. Radioimmunoassays assess antibody level either by determining the capacity of antibody to complex with radioactive antigen or by measuring the amount of antibody binding to an insoluble antigen preparation. The ELISA technique involves conjugating enzymes to antigens or antibodies. The enzymes are usually selected on the basis of simple kinetics and can be measured by a coloured reaction product for example by spectrophotometry. Preferred enzymes include alkaline phosphatase, β-D-galactosidase and horseradish peroxidase. ELISA can be employed as a primary binding or a competitive binding assay. For example, lymphocytes isolated from an individual infected by a virus can be selected by culturing supernatant medium from one lymphocyte cell line in the presence of a suitably labelled viral antigen possibly in the form of whole or empty viral particles. The antibody/antigen complexes can then be identified as described above and the respective lymphocyte cell line selected for further studies.

The test for functionality of the antibody in the case of an infectious agent may involve competition studies for neutralisation for example viral neutralisation. Neutralisation studies can be carried out using Radioimmunofocussing Assay (RIFA), in which a fixed concentrate of purified antibody is cultured with equal volume of 10 fold dilutions of virus and then assayed for virus titre. An alternative test can be to use complement and test for cell lysis.

It is possible to obtain cells secreting human/or non-human primate IgG, IgG1, IgG2 or IgG3 IgM, IgA, IgD or IgE. These can be selected by Ouchtolony agar double diffusion or ELISA.

Following selection of a lymphocyte cell line expressing a functional antibody with the desired specificity, the total cell RNA can be isolated using standard recombinant techniques such as the method of Chomczynski and Sacchi (1987, Anal. Biochem. 162, 156–159). In order to isolate the specific messenger RNA (mRNA) encoding the antibody, standard techniques are also employed for example as described in Molecular Cloning: A Laboratory Manual by Maniatis et al Cold Spring Harbor Laboratory Press.

Complementary DNA (cDNA) is then synthesised from the mRNA by standard recombinant techniques as for example disclosed in the aforementioned Molecular Cloning Manual.

It is possible to employ between $1-3\times10^4$ and $1-3\times10^7$ lymphocytes for isolation of total cell RNA, however the invention further provides a method of cloning full length antibody genes from a much smaller number of cells as would be required from unstable antibody producing hybridomas or EBV transformed B cells of unknown stability. This method is therefore particularly useful for rescuing human or non-human primate antibodies from unstable cell lines, but may be applied to the rescue of any antibody heavy and/or light chain genes. This is made possible by advances in the reproducibility and quality of commercially available enzymes and vector systems for conventional cDNA cloning and the introduction of micro-RNA isolation techniques.

This improved method can be achieved by generating a size-selected cDNA library from as few as 1000 hybridoma cells. This library or a fraction of it may then be screened for immunoglobulin chains.

The invention therefore provides a method of cloning full length antibody genes comprising i) micro-RNA preparation from approximately 1000 cells, ii) generation of a size-selected cDNA library iii) screening the library for cDNA encoding heavy and light chains and iv) isolating the cDNA encoding the heavy and light chains.

The invention also provides a process for the production of a recombinant antibody comprising:

i) micro-RNA preparation from approximately 1000 cells;
ii) generation of a size-selected cDNA library;
iii) screening the library for cDNA encoding the heavy and light chains and isolating the same;
iv) inserting the cDNA encoding the heavy and light chains into an expression vector;
v) transfecting a host cell with the expression vector containing the cDNA; and
vi) culturing the transfected host cell and isolating the desired antibody.

Identification of cDNA clones which encode the antibody heavy and light chain proteins can be achieved by cloning the cDNA into a replicable vector for example a plasmid, and transforming a host cell for example a prokaryote such as E.Coli. The resultant library can then be screened for antibody light and heavy chain cDNA in the following manner.

Screening can be carried out using heavy and light chain DNA probes with detectable labels and a detection method for example as described in Gene Cloning by D. M. Glover (Published by Chapman and Hall Ltd London). These techniques can involve radiolabelling and detection by radiography methods or non-radioactive labels for example digoxigenin 11 dUTP and a detection kit for example the Nonradioactive DNA labelling and Detection kit available from Boehringer Mannheim. This screening method also allows completely unclassified antibodies to be screened for isotype using mixed probes for example human $\gamma$, $\mu$ and $\alpha$ H chain probes or $\kappa$ and $\lambda$ L chain probes.

Clones can be selected and if desired the sequence of the antibody heavy and light chains can be determined. It is also possible to introduce modifications into the antibody cDNA at this stage prior to preparation of vectors for expression; this may involve single codon or whole region modification. For example, class or species switching of the antibody isotype can be undertaken (ie: to form chimaeric antibodies). This can be achieved by generating fusions of the isolated V regions with the cDNA from the isotype of choice.

Once a suitable cell colony has been selected, the cDNA sequences for the light and heavy chain genes can be subcloned into vectors suitable for insertion into a host cell for expression. Construction of the expression vectors may be carried out in accordance with procedures known in the art (Molecular Cloning: A Laboratory Manual, Second Edition, Maniatis et al, Cold Spring Harbor).

The host cell must be capable of expressing the antibody in a functional form and therefore, should be a eukaryotic cell such as a mammalian cell e.g. myeloma or chinese hamster ovary (CHO) cells which are capable of carrying out post-translational modifications, in particular, correct folding of the chains, and glycosylation, which can be essential for effective functionality of the constant region of an antibody. Eukaryotic cells can be cultured in vitro quite successfully and are known to express functional antibody. Yeast or insect cells may also serve as host cells as they can also carry out desired post-translational modifications.

The heavy and light chain cDNA can be transfected in a single vector as described in WO87/04462 or co-transfected in two vectors as described below. Reference hereinbefore and hereinafter to transfection of a host cell line with an expression vector includes within its meaning co-transfection of the host cell employing more than one vector unless it is clear from the context that only co-transfection is being referred to.

The vectors for co-transfection preferably contain independently selectable markers, the resulting colonies may thus be selected for both markers. Colonies exhibiting the dual phenotype are generally capable of co-expressing both the light and heavy chains. The selectable markers may or may not be of a dominant nature. Examples of selectable markers include adenosine deaminase (Kaufman et al, *P.N.A.S.*, 1989, 83 3136–40) asparagine synthetase (Cartier et al, *Mol. Cell Biol.*, 1987, 7, 1623–28), *E.coli* trpB gene and Salmonella hisD gene (Hartman et al, *P.N.A.S.*, 1988, 85, 8407–51), M2 mouse ribonucleotide reductase (Thelander et al, *EMBO J*, 1989, 8, 2475–79), human multidrug resistance gene (Kane et al, *Gene*, 1989, 84, 439–446), glutamine synthetase (Bebbington et al, *DNA Cloning*, Vol III, 1987, Ed. D. M. Clover, 163–188, IRL Press), xanthine guanine phosphoribosyl transferase (gpt) (Mulligan et al, *Science*, 1980, 209, 1422–27), hygromycin B (Santerre et al, *Gene*, 1984, 30, 147–156), neomycin gene (Southern et al, *J. Mol. Appl. Genet.*, 1982, 1, 327 341), and dihydrofolate reductase (Subramani et al, *Mol. Cell Biol.*, 1981, 1, 854–868).

A preferred selectable marker for use with one of the vectors is dhfr which is usually employed with a parental Chinese Hamster Ovary (CHO) cell line of the dhfr$^-$ phenotype (Urlaub et al, *P.N.A.S.*, 1980, 77, 4216–4220). Successfully transfected CHO cells will possess the dhfr$^+$ phenotype and can readily be selected by culturing the colonies on media devoid of thymidine and hypoxanthine and optionally containing methotrexate (MTX). A preferred selectable marker for use with the other of the vectors is a dominant resistance marker, such as neomycin (neo). CHO cells successfully transfected with this marker can readily be selected by culturing the colonies in media containing the antibiotic, Geneticin, an analogue of neomycin.

Another expression system for use with CHO or myeloma cells is the glutamine synthetase (GS) amplification system described in WO87/04462 the method of which is incorporated herein by reference. This system involves the transfection of a glutamine dependent cell with a gene encoding the GS enzyme and the desired antibody heavy and light chain genes. Cells are then selected which grow in glutamine free medium. These selected clones are then subjected to inhibition of the GS enzyme using methionine sulphoximine (Msx). The cells, in order to survive, will amplify the GS gene with concomitant amplification of the gene encoding the antibody.

As described previously a selectable marker such as GS preferably also provides the basis upon which the genes encoding the light and heavy chains may be amplified. In transfection of a cell line, the vector DNAs are often integrated into the chromosome of the cell at the same locus. Thus, the use of a selectable marker as the basis for amplification normally results in a parallel increase in the copy number of both genes. Similarly, dhfr is a selectable marker which enables desired amplification through the use of increasing concentrations of the inhibitor MTX.

The selectable markers are of course under the control of regulatory elements of DNA so as to provide for their expression. The regulatory elements are preferably of a viral source, such as from DNA tumour viruses. Particularly preferred are the SV40 or adenovirus major late promoter. It is particularly advantageous in this regard to remove the enhancer element from the promoter thus effectively "crippling" it. This modification allows for increased levels of gene amplification at each concentration of inhibitor than would otherwise occur if a strong promoter was used. In the case of the use of GS as a selectable marker, an example of a suitable promoter is the mouse metallothionein promoter or preferably the human cytomegalovirus (hCMV)-MIE promoter described in PCT patent publication number WO89/01036.

The antibody light and heavy genes are also under the control of regulatory elements of DNA so as to provide for their expression. The use of the same regulatory elements for both chains is preferred so that their expression is substantially balanced. The regulatory elements may be of viral origin and examples include those mentioned above in conjunction with the expression of dhfr or GS as a selectable marker. Another example is the use of the β-actin promoter and cognate β-actin polyadenylation signal.

One or both of the vectors may also contain an SV40 origin of replication to allow for the vector constructs to be checked by rapid transient assay for example in COS cells.

Co-transfection of the cell line with the expression vectors may be carried out simply by using equimolar quantities of both vectors and standard transfection procedures, such as calcium phosphate precipitation or lipofectin. Selection of the desired co-transfected cell line may be carried out in accordance with standard procedures known for the particular selectable markers.

The invention therefore includes a vector suitable for transfection of a host cell comprising cDNA encoding primate antibody heavy and light chains.

The invention therefore includes a eukaryotic cell line transfected with cDNA for the expression of primate antibody heavy and light chains.

The invention further includes a process for the expression of cDNA encoding primate antibody heavy and light chains comprising transfecting a eukaryotic host cell with a vector or vectors suitable for the expression of said cDNA.

Culture of the cell line may be carried out in serum-containing or preferably serum-free media. It is particularly advantageous during purification if protein-free medium is employed. Where the cell line is a CHO dhfr$^+$ transformant, the medium preferably lacks hypoxanthine and thymidine and optionally contains MTX. When using the GS system it is advantageous to employ a glutamine dependent cell line and a glutamine free medium. Expression of both chains in substantially equimolar proportions enables optimum yields of functional antibody to be obtained. The two chains assemble within the cell and are then secreted into the culture media as functional antibody. The resulting recombinant antibody may be purified and formulated in accordance with standard procedures.

One aspect of the present invention includes recombinant non-human primate antibody, more particularly recombinant chimpanzee or old world monkey antibody for example recombinant cynomolgus monkey antibody.

The invention further comprises a recombinant primate antibody produced or produceable by:

i) selecting a primate lymphocyte derived cell line that is capable of expressing a desired antibody;

ii) isolating RNA from the cell-line and separating mRNA from the other RNA so isolated;

iii) synthesising cDNA from the mRNA and inserting the cDNA into a cloning vector;

iv) transforming a host cell with the vector containing the cDNA—to obtain a library;

v) screening the library for cDNA encoding the antibody;

vi) inserting the cDNA en coding the antibody into an expression vector;

vii) transfecting a host cell with the expression vector containing the cDNA; and viii) culturing the transfected host cell and isolating the desired antibody.

The use of eukaryotic cell lines transfected with cDNA can be expected to yield greater than 50 μg/ml of antibody preferably up to or more than 250 μg/ml.

A further aspect of the invention comprises a recombinant primate antibody produced or produceable by the process of culturing a eukaryotic host cell line capable of expressing cDNA encoding primate antibody heavy and light chains.

The resultant antibody can be used as a therapy, according to its specificity. One example provided hereinafter is a human anti-hepatitis A antibody for use in the treatment of hepatitis A infections. Other anti-viral antibodies can be obtained which target viruses such as other hepatitis viruses (e.g. hepatitis B and C) or herpes viruses : herpes simplex virus, cytomeglovirus, Epstein Barr virus, varicella zoster virus. Anti-HIV antibodies can be obtained according to the invention. These antibodies may be used to treat AIDS, to prevent or delay onset of AIDS in HIV positive or ARC patients, or prophylactically in individuals who have come into contact with the virus through, for example needlestick injury. Another use is in the prevention of transmission of the virus from an HIV positive mother to her infant during-pregnancy or at childbirth. This may involve treatment with the antibody before, during and/or after birth.

Antibodies may also be obtained which target other pathogenic organisms such as bacteria, protozoa etc. Cancerous cells are also possible targets for human antibodies. Optionally the antibodies can be used as targeting moieties which deliver chemical or biological compounds. These are incorporated into the cell by endocytosis where they are toxic or are metabolised to form a toxic agent, killing the cell. Antibodies of the invention may target other anti-self antigens such as those present in autoimmune diseases for example multiple sclerosis or in for example inflammatory disorders such as arthritis. Anti-Rhesus D antibodies cannot be made in animal models—a human antibody would therefore have great value as a diagnostic tool in blood typing and/or could be employed therapeutically. Anti-rhesus D antibody can be administered to a rhesus negative mother at any time during pregnancy or birth to prevent her from raising antibody against the foetus or during subsequent pregnancies. A further aspect of the invention therefore includes the use of a recombinant human antibody in the treatment or prophylaxis of exposure of a rhesus negative individual to rhesus D antigen.

Antibodies rescued in accordance with the invention could be employed in general diagnostic methods.

It will be clear from the disclosure that although the invention is primarily concerned with rescue of entire antibody heavy and light chain genes, that fragments such as F(ab) F(ab)$_2$ and FV can be rescued, expressed and used separately. Such fragments are included within the definition of 'antibody'.

The present invention therefore provides the use of primate antibodies in the manufacture of a medicament for the treatment of the aforementioned diseases and conditions. Thus, the invention extends to methods of prophylaxis and/or treatment of a human disease and/or condition as described above, comprising administration to a human of an efficacious amount of a primate antibody. Such methods include methods of diagnosis.

The dosages of the antibodies will vary with the condition being treated and the recipient of the treatment, but will be in the range 1 to about 100 mg for an adult patient, preferably 1–10 mg, usually administered daily for a period between 1 and 30 days. A two part dosing regime may be preferable wherein 1–5 mg are administered for 5–10 days followed by 6–15 mg for a further 5–10 days.

Also included within the invention are pharmaceutical formulations containing a recombinant primate antibody. Such formulations preferably include, in addition to antibody, a physiologically acceptable diluent or carrier possibly in admixture with other agents such as other antibodies and/or an antibiotic. Suitable carriers include but are not limited to physiological saline, phospate buffered saline, glucose and buffered saline. Alternatively, the antibody may be lyophilised (freeze-dried) and reconstituted for use when needed, by the addition of an aqueous buffered solution as described above. Routes of administration are routinely parenteral including intravenous, intramuscular, subcutaneous, and intraperitoneal infection or delivery.

DESCRIPTION OF FIGURES

FIGS. 1(a) and 1(b) and FIGS. 2(a) and 2(b). Nucleotide and deduced amino acid sequences of Antibody D heavy chain and light chain respectively. The complete sequence of the pH210H2 insert is shown. The signal peptide and CDR sequences are underlined, and the predicted polyadenylation signal overlined. Amino acids are numbered according to Kabat et al. (1987).

Figure 1:
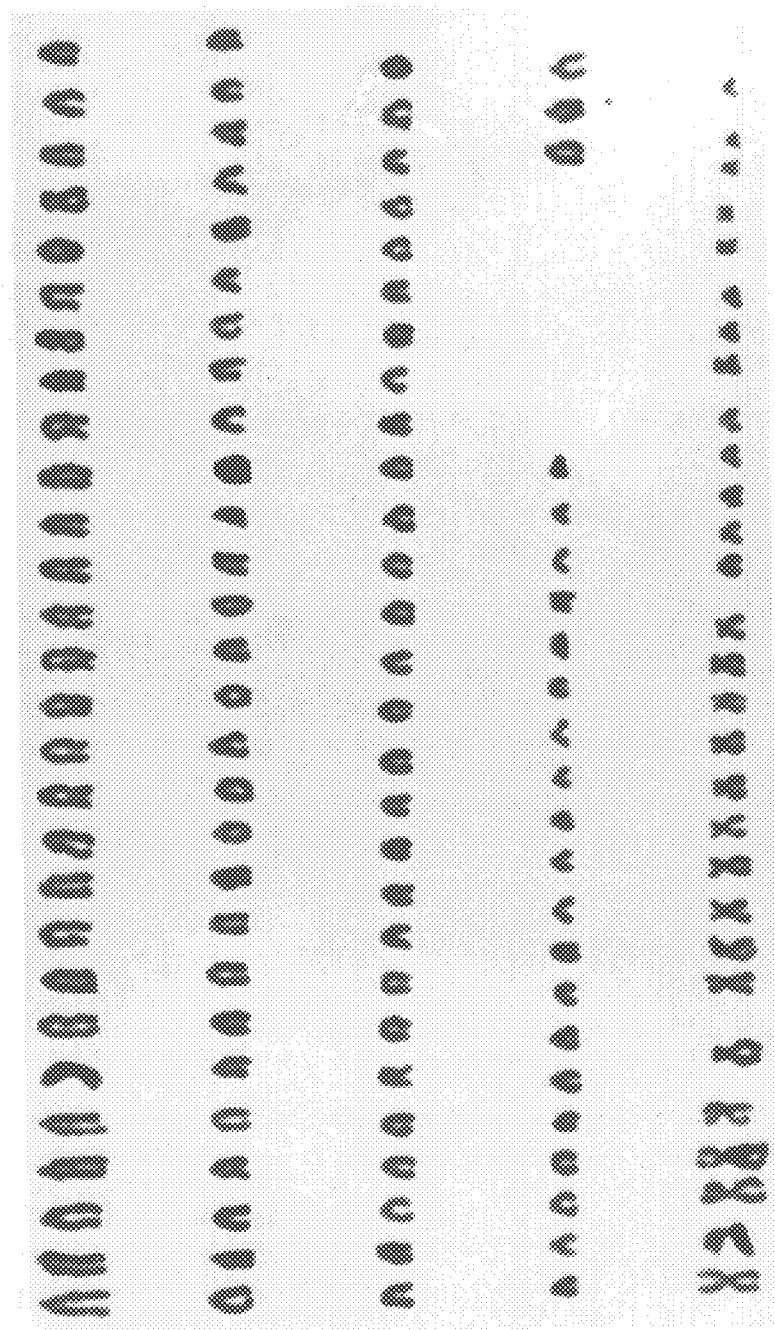
FIG. 1. Karyotypic analysis of HT01 cells showing polyploid modal numbers of mouse chromosomes and many human chromosomes.

The antibody D heavy chain nucleotide and amino acid sequences correspond to Sequence ID Nos: 9 and 10, and the light chain nucleotide and amino acid sequences correspond to Sequence ID Nos: 11 and 12.

FIGS. 3(a) and 3(b). Nucleotide alignment of cynomolgus kappa light chain variable regions with human, rabbit and mouse sequences. CDRs are indicated and dots indicate identity to the human Walker sequence. Codons are numbered according to Kabat et al.

The nucleotide sequences presented in FIG. 4 correspond to Sequence ID Nos: 13, 15, 17, 19, 21, 22, 25, 27, 29, 31, 33, 35 and 37, respectively.

Figure 4B:
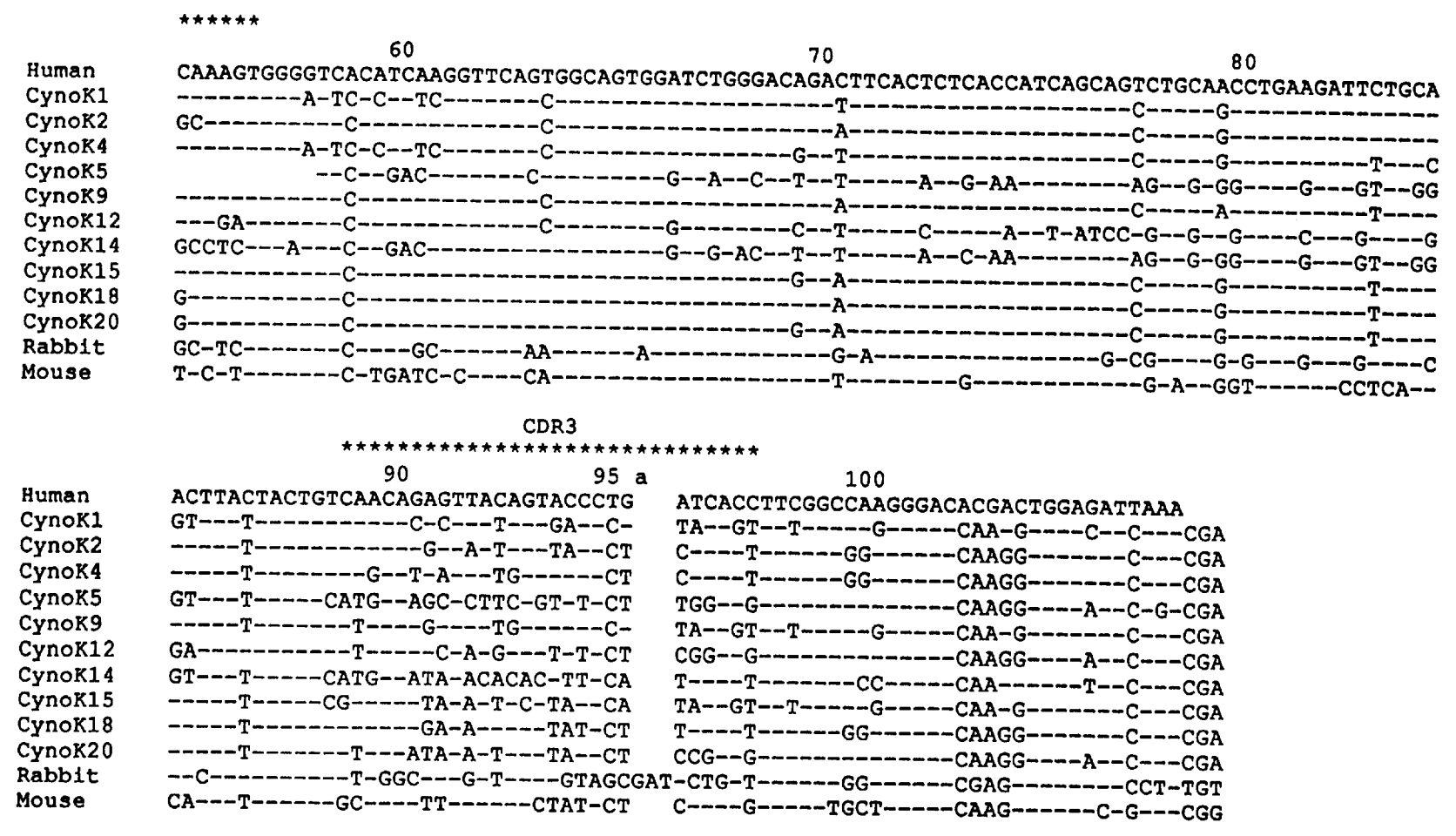

FIGS. 4(a) and 4(b). Amino acid alignment of cynomolgus kappa light chain variable regions with human, rabbit and mouse sequences. CDRs are indicated and dots indicate identity to the human Walker sequence. Amino acid residues are numbered according to Kabat et al.

Figure 5A:
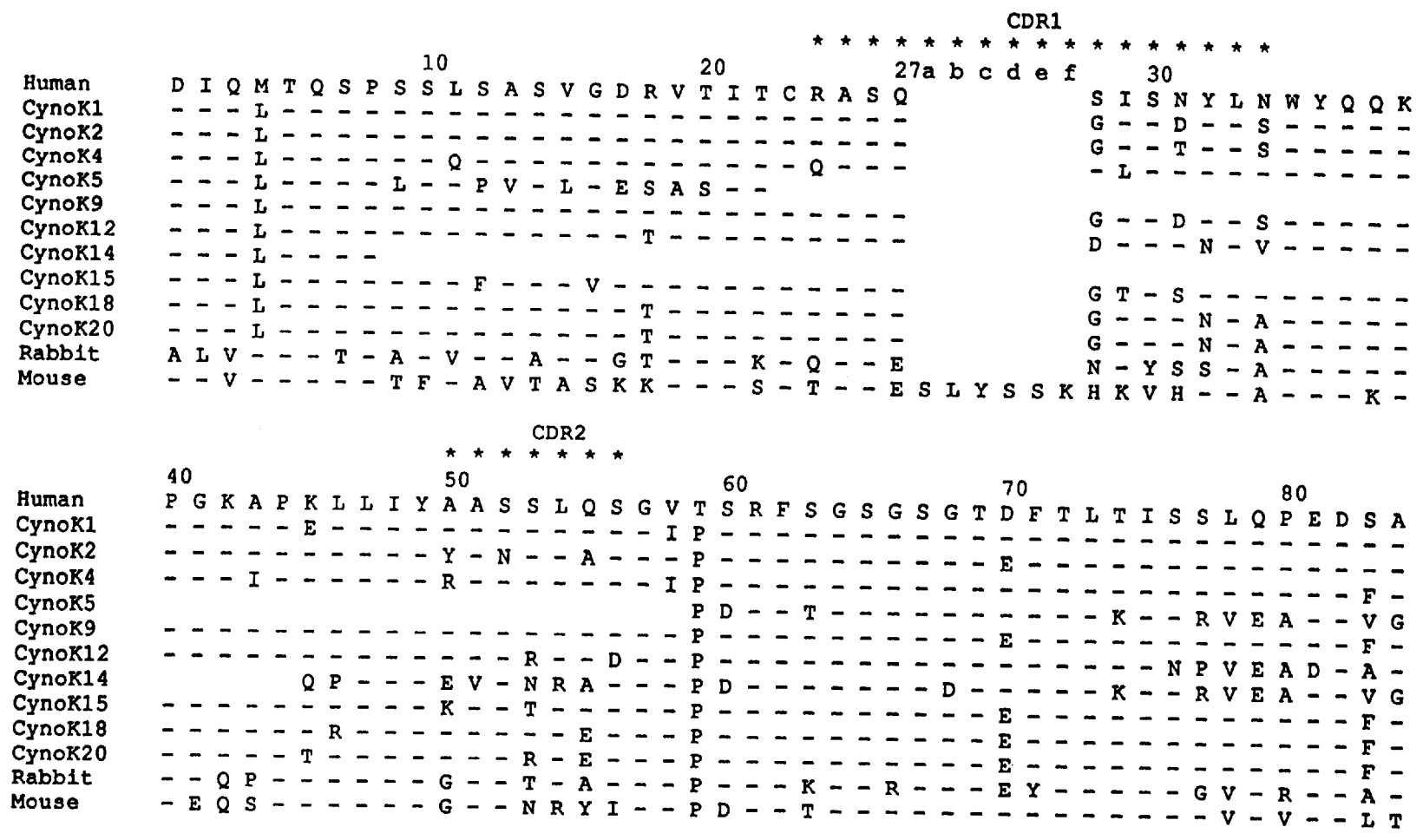

The amino acid sequences presented in FIG. 5 correspond to Sequence ID Nos: 14, 16, 18, 20, 22, 24, 26, 28, 30, 32, 34, 36 and 38, respectively.

FIG. 5. Nucleotide alignment of cynomolgus kappa light chain constant region with human, rabbit and mouse sequences. Dots indicate identity to the human germline sequence. Codons are numbered according to Kabat et al. One of the ten monkey sequences possessed a G at the nucleotide position underlined.

The nucleotide sequences presented in FIG. 6 correspond to Sequence ID Nos: 39, 41, 43 and 45.

FIG. 6. Amino acid alignment of cynomolgus kappa light chain constant regions with human, rabbit and mouse sequences. Dots indicate identity to the human germline sequence. Amino acid residues are numbered according to Kabat et al.

The amino acid sequences presented in FIG. 7 correspond to sequence ID Nos: 40, 42, 44 and 46.

EXAMPLES

Production of Human/Mouse Chimaeric Cells for Hybridisation

Example 1

Rescue of human anti-hepatitis A antibody.
a) Production of cell line HT01

50 ml blood taken from a healthy human donor, 7 days after booster immunisation with tetanus toxoid, and mixed with preservative-free heparin as anti-coagulant. Mononuclear cells separated on Ficoll/Hypaque (Boyum A. 1986 Scand.J.Clin.Invest. 21, 77–89), washed in Hanks buffered saline and fused with a mouse myeloma cell line by conventional techniques as follows:

NS-O mouse myeloma cells (Galfre C. and Milstein C. (1982) Immunology 45, 125–128) were harvested from a log-phase culture and washed in Hanks saline. Mononuclear cells ($4.7 \times 10^7$) and NS-O cells ($6 \times 10^7$) were mixed and centrifuged in a 50 ml test tube. The pellet of cells was then resuspended in 1 ml 50% polyethylene glycol solution and mixed gently for 1 minute at room temperature. The fused cells were resuspended in RPMI medium with 10% foetal calf serum and dispensed drop-wise into 60 1 ml aliquots of this growth medium in 24 well plates.

24 hours later 1 ml of medium containing hypoxanthine aminopterin and thymidine (HAT) and $1 \times 10^6$ Balb/c mouse spleen cells was added to each well. The plate was incubated at 37° C. in 5% $CO_2$.

20 days after fusion the supernatants were screened by radio-immunoassay for human anti-tetanus toxoid antibodies. One well containing one small colony of cells (approximately 20) was identified. This colony was slow-growing, a characteristic associated with prolonged stability of antibody secretion due to enhanced retention of human chromosomes.

These cells were transferred to a fresh well and after three weeks were cloned by limiting dilution (LD). All the subclones tested were positive in the Radioimmunoassay (RIA).

One clone, PB47 1.A1.B9.E10, was named HT01 and cells frozen down. These cells synthesised human IgM anti-tetanus toxoid antibody.

Karyotypic analysis showed that the cells contained a polypoid modal number of mouse chromosomes and many human chromosomes. These cells were selected as starting material for production of a polypoid fusion partner for the preparation of further hybridomas.

The cell line HT01, which secreted human IgM anti-tetanus antibody was used as starting material to produce a polyploid fusion partner. Cells sensitive to HAT were selected by subjecting the aminopterin resistant HT01 cells to sequential passage through medium containing 8-azaguanine, from 1 μg–20 μg/ml.

In order to stimulate loss of the human antibody heavy and light genes, a sample of cells was subjected to a 90% lethal dose of ultra-violet irradiation. Irradiated cells were cloned at limiting dilution and a number of colonies were selected on the basis of lack of cytoplasmic staining with anti-human Ig and nuclear size which correlates with chromosome number. One clone, HT01.A was selected after karyotypic analysis showed it to be polyploid with between 60–140 mouse chromosomes.

Selection of vigorously growing HT01.A cells was achieved by passaging a sample through the peritoneal cavity of a pristane-primed mouse (PRISTANE is 2,6,10, 14—tetramethylpentadecane from Aldrich). Those cells that survived, grew as single colonies on microtitre plates. These were cultured and assessed for growth, karyotype and fusibility. One, designated HT01.A.P1 was finally selected on the basis of modal numbers of 135 mouse and 3 human chromosomes. This cell line was used as a fusion partner with the peripheral blood lymphocytes from the hepatitis A virus seropositive donor.

b) Removal and stabilisation of antibody secreting cells

A blood sample (30 mls) was obtained from a hepatitis A virus (HAV) sero positive donor, approximately four months after an infection with hepatitis A contracted from contaminated food in the UK.

Peripheral blood lymphocytes were separated on a lymphoprep gradient (Flow Labs), transformed with Epstein Barr Virus (EBV) and cultured for ten days in medium containing phaetohaemaglutinin and 10% foetal calf serum. They were then fused with appropriate human/mouse chimeric cells as described above, using PEG 1500, and cultured in the presence of HAT and $10^{-5}$M ouabin in 2 ml wells. Supernatant media were screened by sandwich ELISA for anti-HAV activity, ten days post-fusion when distinct colonies were visible microscopically. Individual colonies were picked from positive wells, and monoclonal cell lines established from these by cloning twice from single cells at limiting dilution. Of the original 42 2 ml wells, seventeen were strongly positive in initial ELISA screens following extensive re-feeding, but secreting monoclonal lines were only successfully established from four of these. The others ceased secreting antibody at various states of isolation or cloning, including after double cloning, presumably due to the inherent chromosomal instability of heterohybrids.

c) Selection of hybridoma

ELISA Studies

The four antibodies (A, B, C & D) from the cell lines described above, were titrated in both Sandwich and Direct ELISA against full and natural empty HAV particles. The titres, expressed as the log 10 reciprocal dilutions producing 50% of the maximum absorbance plateau, are shown in Table 1a. These values, expressed as percentages of the titres of individual antibodies against native particles in the Sandwich test are given in Table 1b.

TABLE 1a

ELISA TITRES OF HUMAN ANTIBODIES AGAINST FULL AND NATURAL EMPTY HAV PARTICLES

| Antibody I.D. | Sandwich | | Direct | |
| --- | --- | --- | --- | --- |
| | Fulls | Empties | Fulls | Empties |
| Antibody A | 4.42 | 4.42 | 3.77 | 3.35 |
| Antibody B | 4.85 | 4.78 | 4.13 | 3.80 |
| Antibody C | 3.91 | 3.72 | 4.02 | 3.59 |
| Antibody D | 4.10 | 4.15 | 3.92 | 3.60 |

TABLE 1b

ELISA ACTIVITY OF ANTIBODIES EXPRESSED AS PERCENTAGE OF THE HOMOLOGOUS ANTIBODY TITRE AGAINST FULL PARTICLES IN THE SANDWICH TEST

| Antibody I.D. | Sandwich | | Direct | |
| --- | --- | --- | --- | --- |
| | Fulls | Empties | Fulls | Empties |
| Antibody A | 100 | 100 | 22 | 9 |
| Antibody B | 100 | 85 | 19 | 9 |
| Antibody C | 100 | 65 | 126 | 48 |
| Antibody D | 100 | 112 | 66 | 32 | d) Competition Studies

The ability of the antibodies to inhibit both each other and murine antibodies from binding to the virus was carried out using solid phase radioinmunoassay (RIA) and ELISA techniques, which only differ at the final stage. The results, expressed in Table 2 as the maximum competition (%) obtained between antibody pairs, show that;

I) Antibodies A and B are indistinguishable and are similar to the K24F2 murine antibody (MacGregor A. et al 1983, J.Clin.Microb. 18 page 1237).

II) Antibody D is closer in nature to murine antibody B5B3, (Stapleton J. T. and Lemmon S. M. 1987 J. Virol. 61 p491) and only interferes with Antibody A to a maximum of approximately 30% in reciprocal tests.

III) Antibody C appears to be functionally intermediate between Antibody A and D.

IV) Both Antibody A and Antibody D were individually able to inhibit the binding of human HAV polyclonal sera (Lemmon S. M. et al 1983 J.Clinical.Microb. 17 page 834 namely-Foxwell and Chulay) very efficiently.

The high competition values obtained with Antibodies A and B against B5B3 were obtained with 10-fold concentrated antibody, whereas the tissue culture supernates produced only 20% competition or less. In contrast, the same supernates required substantial dilution to obtain full competition curves against the K24F2 and K34C8 antibodies (MacGregor A. et al 1983, J.Clin.Microb. 18 page 1237) as did the Antibody D supernate against B5B3.

TABLE 2

MAXIMUM COMPETITION (%) OF ANTIBODY BINDING TO THE 18F HAV STRAIN

| 4th Ab (Detection) | | | | | | Human Polyclonal |
| --- | --- | --- | --- | --- | --- | --- |
| 3rd Ab (Competitor) | A | D | K34C8 | K24F2 | B5B3 | Antiserum (Chulay) |
| Antibody A | 100 | 32 | 90 | 100 | 96[1] | 94 |
| Antibody B | 100 | 33 | 78 | 100 | >65[1] | |
| Antibody C | 66 | 55 | 46 | 72 | 91 | |

TABLE 2-continued

MAXIMUM COMPETITION (%) OF ANTIBODY BINDING TO THE 18F HAV STRAIN

| 3rd Ab (Competitor) | 4th Ab (Detection) | | | | | Human Polyclonal Antiserum (Chulay) |
|---|---|---|---|---|---|---|
| | A | D | K34C8 | K24F2 | B5B3 | |
| Antibody D | 24 | 100 | 29 | 69 | 99 | 92 |
| Antibody A & D 1:1 mix | | | | | | 99 |
| K34C8 | 100 | 32 | 100 | | | |
| K24F2 | 100 | 70 | | 100 | | |
| B5B3 | 69 | 100 | | | 100 | |
| Human polyclonal antiserum (NF) | | | | | | 100 |

[1]Concentrated antibody required for maximum competition e) RIFA Studies

All antibodies detected by the initial screening ELISA were also positive in Radioimmunofocussing Assay against the 18f virus. (Daemer R. J. et al (1981). Infec & Immunol. 32 page 388; and Stapleton J. T. and Lemmon S. M. (1987) J.Virol Vol 61 p492; and Ping L. A. et al 85 p821). The reductions in virus RIFA titres, obtained from reacting equal volumes of a fixed concentration (1 mg/ml) of affinity purified antibody with 10-fold dilutions of the 18f and 43c virus strains (43c strain was derived from 18f strain by passaging under pressure from a murine monoclonal), are summarised in Table 3. These demonstrate that mutant 43c is very poorly neutralized by either antibody but shows significant, albeit reduced neutralization with polyclonal Foxwell serum.

Although both antibodies appear to 'neutralize' 18f virus far less efficiently than polyclonal serum, this is largely due to a fairly constant number of residual plaques surviving at each virus dilution and consequently distorting the Spearman-Karber calculation of titre. Reaction with polyclonal serum, however, eliminated all plaque formation. Similar reaction slopes of the antibodies to polyclonal sera in competition studies, and their overall ELISA reactivity, give no indication that these represent low affinity antibodies.

TABLE 3

REDUCTION IN TITRE $LOG_{10}$ PLAQUE FORMING UNITS/ML OF HAV ISOLATES REACTED WITH SPECIFIC ANTIBODY

| HAV strain | A (1 mg/ml) | Antibody D (1 mg/ml) | Polyclonal human serum, (1/10) |
|---|---|---|---|
| 18f | 3.15 | 2.72 | >4.56 |
| 43c | 0.68 | 0.78 | 1.93 | f) Cloning and sequencing of the anti-hepatitis A virus monoclonal Antibody D heavy and light chains Method 1

Total RNA was isolated from $2.5\times10^7$ Antibody D expressing cells following the method (1) of Chomczynski and Sacchi (1987 Anal. Biochem. 162 156–159), using 1 ml of extraction solution per $1\times10^7$ cells. The resulting RNA pellet was redissolved in 50 $\mu$l diethyl pyrocarbonate (DEPC)-treated distilled water, and spectrophotometri-cally determined to be at a concentration of 4.4 $\mu$g/$\mu$l. Dynabeads Oligo $(dT)_{25}$ (Dynal Winal, UK) was used to extract polyadenylated RNA from 75 $\mu$g total RNA employing the manufacturer's protocol.

Method 2

An alternative method (2) for isolation of polyadenylated RNA involved isolation directly from $10^3$ Antibody D secreting cells using the Micro-FastTrack mRNA isolation system (Invitrogen, San Diego, USA) following the method recommended by the manufacturer.

The ability to clone human antibody genes from a limited number of cells was investigated. A cDNA library was generated with polyadenylated RNA isolated from one thousand secreting antibody D cells using Method 2 above. The library was calculated to possess a potential of about 2000 size-selected (>500 bp) cDNA inserts. Half of the library was plated and screened for human κ L chain, and 2 positive clones detected. Partial sequencing confirmed that both clones possessed full length L chain genes, incorporating signal peptide sequences. Although this library was not screened with the H chain probe, full length H chain inserts should be present as calculated from the frequency of H chain positives (2/500) obtained from the initial cDNA library.

cDNA was synthesised from the isolated mRNA and cloned into the plasmid pSPORT-1 using the SUPERSCRIPT Plasmid System for cDNA Synthesis and Plasmid Cloning kit (GIBCO/BRL. Paisley, UK) following the method recommended by the manufacturer. *Escherichia coli* MAX EFFICIENCY DH5α Competent Cells (GIBCO/BRL) were transformed with the resulting cDNA/pSPORT-1 ligation. Approximately 4500 colonies were lifted onto Hybond-N nylon filters (Amersham) and lysed, denatured and fixed following the method of Buluwela et al. (Nucleic Acids Res, 1989 17 452). The filters were treated with proteinase K (50 $\mu$g/ml in 0.2× SSC, 0.1% SDS at 55° C. for 30 min), and then excess debris removed with a tissue. The libraries were then screened for human antibody heavy and light chain sequences using heavy and light chain probes.

The heavy chain probe was a human IgG1 antibody cDNA insert (rat CAMPATH-1 [Campath is a trademark of The Wellcome Foundation Limited] antibody heavy chain CDRs reshaped on human NEW IgG1 antibody heavy chain; Riechmann et al., 1988 Nature 382 323–327) which was labelled with digoxigenin-11-dUTP using the Nonradioactive DNA Labelling and Detection Kit (Boehringer Mannheim) and employed to screen filters, possessing approximately 500 lifted colonies, for Antibody D heavy chain following the manufacturer's protocol. Two potential positive colonies were detected and selected for further analysis. Plasmid DNA was prepared using the QIAGEN PLASMID KIT (DIAGEN, DUSSELDORF, FRG) or the method of Del Sal et al. (1988 Nucleic Acids Res 16 9878) and both of the potential positive clones were found to contain inserts of the expected size for human immunoglobulin heavy chain cDNA. A clone, pH210H2, was selected, and sequenced in both directions by plasmid priming following the dideoxy chain termination method (Sanger et al., Proc. Natl. Acad Sci USA, 1977 74 5463–5467), according to the Sequenase kit (United States Biochemicals—USB Cleveland, USA) protocol. The C region of the heavy chain was determined to be λ1. The sequence of the variable region is shown in FIGS. 1(*a*) and (*b*).

The light chain probes were human lambda cDNA (humanised anti-CD3 mAb λ L chain insert [rat anti-CD3 mAb L chain CDR's reshaped an human λ $Kern^-Oz^-$ Ab L chain: E Routledge Eur.J.Immunol. 1991; 21:2717) and (a Campath-1H κ L chain cDNA insert (rat Campath 1 mAb L chain CDR's reshaped on human REI κ AB L chain; Page and Sydenham Bio/technology 1991; 9:64;) which was labelled with digoxigenin-11-dUTP using the Nonradioactive DNA Labelling and Detection Kit (Boehringer Mannheim, Lewes, UK) and employed to screen filters, possessing approximately 4000 lifted colonies, for antibody D light chain following the manufacturer's protocol. Twenty potential positive colonies were detected and 10 selected for further analysis. Plasmid DNA was prepared using the QIAGEN Plasmid kit (DIAGEN, Dusseldorf, FRG) or the method of Del Sal et al. (1988) and 8 contained inserts of the expected size for human antibody light chain cDNA. A clone, pH210L2, was selected, and sequenced in both directions by plasmid priming following the dideoxy chain termination method (Sanger et al., 1977), according to the Sequenase kit (USB, Cleveland, USA) protocol. The light chain was determined to be a $\lambda$ sequence the variable region of which is shown in FIGS. 2(a) and 2(b).

g) Assembly of Expression Constructs

Example g.i)

The expression vector pRDN1 was adapted from the pLD9 plasmid (described in Page, M. and Sydenham M. A. (1991) Biotechnology 9 64–68) as follows. The HindIII site used to insert the $SV_{40}$ origin of replication and the other HindIII site 5' to the DHFR coding sequence were destroyed by HindIII digestion, filled-in with klenow fragment of DNA polymerase, and re-ligated. A clone lacking both restriction sites was digested with $EcoR_1$, filled-in with klenow enzyme and re-ligated. The resulting plasmid, lacking all internal HindIII and $EcoR_1$, sites, was used to insert the human $\beta$ Actin expression cassette downstream of the DHFR transcripiton unit. This plasmid, has a functional SV40 origin of replication and pRDN1 has unique HindIII and $EcoR_1$, restriction sites downstream of the $\beta$ Actin promoter. The adapted pRDN1 vector was digested with EcoRI, blunted with Klenow enzyme and dephosphorylated using calf intestinal phosphatase. The Antibody D heavy and light chain inserts were cut out of their respective clones, pH210H2 and pH210L2, using HinddIII and $EcoR_1$, and blunt ended with Klenow enzyme. The blunt ended inserts were ligated into pRDN1 and used to transform *Escherichia coli* MAX Efficiency DH5 Competent Cells (Bethesda Research Labs BRL). Small-scale plasmid preparations (Del Sal, G. et al. (1988) Nucleic Acids Res. 16 9878) were carried out on a number of the resulting colonies and the inserts orientated using appropriate restriction digests. Plasmid DNA was prepared from one heavy and one light chain clone (pRDHH9 and pRDHL27 respectively) using QIAGEN (trademark) columns (Hybaid) following the manufacturer's protocol.

Transfection of COS cells $2 \times 10^5$ COS cells were plated in D-MEM (plus serum) in each well of a 12-well tissue culture dish. After 24 hours, the cell monolayers were rinsed twice with serum-free medium followed by 0.5 ml of serum-free medium containing 1 $\mu$g of each DNA construct (pRDHH9 and pRDHL27) and 5 $\mu$g TRANSFECTAM (Northumbria Biologicals Limited), as recommended by the manufacturer. After further incubation for 6 hours, the transfection medium was aspirated and replaced with 1 ml D-MEM (plus serum). After 48–72 hours, the medium was removed and assayed for human antibody.

ELISA Assay for Human Antibody

The medium from the COS cell transfection was assayed for the presence of human antibody. In the absence of light chain synthesis, heavy chains are not secreted from a cell and are degraded internally (Hendershot L. et al. Immunol. Today 8 111–114). Antibody can thus be assayed by detection of heavy chain in the culture medium. Microtitre plates were coated with anti-human IgG and incubated with the culture medium. Antibody was detected by visualisation with an anti-human gamma chain specific peroxidase conjugate.

Example g.ii)

The DNA encoding the H and L chains was cloned into the pEE6hCMV (Stephens and Cockett Nucl. Acids Res. M: 7110 1989; Bebbington et al. Biotechnology 10 169 1992) and pEE12 (Rolfe unpublished) expression vectors respectively. Plasmid pEE12 contains a cDNA encoding the hamster glutamine synthetase gene (GS; a marker that can be selected and amplified using the toxic glutamate analogue, L-methionine sulphoximine [MSX]) under the control of the SV40 early promoter and SV40 splicing and polyadenylation signals obtained from pSv2.GS (Bebbington and Hentschel DNA cloning volume III New York Academic Glover DM ed. 1987). Downstream of this selection cassette is the complete enhancer, promoter and 5' UTR from the major immediate early (MIE) gene of the human cytomegalovirus (hCMV), and this is used to drive expression of the antibody gene. This expression cassette with its associated origin of replication and $\beta$-lactamase gene were obtained from pEE6.HCMV (Stephens and Cockett Nucl. Acids Res. 17: 7110 1989). Cells transfected with vectors pEE6hCMV and pEE12 are therefore capable of growth in glutamine minus medium. Plasmids pEE6hCMV and pEE12 were obtained from Celltech Ltd, Slough, Berkshire, SL1 4EN, UK).

Recombinant plasmids (5 $\mu$g of each) were transfected into $5 \times 10^5$ COS-1 cells or $10^7$ YO myeloma cells using the Transfectam reagent (Promega, Southampton, UK) under the conditions recommended by the manufacturer. As a result, the selection is only on the pEE12 plasmid and effective expression relies upon co-integration of the two plasmids.

H and L chains were co-transfected in COS cells to ensure that the constructs were correctly inserted in frame, efficiently transcribed and translated, and that the resulting human antibody was properly secreted. Having confirmed transient expression of the antibody by ELISA the plasmids were co-transfected into YO myeloma cells.

Stock COS-1 cells (Source ECACC, Porton Down, UK) were maintained in DMEM medium (Flow, Irvine, UK) supplemented with 10% foetal calf serum (APP, Dudley, UK). COS cell transfections were carried out in DMEM medium (Flow, Irvine, UK).

Stock YO cells (Source ECACC, Porton Down, UK) were maintained in complete medium containing DMEM medium (Flow, Irvine, UK; without glutamine and ferric nitrate but with sodium pyruvate [110 mg/L]; GIBCO/BRL, Paisley, UK) 1× non-essential amino acids (Flow, Irvine, UK) and 10% foetal calf serum (APP, Dudley, UK). Transfected cells were transferred to 96 well plates at densities of $3 \times 10^5$, $7.5 \times 10^4$ and $1.5 \times 10^4$ cells/ml in 50 $\mu$l complete medium and incubated at 37° C. for 24 hours. Subsequently, 100 $\mu$l of select medium containing DMEM medium (Flow, Irvine, UK; without glutamine and ferric nitrate but with sodium pyruvate [110 mg/L]; GIBCO/BRL, Paisley, UK) supplemented with glutamate (60 $\mu$g/ml), asparagine (60 $\mu$g/ml; Sigma, Poole, UK), 1× non-essential amino acids, 7 mg/L of adenosine, cytidine, guanosine and uridine, 2.4 mg/L of thymidine (Sigma, Poole, UK), 10% dialyzed foetal calf serum (APP, Dudley, UK) and 4 $\mu$M MSX (to titrate out the endogenous glutamine synthetase enzyme of YO cells) was added in order to select clones which had integrated the transfected plasmids containing the human antibody genes.

Growth media from COS-1 cells four days post transfection and from YO cells grown in medium for selection of plasmid integration was assayed by a sandwich ELISA assay using flexible microtitre plates (Falcon, Becton-Dickinson, Plymouth, UK) coated with polyclonal anti-human IgG (Sigma, Poole, UK) as capture antibody. The assay sample was added and detection performed with an anti-human γ chain specific peroxidase conjugate (Sigma, Poole, UK) and orthophenylene diamine-HCl (Sigma, Poole, UK) as substrate. Positive clones were transferred to 24 well plates for further propagation in select medium.

Three clones capable of growth in levels of MSX toxic to untransfected YO cells were obtained. Two of these were secreting human antibody, as determined by ELISA assay, whilst the other line appeared to be a false positive.

Example 2

Determination of cynomolgus monkey antibody chain sequences a) Ouchterlony Immunodiffusion An Ouchterlony immunodiffusion test using serum from chimpanzee cynomolgus and aotus monkeys was performed to give an indication of the similarity which might exist between protein sequences of human and primate immunoglobulins.

Micro-ouchterlony plates—supplied by The Binding Site.

Sheep anti-human IgG1, IgG2, IgG3 and IgG4—The Binding Site.

Goat anti-human IgM and Goat anti-human IgA—supplied by Sigma.

Sheep anti-human Ig κ light chain—Serotec.

Sheep anti-human Ig λ light chain—Serotec.

Sera from cynomolgus (old world) monkey, aotus (new world) monkey and chimpanzee (ape) were tested for reaction against a series of anti-human immunoglobulins. The undiluted sheep anti-human antibody (10 μl) was placed in the centre well of an ouchterlony plate and the primate sera (10 μl) placed in the surrounding outer wells. All sera were diluted in PBS according to the manufacturers recommendations. Rabbit and mouse sera were included in the assay as was human serum which acted as a positive control. The plate was incubated at room temperature under humid conditions overnight or until precipitin bands could be visualised.

Precipitin bands were formed between chimpanzee serum and all anti-human sub-classes. Some but not all human Ig classes, namely IgG1, IgM, IgA and κ and λ light chains formed precipitin bands with cynomolgus monkey serum. Aotus monkey serum (a new world monkey) was recognised by the least human antibodies—the only strong reaction was seen with the κ and λ light chains. Surprisingly, the rabbit serum reacted with the anti-human λ light chain—this suggests that there may be a shared epitope between rabbit and human Ig protein sequences for recognition to occur. Mouse serum did not recognise any human Ig classes at all.

This test gave the expected results considering the evolutionary relationship of each species to man—ie. the new world monkeys diverged earlier than the old world monkeys, which show greater protein homology to human. To investigate the degree of nucleotide homology between primate and human Ig genes, the κ light genes from the old world, cynomolgus, monkey were chosen for this study.

b) Cynomolgus monkey total RNA was prepared from 10 mls of peripheral blood lymphocytes using the guanidium thiocyanate method of extraction REF.

First strand cDNA was synthesised from total RNA using the BRL SUPERSCRIPT system (BRL). Total RNA (5 μg) in a volume of 13 μl was added to 1 μl of oligo-dT primer and allowed to anneal by heating at 70° C. for 10 minutes followed by cooling on ice.

First strand cDNA was reverse transcribed by addition of 2 μl reaction buffer, 1 μl dNTPS, 2 μl DTT and 1 μl Reverse transcriptase. The reaction was incubated at room temperature for 10 minutes, followed by 50 minutes at 42° C. The reaction was stopped by heating at 90° C. for 5 minutes, then placing on ice for 10 minutes. The mRNA template was digested with 1 μl of RNase H for 20 minutes at 37° C.

c) PCR Amplification of First Strand cDNA

PCR primers

151—homologous to the 5' end(FR1) of human Vκ1

5' GACATTCAGCTGACCCAGTCTCCA SEQ ID NO:1

301—homologous to the 3' end of human Cκ (contains HindIII restriction site)

5' GATCAAGCTTCTAACACTCTCCCC SEQ ID NO:2

These primers and all subsequent PCR and sequencing primers mentioned were synthesised on an oligodeoxynucleotide synthesiser and were used at a concentration of 200 μg/μl.

First strand cDNA was directly amplified by PCR, without the need for second strand synthesis, using primers 151 and 301. The former is specific for the 5' end of the variable region(FR1) of the human κ1 light chain, and the latter is specific for the 3' end of the constant region of human κ light chain.

The light chain was amplified in the following reaction; the complete first strand cDNA reaction mixture was added to 21 μl dH$_2$O, 8 μl synthesis buffer [(Boehringer)], 4 μl primer 301, 4 μl primer 151 and 0.5 μl Taq polymerase. This mixture was overlaid with mineral oil and subjected to 20 cycles of PGR using the previously mentioned program. The reaction was checked on a 1% agarose gel as before.

d) Cloning of Cynomolgus κ Light Chains

PCR primer 260—homologous to the 5' end of human Vκ (contains Hind III restriction site).

5' GATCAAGCTTGACATTGAGCTGACCCAGTCTCCA SEQ ID NO:3 i. Introduction of Hind III sites at either end of the light chain fragment

The cynomolgus monkey κ light chain cDNA obtained from the previous PCR was cloned in to the HindIII site of pUC18 Maniatis T. et al J.Molecular Cloning (Cold Spring Harbour Laboratory Press 1989). The amplified light chain contains a HindIII site at the 3' end of the constant region due to the sequence of primer 301, but lacks such a restriction site at the 5' end. Therefore, to enable the light chain to be cloned directly into pUC18, a HindIII site was introduced at the 5' end of the variable region by means of a second PCR using primers 260 and 301. The former has an identical sequence to primer 151, but with a HindIII site added on to the 5' end.

The reaction was set up as previously described using 1 μl of cynomolgus cDNA (from PCR mix) in a final volume of 100 μl. The DNA was amplified by 20 cycles of PCR, then checked on a 1% agarose gel. The gel showed many other bands other than those expected for the amplified light chain. It is possible that some of the smaller bands could be due to the primers annealing to each other, forming so-called primer-dimers.

ii) Purification of the PCR product

The light chain was purified from the PCR mixture before cloning in to pUC18, in the following way; the PCR reaction was frozen at −20° C., and the liquid mineral oil aspirated off. The DNA was then extracted twice with phenol/chloroform, followed by a single extraction with chloroform alone. The solution was adjusted to 5 mM EDTA, 10 mM Tris pH8, 0.5% SDS and proteinase K added to 50 μg/ml.

The reaction was incubated at 37° C. for 30 minutes, then 68° C. for 10 minutes. A second phenol/chloroform extraction. The DNA was precipitated by the addition of 1/10 volume 3M sodium acetate and 2.5 volumes of absolute ethanol (1 μl dextran sulphate was added as a carrier). The DNA was placed at −20° C. for 30 minutes, then pelleted in an eppendorf centrifuge. The pellet was washed in 70% ethanol, dried and resuspended in 17 μl water. This purification process overcomes the problem of Taq polymerase remaining bound to the DNA and thus inhibiting restriction enzyme activity.

iii) Preparation of the HindIII fragment for cloning

The light chain DNA was then digested with restriction enzyme HindIII, in order to clone in to the HindIII site of pUC18. To 17 μl of light chain DNA, 2 μl of buffer B and 1 μl of high concentration HindIII was added and incubated at 37° C. for one hour. The digest was separated on a 1% agarose gel and the band corresponding to the light chain was excised from the gel. The DNA was purified from the agarose using "Prep-a-gene" purification kit (Biorad Ltd) following the manufacturers instructions.

e) Ligation of Cynomolgus Light chain in to PUC18

The purified HindIII fragment was cloned in to the HindIII site of pUC18 using the following method; 20 μl of cynomolgus DNA (from a volume of 80 μl) was added to 1 μl of HindIII-digested pUC18 (50 μg/μl Pharmacia), 3 μl ligase buffer (Boehringer), 3 μl T4 DNA ligase (Boehringer) and 3 μl distilled water. The reaction was incubated at 15° C. for 3 hours.

f) Transformation of DH5Competent Cells by pUC18-κ Chain

*E.coli* DH5α maximum efficiency cells (BRL) were transformed with the light chain plasmid. 100 μl of cells were thawed slowly from −70° C., mixed gently with 5 μl ligation reaction and kept on ice for 30 minutes. The cells were incubated at 42° C. for 45 seconds then cooled on ice for 2 minutes. 1 ml of SOC medium (20 g bactotryptone, 5 g yeast extract, 0.5 g NaCl, 10 ml 250 mM KCl, 5 ml 2M MgCl, 20 mM glucose per litre) was added and incubated at 37° C. for 1 hour. The transformation reaction was plated out on to five LB plates (LB agar plates: 12 g tryptone, 24 g yeast extract, 4 ml glycerol, 100 ml phosphate buffer, 15 g bacto-agar per litre) containing 100 μg/ml ampicillin and incubated overnight at 37° C. The number of colonies were counted per plate and the transformation efficiency calculated.

Five colonies were picked from the plates and the presence of light chain inserts checked by PCR. Each colony was resuspended in 65.5 μl distilled water and subjected to 20 cycles of PCR using primers 260 and 301 in the standard reaction mixture. The PCR reactions were run on gel as before. Four out of five colonies were found to contain the insert which indicated that the cloning had been successful.

g) Plasmid Minipreps of PUC18-κChain

Twenty colonies from the five transformation plates were picked and innoculated in to 2 ml volumes of L-Broth (L broth—as LB plates but without agar) containing 100 μg/ml ampicillin. The cultures were incubated at 37° C. overnight with shaking. 1.5 ml of each culture was spun down and the cell pellet resuspended in 200 μl STET—0.1M NaCl, 10 mM Tris HCl pH8, 1 mM EDTA, 5% Triton-X-100) with 1 mg/ml lysozyme. The tubes were incubated for 5 minutes at room temperature then boiled for 45 seconds and centrifuged for 10 minutes. The resulting pellet was removed with a sterile toothpick and 8 μl of 8% CTAB added to the supernatent. The tube was spun for 5 minutes to pellet the plasmid.

DNA which was subsequently resuspended in 300 μl of 1.2M sodium chloride by vortexing. The DNA was precipitated by the addition of 75 μl ethanol, vacuum dried and resuspended in 20 μl of (TE buffer TE—10 mM Tris pH7.4, 1 mM EDTA).

The minipreps were checked for the presence of the light chain by restriction enzyme digestion (HINDIII restriction enzyme and Buffer B-10 u/μl—Boehringer). 2 μl of each DNA was added to 0.5 μl of buffer B, 1 μl of distilled water, 1 μl of RNase A (500 μg/ml Boehringer) and 0.5 μl HindIII. The digests were incubated at 37° C. for 1.5 hours then run on a 1% gel. The presence of the light chain was indicated by a fragment of approximately 700 base pairs.

h) Sequencing of the κ Light Chains

Sequencing primers

M13 Reverse primer—anneals to −ve strand of pUC18, downstream of the polycloning site—supplied by Pharmacia;
5' AACAGCTATGACCATG SEQ ID NO:4

−40 forward primer—anneals to +ve strand of pUC18, downstream of the polycloning site—supplied by USB
5' GTTTTCCCAGTCACGAC SEQ ID NO:5

299—human Cκ region primer
5' GCGTCAGGGTGCTGCTGAGG SEQ ID NO:6

106—human Cκ region primer (5' end)
5' GGCGGGAAGATGAAGACAGA SEQ ID NO:7

151 and 260—see stages C & D

261—human Cκ region primer
5' TTCAGCAGGCACACAACAGA SEQ ID NO:8 i) Ten clones from the previous stage were chosen for sequencing (clones 1,2,4,5,9,12,14,15,18 and 20), by the dideoxy chain termination method. The remaining 18 μl of miniprep DNA was added to 2 μl NaOH(2M) and heated at 68° C. for 20 minutes in order to denature the DNA. The DNA was cooled and precipitated by the addition of 8 μl 5M Ammonium acetate (pH5.4) and 100μ ethanol on dry ice for 5 minutes. The DNA was pelleted, washed in 70% ethanol, vacuum dried and resuspended in 20 μl distilled water.

An aliquot of DNA (7 μl) was added to 2 μl of reaction buffer and 1 μl of the appropriate primer and incubated at 65° C. for 2 minutes, then cooled slowly to below 30° C. to anneal primer and template. It was necessary to use several different primers in order to sequence the entire κ light chains, the details of which are set out above. To the template/primer the following were added; 1 μl DTT (0.1 m USB), 2 μl labeling mix (5× USB), 0.5 μl $^{35}$S-DATP (10 μCi/μl Amersham) and 2 μl Sequenase enzyme. The reaction was incubated at room temperature for 5 minutes in order to synthesise an $^{35}$S-labelled leader sequence. When the labelling reaction was complete, 3.5 μl of labelling mix was added to four wells of a multiwell plate containing 2.5 μl of ddGTP, ddATP, ddTTP and ddCTP. The chain termination reaction was allowed to proceed for 5 minutes at 37° C. before 4 μl of stop solution was added to each well. The reactions were stored on ice until required.

An 8% acylamide gel (ultra-pure acylamide gel mix-8 supplied by BRL) was poured between siliconised glass plates and pre-run at 40 mA for one hour using TBE (0.09M TMS-borate pH8, 0.002M EDTA) as a run buffer. The wells were washed out with buffer before and after the pre-run to remove air bubbles and urea. Before loading the gel, the samples were heated at 95° C. for 2 minutes, then 4 μl of each sample was loaded on to the gel. The samples were run at 40 mA for 1.5 hours, then a second loading applied to the gel and run for another 1.5 hours. This gave a short and long run for each set of samples. The plates were dissembled and the gel placed in 10% acetic acid/10% methanol before transferring the gel to a sheet of 3 MM paper. The gel was dried at 80° C. for 1.5 hours and exposed to X-ray film overnight at room temperature. The autoradiographs were developed and the sequence read from the bottom upwards, with the long and short runs overlapping.

j) Comparison of Sequence Data

The complete light chain sequences of the ten clones were obtained by running a series of sequencing reactions using different primers. Comparisons of sequence data are shown in FIGS. 3(a) and (b) thorough FIG. 6. Clones 14 and 5 were found to contain truncated light chain sequences. This is most likely to be an artifact caused by the reverse transcription of mRNA or the PCR amplification of the cDNA. It may be possible that the mRNA or cDNA formed a secondary structure through which the appropriate enzyme could not read, thus resulting in a partial sequence. Clone 15 was chosen for further comparison with known light chain sequences to confirm its identity and human, rabbit and mouse light chains to determine nucleotide and amino acid homology, the results of which can be seen in Tables 4–7.

The cynomolgus light chain constant region was compared to a human germline Cκ gene (Hieter, P.A. et al Cell 22, 197 (1980)), a mouse MOPC21 Cκ mRNA (Hamlyn, P. A. et al Nucl. Acids Res. 9 4485 (1981) and a rabbit Cκ mRNA (17D9) (McCartney—Francis N. et al Proc. Natl. Acad. Sci. 81 1794, 1984). The cynomolgus variable regions were compared to a human lymphoid cell line, Walker (Klobek, H. G. et al Nucl. Acids Res. 12 6995, 1984). This cell line expresses a light chain gene which belongs to the Vκ1 family and which utilises the J5 gene segment. The 17D9 rabbit sequence was used to compare cynomolgus variable sequences as was the S107A mouse Vκ1 sequence (Kwan, S. P. et al J. Exp. Med. 153, 1366 (1981)). This is a phosphocholine binding IgA κ myeloma which utilises the mouse J1 gene segment. The variable region of clone 15 was also compared to a human antibody, Daudi (Klobek 1984). This light chain gene belongs to the Vκ1 family and uses the J5 gene segment. The cynomolgus antibody κ light chain constant region sequence shows high homology to the human Cκ gene at both the nucleotide (91.6%) and the amino acid (81.3%) levels. Mouse Cκ appeared to be more homologous to either cynomolgus monkey or human Cκ than did rabbit. However, percentage homologies did not appear to differ dramatically when comparing human and monkey to rabbit and mouse or indeed rabbit to mouse.

Tables 5 and 6 show percentage homologies for each framework region and each CDR of clone 15. As expected, the framework regions are relatively conserved between species compared to CDRs where there is considerable variability. For example, clone 15 shares 90–96% amino acid sequence homology with human in frameworks 1 and 3 but only 22% homology within CDR 3. Clone 15 shows a high degree of homology to both Walker and Daudi human light chain sequences especially within frameworks 1 and 3, although exhibits a higher homology to Walker than Daudi. The rabbit Vκ sequence shows more homology to both human and monkey sequences than does mouse. This could explain why some reaction to anti-human antibodies was seen with rabbit serum in the ouchterlony test but no reaction was seen with mouse serum.

TABLE 4

Comparisons of light chain constant region sequence homologies

| Species | % homology DNA | % homology AA |
|---|---|---|
| Cynomlogus/human | 91.6 | 81.3 |
| Cynomlogus/rabbit | 66.0 | 51.0 |
| Cynomlogus/mouse | 68.0 | 58.0 |
| Human/rabbit | 65.7 | 45.8 |
| Human/mouse | 69.8 | 58.9 |
| Rabbit/mouse | 63.0 | 49.5 |

TABLE 5

Percentage homologies of light chain framework and CDR DNA sequences

| | Cyno 15 v | | | |
|---|---|---|---|---|
| | Human W | Human D | Rabbit | Mouse |
| FR 1 | 89.9 | 89.9 | 71.0 | 66.7 |
| CDR1 | 84.8 | 66.7 | 60.6 | 42.4 |
| FR 2 | 95.6 | 80.0 | 86.7 | 75.6 |
| CDR2 | 80.0 | 60.0 | 60.0 | 50.0 |
| FR 3 | 92.6 | 91.6 | 82.1 | 76.8 |
| CDR3 | 50.0 | 61.5 | 26.9 | 57.7 |
| FR 4 | 75.8 | 75.8 | 66.7 | 66.7 |

TABLE 6

Percentage homologies of light chain framework and CDR amino acid sequences

| | Cyno 15 v | | | |
|---|---|---|---|---|
| | Human W | Human D | Rabbit | Mouse |
| FR 1 | 95.7 | 95.7 | 52.2 | 47.8 |
| CDR1 | 72.7 | 27.3 | 36.4 | 36.4 |
| FR 2 | 73.3 | 86.7 | 66.7 | 60.0 |
| CDR2 | 71.4 | 42.9 | 71.4 | 28.6 |
| FR 3 | 90.6 | 96.9 | 78.1 | 78.1 |
| CDR3 | 22.2 | 22.2 | 0.0 | 33.3 |
| FR 4 | 80.0 | 70.0 | 60.0 | 70.0 |

We claim:

1. A process for the production of a recombinant primate antibody comprising:
   (i) selecting a primate lymphocyte-derived cell line that is capable of expressing a desired antibody;
   (ii) isolating RNA from the cell line and separating mRNA from the other RNAs so isolated;
   (iii) synthesising cDNA from the mRNA and inserting the cDNA into a cloning vector;
   (iv) transforming a host cell with the vector containing the cDNA to obtain a library;
   (v) screening the library for cDNA encoding the entire constant and variable regions of the heavy and light chains;
   (vi) inserting the cDNA encoding the heavy and light chains into an expression vector;
   (vii) transfecting a host cell with the expression vector containing the cDNA; and
   (viii) culturing the transfected host cell and isolating the desired antibody.

2. A process as claimed in claim 1 wherein the primate is a human.

3. A process as claimed in claim 1 wherein the primate is a chimpanzee or an old world monkey.

4. A process as claimed in claim 1 wherein the cell-line is produced from lymphocytes from an individual known to have recovered or be in remission from a disease state.

5. A process as claimed in claim 1 wherein the cell-line is produced from lymphocytes from an individual known to be infected with a pathogenic organism or is suffering from cancer or an autoimmune disease, but who does not manifest full disease symptoms.

6. A process as claimed in claims 4 or 5 wherein the individual has been infected by a virus.

7. A process as claimed in claim 1 wherein the cell-line is produced from lymphocytes from an individual who has been vaccinated or innoculated with antigen and has mounted an antibody response.

8. A process as claimed in claim 1 wherein the cell-line is stabilised or immortalised.

9. A process as claimed claim 1 wherein the cell-line is selected by screening for production of antibody with affinity for a desired antigen.

10. A process as claimed in claim 9 wherein the cell-line is further selected by screening for antibody funtionality.

11. A process for the production of a recombinant antibody comprising:
   i) micro-RNA preparation from approximately 1000 cells;
   ii) generation of a size-selected cDNA library;
   iii) screening the library for cDNA encoding the entire constant and variable regions of the antibody and light chains and isolating the same;
   iv) inserting the cDNA encoding the heavy and light chains into an expression vector;

v) transfecting a host cell with the expression vector containing the cDNA; and vi) culturing the transfected host cell and isolating the desired antibody.

12. A vector suitable for transfection of a host cell comprising cDNA encoding primate antibody heavy and light chains.

13. A eukaryotic cell-line transfected with cDNA for the expression of primate antibody heavy and light chains.

14. A process for the expression of cDNA encoding primate antibody heavy and light chains, comprising transfecting a eukaryotic host cell with a vector or vectors suitable for the expression of said cDNA.

* * * * *

(12) EX PARTE REEXAMINATION CERTIFICATE (8065th)
United States Patent
Crowe et al.

(10) Number: US 5,876,961 C1
(45) Certificate Issued: Mar. 8, 2011

(54) PRODUCTION OF ANTIBODIES

(75) Inventors: James Scott Crowe, Beckenham (GB);
Alan Peter Lewis, Beckenham (GB)

(73) Assignee: Burroughs Wellcome Co., Research Triangle Park, NC (US)

Reexamination Request:
No. 90/006,997, Apr. 5, 2004

Reexamination Certificate for:
Patent No.: 5,876,961
Issued: Mar. 2, 1999
Appl. No.: 08/378,939
Filed: Jan. 26, 1995

Related U.S. Application Data

(63) Continuation of application No. 07/952,640, filed on Dec. 1, 1992, now abandoned, which is a continuation of application No. PCT/GB92/01282, filed on Jul. 14, 1992.

(30) Foreign Application Priority Data

| Jul. 15, 1991 | (GB) | ............................. 9115284 |
| Mar. 23, 1992 | (GB) | ............................. 9206284 |
| Aug. 1, 1994 | (GB) | ............................. 9116594 |

(51) Int. Cl.
*C07K 16/08* (2006.01)
*C07K 16/00* (2006.01)
*C07K 16/10* (2006.01)

(52) U.S. Cl. .................... 435/69.1; 435/320.1; 435/332; 435/252.3; 435/339; 435/326; 435/69.6

(58) Field of Classification Search .................. None
See application file for complete search history.

(56) References Cited

U.S. PATENT DOCUMENTS

| 4,205,126 A | | 5/1980 | Cartaya | |
| 4,608,337 A | * | 8/1986 | Croce ....................... | 435/70.21 |
| 4,657,866 A | | 4/1987 | Kumar | |
| 4,735,210 A | * | 4/1988 | Goldenberg ............... | 424/1.29 |
| 4,767,704 A | | 8/1988 | Cleveland | |
| 4,929,706 A | | 5/1990 | Heifetz et al. | |
| 5,001,065 A | * | 3/1991 | Larrick et al. ............... | 435/7.1 |
| 5,045,468 A | | 9/1991 | Darfler | |
| 5,063,157 A | | 11/1991 | Stockinger | |
| 5,122,469 A | * | 6/1992 | Mather et al. ............... | 435/383 |
| 5,135,866 A | | 8/1992 | Heifetz et al. | |
| 5,149,635 A | * | 9/1992 | Gillies ....................... | 435/69.1 |
| 5,316,938 A | | 5/1994 | Keen et al. | |
| 5,484,886 A | * | 1/1996 | Fong et al. ................... | 530/350 |
| 5,545,403 A | | 8/1996 | Page et al. | |
| 5,545,405 A | | 8/1996 | Page et al. | |
| 5,545,504 A | | 8/1996 | Keoshkerian et al. | |
| 5,608,337 A | * | 3/1997 | Hendricks et al. ........... | 324/765 |
| 5,633,162 A | | 5/1997 | Keen et al. | |
| 5,807,715 A | | 9/1998 | Morrison et al. ........... | 435/69.6 |
| 5,846,534 A | | 12/1998 | Waldmann et al. | |
| 5,876,961 A | | 3/1999 | Crowe et al. | |
| 6,291,158 B1 | * | 9/2001 | Winter et al. .................. | 435/6 |
| 2003/0035799 A1 | | 2/2003 | Page et al. | |
| 2004/0228857 A1 | | 11/2004 | Page et al. | |

FOREIGN PATENT DOCUMENTS

| EP | 0239400 | 9/1987 |
| EP | 0274394 | 7/1988 |
| EP | 0307247 | 3/1989 |
| EP | 0314161 | 5/1989 |
| EP | 0316068 | 5/1989 |
| EP | 0325190 | 7/1989 |
| EP | 0328404 | 8/1989 |
| EP | 0388151 | 3/1990 |
| EP | 0363703 | 4/1990 |
| EP | 0388151 | 9/1990 |
| EP | 0389786 | 10/1990 |
| EP | 0390327 | 10/1990 |
| EP | 0404003 | 12/1990 |
| EP | 0610447 | 4/1993 |
| FR | 2543158 | 9/1984 |
| GB | 2196348 | 4/1988 |
| JP | 61025480 | 7/1984 |
| JP | S63-7780 | 1/1988 |
| WO | WO 87/01131 | 2/1987 |
| WO | WO 88/00967 | 2/1988 |
| WO | WO 89/00999 | 2/1989 |
| WO | WO 89/01783 | 3/1989 |
| WO | WO 91/04336 | 4/1991 |
| WO | WO 91/10722 | 7/1991 |
| WO | WO 92/07084 | 4/1992 |
| WO | WO 93/02108 | 2/1993 |
| WO | WO 93/07899 | 4/1993 |

OTHER PUBLICATIONS

Larrick et al. Biochem. Biphys. Res. Commun. 160: 1250–1256 (1989).*

Larrick et al. Biochem Biophys. Res. Commun. 160: 1250 1256 (1989).*

Van Meurs et al. J. Immunol. Methods 95: 123–128 (1986).*

Veronica Ebert Doctoral Thesis, "Expression of Antibody c–DNA in CHO (Chinese Hamster Ovary) Cells" (1991); original copy in German and translation in to English.

Bebbington "Expression of antibody genes in nonlymphoid mammalian cells" Methods: A Companion to Meth. Enzymol. 2:136–145 (1991).

(Continued)

*Primary Examiner*—Padmashri Ponnaluri

(57) ABSTRACT

This invention relates to the preparation of recombinant primate antibodies by DNA technology; Micro-RNA techniques for production of the same; recombinant non-human primate antibodies; formulations containing the same; the use of such antibodies in the prophylaxis and treatment of humans, and diagnostic uses of such antibodies.

At the time of issuance and publication of this certificate, the patent remains subject to pending reissue application number 11/289,714 filed Nov. 29, 2005. The claim content of the patent may be subsequently revised if a reissue patent is issued from the reissue application.

OTHER PUBLICATIONS

Bebbington et al. "High–level expression of a recombinant antibody from myeloma cells using a glutamine synthetase gene as an amplifiable selectable marker" Biotechnol. 10:169–175 (1992).

Carter et al. "Humanization of an anti–p185$^{HER2}$ antibody for human cancer therapy" Proc. Natl. Acad. Sci. USA 89:4285–4289 (1992).

Colcher et al. "Characterization and biodistribution of recombinant and recombinant/chimeric constructs of monoclonal antibody B72.3" Cancer Res. 49:1738–1745 (1989).

De Waele et al. "Expression in non–lymphoid cells of mouse recombinant immunoglobulin directed against the tumour marker human placental alkaline phosphatase" Eur. J. Biochem. 176:287–295 (1988).

Ehrlich et al. "Potential of primate monoclonal antibodies to substitute for human antibodies: Nucleotide sequence of chimpanzee Fab fragments" Hum. Antibod. Hybridomas 1:23–26 (1990).

Ehrlich et al. "Nucleotide sequence of chimpanzee $F_c$ and hinge regions" Mol. Immunol. 28:319–322 (1991).

Feys et al. "Expression of functional mouse antibodies directed against the tumour marker human plancental alkaline phosphatase in non–lymphoid cells" Intl. J. Cancer Suppl. 2:26–27 (1988).

Fouser et al. "High level expression of a chimeric anti–ganglioside GD2 antibody: Genomic kappa sequences improve expression in COS and CHO cells" Biotechnol. 10:1121–1127 (1992).

Gillies et al. "Expression of human anti–tetanus toxoid antibody in transfected murine myeloma cells" Biotechnol. 7:799–804 (1989).

Gillies et al. "High–level expression of chimeric antibodies using adapted cDNA variable region cassettes" J. Immunol. Meth. 125:191–202 (1989).

King et al. "Expression, purification and characterization of a mouse–human chimeric antibody and chimeric Fab fragment" Biochem. J. 281:317–323 (1992).

Knight et al. "Stable expression of cloned human antibody genes in murine myeloma cells" Hum. Antibod. Hybridomas 3:129–136 (1992).

Larrick et al. "Polymerase chain reaction using mixed primers: Cloning of human monoclonal antibody variable region genes from single hybridomas cells" Biotechnol. 7:934–938 (1989).

Levy et al. "A rapid method for cloning and sequencing variable–region genes of exposed immunoglobulins" Gene 54:167–173 (1987).

Lewis et al. "Rescue and expression of human immunoglobin genes to generate functional human monoclonal antibodies" Hum. Antibod. Hybrid. 3;146–152 (1992).

Liu et al. "Production of a mouse–human chimeric monoclonal antibody to CD20 with potent Fc–dependent biologic activity" J. Immunol. 13:3521–3528 (1987).

Liu et al. "Chimeric mouse–human IgG1 antibody that can mediate lysis of cancer cells" Proc. Natl. Acad. Sci. USA 84:3439–3443 (1987).

Liu et al. "Expression of mouse::human immunoglobulin heavy–chain cDNA in lymphoid cells" Gene 54:33–40 (1987).

Morrison et al. "Chimeric human antibody molecules: Mouse antigen–binding domains with human constant region domains" Proc. Natl. Acad. Sci. USA 81:6851–6855 (1984).

Mountain et al. "Engineering antibodies for therapy" Biotechnol. Genet. Eng. Rev. 10:1–142 (1992).

Neuberger et al. "The intron requirement for immunoglobulin gene expression is dependent upon the promoter" Nucl. Acids Res. 16:6713–6724 (1988).

Newman et al. "Primatization of recombinant antibodies for immunotherapy of human diseases: A macaque/human chimeric antibody against human CD4" Biotechnol. 10:1455–1460 (1992).

Page et al. "High level expression of the humanized monoclonal antibody Campath–1H in Chinese hamster ovary cells" Biotechnol. 9:64–68 (1991).

Persson et al. "Generation of diverse high–affinity human monoclonal antibodies by repertoire cloning" Proc. Natl. Acad. Sci. USA 88:2432–2436 (1991).

Robinson et al. "Chimeric mouse–human anti–carcinoma antibodies that mediate different anti–tumor cell biological activities" Hum. Antibod. Hybridomas 2:84–93 (1991).

Rose et al. "A chimeric mouse/human anti–IL–2 receptor antibody with enhanced biological activities" Mol. Immunol. 29:131–144 (1992).

Ruker et al. "Expression of a human monoclonal anti–HIV–1 antibodies in CHO cells" Ann. N.Y. Acad. Sci. pp. 212–219 (1991).

Sambrook et al. Molecular Cloning: A laboratory Manual, $2^{nd}$ Ed. pp. 8.8–8.9 and 14.15 ((1989).

Weidle et al. "Expression of antibody cDNA in murine myeloma cells: Possible involvement of additional regulatory elements in transcription of immunoglobulin genes" Gene 60:205–216 (1987).

Weidle et al. "Reconstitution of functionally active antibody directed against creatine kinase from separately expressed heavy and light chains in non–lymphoid cells" Gene 51:21–29 (1987).

Whittle et al. "Expression in COS cells of a mouse–human chimaeric B72.3 antibody" Protein Eng. 1:499–505 (1987).

Wood et al. "High level synthesis of immunoglobulins in Chinese hamster ovary cells" J. Immunol. 145:3011–3016 (1990).

Ebert "Expression von Antikörper c–DNA in CHO (Chinese Hamster Ovary)–Zellen" Dissertation Thesis (German).

English translation on the Ebert "Expression of Antibody c–DNA in CHO (Chinese Hamster Ovary) Cells" Dissertation Thesis.

Letter from Boku Head Librarian concerning the Dissertation Thesis of Ebert (German) dated Jun. 10, 2003.

English translation of the letter from Boku Head Librarian dated Jun. 10, 2003.

1990 GIBCO BRL Catalogue & Refernce Guide.

Anthony Lubinieki, ESACT 9th Meeting, Editors Spier R.E. et al., (1989) pp. 85–92.

Hale et al.,. *Transplantation*, (1988) 45:753–759.

Ham, *Proceedings of the National Academy of Sciences*, (1965) 53:288–293 [composition of F12 attached].

Iscove and Melchers, *The Journal of Experimental Medicine*, (1978)147: 923–933.

Kyle et al., *Journal of Rheumatology*, (1991)18 (11):1737–1738.

Luff, cited in "*The BSE Inquiry*," established for the British Government.

Mendiaz et al., *In Vitro Cell .Dev. Biol.*, (1986)22: 66–74.

Merten et al., *Production of biologicals from animal cells in culture research, development, and achievements, $10^{th}$ Mtg.*, Avignon, France (1990).

Mountain and Adair, *Biotechnology and Genetic Engineering Reviews*, (1992)10:1–142.
Murphy, *Science* (1996)273(5276):746–747 Exhibit L.
Nippon Zenyaku Industries, Reply of Applicant concerning EP92306420.8, May 28, 1998.
Organic Chemistry, John Wiley & Sons Inc, vol. II Second Edition pp. 1129–1130 and 1136–1138 (1943) Exhibit C.
Phillpotts, *Cytotechnology*, (1989)2:161–162.
R.H. Kimberlin, *Symposium of Virological Aspects of the Safety of Biological Products* London, England 1990, Develop. Biol. Standard, (1991)75:75–82.
Rabbi S. Emanuel, MK Vaad, *Hair*, (2003) vol. IV (7) 9 <www.mk.ca/page6_11.php>.
Regenstein et al., E–Journal <www.Kashrut.com>, Kosher Issues for Today's Dairy Industry, 2002.
Riechmann et al., *Nature*, vol. 322 pp. 323–327 (1988).
Robinson et al., *Human Antibody Hybridomas*, (1991)2:84–92.
Saban, T., (2004) "Food Additives From Islamic Perspective," Version 1.3 <wwwsrv1.mycity.at/privat.9704236/lm/LM–en.html> Exhibit F.
Sano et al., *Cell Structure and Function*, (1988)13(2):143–159.
Sigma–Aldrich Company Search Criteria/Results, <www.sigma–aldrich.com>.
Spira et al., *Trends in Animal Cell Culture Technology*, Proc. Ann. Meeting Jpn. Tech., (1990): 67–73 [Reporting conference meeting in 1989].
Titeux et al., *Journal of Cellular Physiology*, (1984): 121:251–256.
Ungemach et al., The 50th Meeting of the joint FAO/WHO Expert Committee on Food Additives (JECFA), World Health Organization, 1998 Exhibit K.
Whitaker et al., *Biopharm*, (Sep. 1990)3(8):5.
Whittle et al., *Protein Eng.*, (1987)1:499–505.
Wiebe, et al., ESACT 9$^{th}$ Meeting, Editors Spier R.E. et al., (1989):68–71.
Zettlemeissl et al., *Biotechnology*, (1987)5:720–725.
U.S. Appl. No. 10/145,712, filed May 2002, Page, et al.
U.S. Appl. No. 10/145,992, filed May 2002, Page, et al.
U.S. Appl. No. 10/765,067, filed Jan. 2004, Page, et al.
REI U.S. Appl. No. 10/955,040, filed Nov. 2004, Keen, et al.
REX 90/006,656, Jun. 2003, Keen, et al.
1990 GIBCO BRL Catalogue & Refernce Guide (confirmation of availability attached).
Abstract of the USPTO trademark database regarding the trademark for NUCELLIN of Eli Lilly.
Ahmed, S. (2001) "Eating Human Hair by Another Name," <www.albalagh.net/halal/col2.shtml.
Anthony Lubinieki, ESACT 9$^{th}$ Meeting, Editors Spier R.E. et al., (1989) pp. 85–92.
Bebbington, et al., Biotechnology, (1992) 10:169–175.
Bebbington et al., Methods: A companion to Methods in Enzymology, (*Abstract*) (1991)2(2):136–145.
Blech, Z., reprinted with permission from *MK News and Views*, vol. IV (6) 2003.
Brown et al., Emerging Infectious Diseases, (2001)7 (1):6–16.
C6852, *Biochemicals and Reagents for Life Science Research*, p. 600 (2002–2003) Sigma–Aldrich Company (Current website information also included).
C7880, *Biochemicals and Reagents for Life Science Research*, p. 600 (2002–2003) Sigma–Aldrich Company (Current website information also included).
C8530, *Biochemicals and Reagents for Life Science Research*, p. 508 (2002–2003) Sigma–Aldrich Company (Current website information also included).
Carter et al., PNAS, (May 1992) 89:4285–4289.
Colcher et al., Cancer Research, (1989) 49:1738–1745.
Dafler, F., *In Vitro Cell Dev. Bio.*, (1990)26:769–778.
Darfler, *In Vitro Cell. Dev. Bio.*, (1990) 26: 779–783.
DeWaele et al., *European Journal of Biochemistry*, (1988)176 (2–3):287–295.
Dickman, *Nature*, (1987) 329:93.
Dulbecco and Freeman, *Virology*, (1959) 8: 396–397 [composition of DMEM attached].
Dyer et al., *Blood*, (1989) 73:1431–1439.
Eagle, *Science*, (1959), 130:432–437 [composition of MEM attached].
Ebert, Expression of Antibody C–DNA in CHO ("Chinese hamstet ovary") Cells, Dissertation Completed at the *Institute for Applied Microbiology University for Soil Cultivation*, Feb. 1991 (with Translation).
Ehrlich et al., *Human Antibod. Hybridomas*, (1990)1(1):23–26.
Ehrlich et al, *Molecular Immunology*, (1991) 28(4–5): 319–322.
Feldman, G., (Oct. 2001). "Amino Acid Production and the Associated Theoretical Risk of BSE Transmission from their Use in the Production of Biologicals, Drugs, and Medical Devices," *FDA TSA Advisory Committee Meeting* <www.fda.gov/Ohrms/dockets/ac/01/slides/.
Feys et al., *International Journal of Cancer*, (1988)2:26–27.
Feys, et al., *Chemical Abstracts*, (1988)108(23):514.
Fouser, et al., Biotechnology, (1992)10:1121–1127.
Freshney, *Culture of Animal Cells*, Second Ed., Wiley–Liss (1989)70–84.
Gardner–Lane et al, Decision on Preliminary Motions, *Glaxo Welcome Inc.* v. *Cabilly et al*, 2002.
Gasser et al., *In Vitro Cellular Development Biology*, (1985)21(10):588–592.
Gillies et al., *Biotechnology*, (1989) 7:799–804.
Gillies et al., *J Imminological Methods*, (1989) 125:191–202.
Goeddel et al., *Proceedings of the National Academy of Sciences USA*, vol. 76 (1) pp. 106–110 (1979).
Hale et al., *Journal of Immunological Methods*, (1987) 103:59–67.
Hale et al., *Mol. Biol. Med.*, (1983)1:305–319.
Hale et al. *The Lancet*, (1988)2:1394–1399.
Hale et al., *Tissue Antigens*, (1990) 35:118–127.
Hale et al., *Transplantation*, (1988)45:753–759.
Ham, *Proceedings of the National Academy of Sciences*, (1965) 53:288–293 [composition of F12 attached].
Hamilton et al., *In Vitro*, vol. 13 (9) pga 537–547 (1977).
Handa–Corrigan et al., *Enzyme Microbial Technology*, vol. 11, pp. 230–235 (1989).
Higuchi, K., *Advances Applied Microbiology*, (1973)16:111–136.
Holtta et al., *Biochemica et Biophysica Acta*, (1982)721:321–327.
I5500, *Biochemicals and Reagents for Life Science Research*, p. 1147 (2002–2003) Sigma–Aldrich Company (Current website information also included).
Isaacs et al., The Lancet, vol. 340 (1992)8822:748–752.
Iscove and Melchers, *The Journal of Experimental Medicine*, (1978)147:923–933.
K. Loren, *Vibrant Life*, (1999)2 (1) 13.

Kaqawa et al., *Journal of Biochemistry*, (1970)68:133–136.
Katsua & Takaoka, *Methods of Cell Biology*, (1973) 6: 1–42.
Kaufman et al., Molec. Cell Biol., (1985)5(7):1750–1759.
Keay, *Biotechnology and Bioengineering*, (1976)vol. XVIII pp. 363–382.
King et al, *Biochem Journal*, (1992) 281:317–323.
Knight et al., *Human Antibody Hybridomas*, (1992)3:129–136.
Köhrle, J., *Biochimie*, (1999)81:527–533.
Kyle et al., *Journal of Rheumatology*, (1991)18(11):1737–1738.
Larrick, et al., *Biotechnology*, (1989)7 :934–938.
Levy et al., *Gene*, (1987)54: 167–173.
Lewis et al., *Human Antibody Hybridomas*, (1992) 3:146–152.
Liu, et al., *Gene*, (1987)54(1): 33–40.
Liu et al., *J. Immunology*, (1987)13(10):3521–3528.
Liu, et al., *PNAS*, (1987) 84(10): 3439–3433.
Luff, cited in "The BSE Inquiry," established for the British Government.
Marquis et al., *Cytotechnology* (1989)2:163–170.
McCormick et al., *Molecular Cell Biol.*, (1984)4(1):166–172.
McKeehan et al., *Proceedings of the National Academy of Sciences USA*, (1976)73:2023–2027.
Mendiaz et al., *In Vitro Cell. Dev. Biol.*, (1986)22: 66–74.
Merten et al., *Production of biologicals from animal cells in culture research, development, and achievements, 10th Mtg.*, Avignon, France (1990).
Morrison et al., *PNAS*, (1984) 81: 6851–6855.
Mountain and Adair, *Biotechnology and Genetic Engineering Reviews*, (1992)10:1–142.
Murphy, *Science*, (1996)273(5276):746–747.
Nakamori et al., *Applied and Environmental Microbiology*, (1998) 64(5):1607–1611.
Neuberger et al., *Nucleic Acids Research*, (1988)16(14): 6713–6724.
Newman, et al., *Biotechnology*, (1992)10:1455–1460.
Nippon Zenyaku Industries, *Reply of Applicant concerning EP92306420.8*, May 28, 1998.
Noda et al., *Chem. Abs.*, (1988)110 (19) Abstract:652.
Ogata et al., *Applied Mcrobiology Biotechnology*, (1993) 38(4): 520–525.
Oka et al., Bioprogress Technol., (1990)10:72–92.
*Organic Chemistry*, John Wiley & Sons Inc, vol. II Second Edition pp. 1129–1130 and 1136–1138 (1943).
Page and Sydenham, *Biotechnology*, (1991)9: 64–68.
Persson et al. *PNAS*, (1991) 88:2432–2436.
Phillpotts, *Cytotechnology*, (1989)2:161–162.
R.H. Kimberlin, Symposium of Virological Aspects of the Safety of Biological Products London, England 1990, *Develop. Biol. Standard*, (1991)75:75–82.
Rabbi S. Emanuel, MK Vaad Hair, (2003) vol. IV (7) 9 <www.mk.ca/page6_11.php>.
Regenstein et al., E–Journal, Kosher Issues for Today's Dairy Industry, 2002.
Riechmann et al., *Nature*, vol. 322, pp. 323–327 (1988).
Robinson et al., *Human Antibody Hybridomas*, (1991)2: 84–92.
Rose et al., *Molecular Immunology*, (1992) 29(1):131–144.
Rüker, et al., *Annals New York Acad. Sci.*, (1991): 212–219.
Saban, T., (2004) "Food Additives From Islamic Perspective," Version 1.3 <wwwsrv1.mycity.at/privat.9704236/IM/LM–en.html>.
Salahuddin et al., *Journal of Experimental Medicine*, vol. 155 pp. 1842–1857 (1982).
Sambrook et al., *Molecular Cloning: A Laboratory Manual*, Second Edition (1989):8.8–8.9.
Sano et al., *Cell Structure and Function*, (1988)13(2):143–159.
Scahill et al., *Proceedings of the National Academy of Sciences*, 80:4654–4658.
Schneider & Laviox, *Journal of Immunological Methods*, (1990)129:251–268.
Schneider, *Journal of Immunological Methods*, (1989) 116: 65–77.
Sigma–Aldrich Company Search Criteria/Results, <www.sigma–aldrich.com>.
Spira et al. *Trends in Animal Cell Culture Technology, Proc. Ann. Meeting Jpn. Tech.*, (1990): 67–73 к[Reporting conference meeting in 1989].
Taylor et al., *Mutation Research*, (1979) 67:65–80.
Titeux et al., *Journal of Cellular Physiology*, (1984):121:251–256.
Tsujimoto et al., *Journal of Biochemistry*, (1989) 106:23–28.
Ungemach et al., *The 50th Meeting of the joint FAO/WHO Expert Committee on Food Additives (JECFA)*, World Health Organization, 1998.
Urblan & Chasin, *Proceedings of the National Academy of Sciences*, (1980)77(7):4216–4220.
Weber et al., Journal of Neuroimmunology, (1989) 22:1–9.
Weidle et al., *Gene*, (1987)51: 21–29.
Weidle et al., *Gene*, (1987)60: 205–216 (1987).
Whitaker et al., *Biopharm*, (Sep. 1990)3(8):5.
Whittle et al., *Protein Eng.*, (1987)1:499–505.
Wiebe, et al., ESACT 9th Meeting, Editors Spier R.E. et al., (1989):68–71.
Wood, et al., *Journal of Immunology*, (1990)145: 3011–3016.
Yang et al., *Proceedings of the National Academy of Sciences USA*, (1984) 81:2752–2756.
Zekauskas et al., *J Okla. State Med. Assoc.* (1990)83:447–448.
Zettlemeissl et al., *Biotechnology*, (1987)5:720–725.
Moellering, et al., "Electrophoretic Differences in Mab Expressed in Three Media." *BioPharm.* Feb. (1990) 30–38.
DiAugustine, et al. "Evidence of Isoaspartyl (Deamidated) Forms of Mouse Epidermal growth Factor." *Anal. Biochem.* (1987) 165(2):420–429.
Cini, et al., "Molecular Basis for the Isozymes of Bovine Glucose–6–Phosphate Isomerase," *Arch Biochem. Biophys.* 263(1) 96–106.
Wingfield, et al. "Purification and Characterization of Human Interleukin–1a Produced in *Escherichia coli.*" *Eur. J. BioChem.* (1987) 165(3) 537–541.
Teshima G., et al., "Deamidation of soluble CD4 at asparagine–52 results in reduced binding capacity for the HIV–1 envelope glycoprotein gp120," *Biochemistry* (1991) 30(16):3916–22.
Kalwy, S., et al., "Toward More Efficient Protein Expression," *Molecular Biotechnology* (2006) vol. 34 p. 151.
92 306 420.8 –2401/523949, Apr. 26, 2007, EP—Interlocutory decision in Opposition for EP0523949.
Huang and Gorman, "The Simian Virus 40 Small–t Intron, Present in Many Common Expression Vectors, Lead to Aberrant Splicing," *Molecular and Cellular Biology* (1990) 10(4):1805–1810.

Schneider, et al. "Hybrid Immunoglobulin Isotypes of Identical Specificity Produced by Genetic Recombination in *Escherichia coli* and Expression in Lymphoid Cells," *Proteins: Structure, Function and Genetics* (1987) 81–89 (1987).

Morrison, "Transfection Provide Novel Chimeric Antibodies," *Science* (1985) 229:1202–1205.

Jungbauer, et al. "Pilot scale production of a human monoclonal antibody against human immunodeficiency virus HIV–1," *Journal of Biological and Biophysical Methods.* (1989) 19:223–240.

Miyazaki, et al. "Production of Monoclonal antibodies against human erythropoietin and their use in the purification of human urinary erythropoietin" *J. Immunol. Methods.* (1988) Oct. 26:113(2)261–7 Abstract.

Lipoldova, "T–cell receptor V beta 5 usage defines reactivity to a human T–cell receptor monoclonal antibody," *Immunogenetics* (1989) 30(3):162–8—abstract.

Felgenhauer, et al. "Nucleotide sequences of the cDNAs encoding the V–regions of H– and L–chains fo a human moncalonal antibody specific to HIV–1–gp41," *Nucleic Acids Research* (1990) 18(16) 4927.

Alsmadi et al. "Antibody–Dependent Cellular Cytotoxicity Directed against Cells Expressing Human Immunodeficiency Virus Type 1 Envelope of Primary or Laboratory–Adapted Strains by Human and Chimpanzee Monoclonal Antibodies of Different Epitope Specificities", *Journal of Virology*, 72(1):286–293 (1998).

Forthal et al., "Antibody from Patients with Acute Human Immunodeficiency Virus (HIV) Infection Inhibitis Primary Strains of HIV in the presence of Natural–Killer Effector Cells", *Journal of Virology*, 75(15):6953–6961 (2001).

English translation of Dissertation of Veronica Ebert Experssion of Antibody c–DNA in CHO (Chinese Hamster Ovary) Cells University for Soil Conversation, Vienna Austria (1991).

Letter from head librarian of Boku submitted in Opposition of EP0523949.

Letter from head librarian to "whom it may concern" submitted in Opposition of EP0523949.

Declaration of Dr. J. Adair submitted in Opposition of EP0523949.

Alfred Hahn's CV submitted in Opposition of EP0523949.

Email of Jan. 11, 2007 from Ingrid Haas submitted in Opposition of EP0523949.

Expert declaration of Dr. Florian Ruker submitted in Opposition of EP0523949.

Waldman, et al. "A Clonal Derivative of Tunicamysin–Resistant Chinerse Hamster Ovary Cells with Increased N–Acetylglucosamine–Phosphate Transferase Activity Has Altered Asparagine–Linked Glycosylation" *J. cell. Physio.* 131 pp. 302–317 (1987).

Handa–Corrigan et al. *Animal cell Technology: Developments and Products* (1991).

Roberts, et al. *J. cell Biochem* 20th Annual Meeting p. 122 (1991).

Roitt Brostoff and Male. Immunology 6th Edition, p. 74 (2001).

Jefferis. "Structure Function Relationships in Human Immunoglobulins" *Neth J Med* (1991).

Patel, et al. "Different culture methods lead to differences in murine IgG monoclonal antibody" *Biochem J.* 285, 839–845 (1992).

Kunert, et al. "Molecular Characteristics of Five Neutralizinf Anti–HIV Type I Antibodies: Indentification on Nonconventional D. Segments in the Human Monoclonal Antibodies 2G12 and 2F5" *Aids Research* 14(3):1115–1128 (1998).

Bartholomew, et al. "Functional analysis of the effects of a fully humanized anti–Cd4 antibody on resting and activated human T cells" *Immunoololguy* 85:41–48 (1995).

Sims, et al. "A Humanized CD18 Antibdoy can Block Function without Cell Destruction" *J. Immumol.* 151:2296–2309 (1993).

Gorman, et al., *PNAS* 88 (1991), 4181–4185.

Bulens, et al., *Eur. J. Biochem.* 195 (1991) 235–242.

*Monoclonal Antibodies*, Mar. 10–16, 1991, p. 122.

Peakman, et al., *Hum. Antibod. Hybridomas.* 5 (1994) 65–74.

Darfler, et al., *In Vitro Cell Dev. Biol.* 26: 769–778 (1990).

Phillips, et al., *Cytotherapy* (2001) 3(3):233–242.

Nishimura, et al., *Cancer Research* (1987) 47:999–1005.

Neumaier, et al., *Cancer Research*, (1990) 50:2128–2134.

Adair, et al., Proc. 1988 BiofairConference Tokyo (1988) 239–244.

Owens, et al., *Animal Cell Technology: Development & Pro* (1991).

Curling, et al., *BioChem. J.* (1990) 272:333–337.

Zettimeissl, et al., "Characterization of Recombinant Human Antithrombin III Synthesized in Chinese Hamster Ovary Cells", *The Journal of Biological Chemistry*, 264(35):21153–211159 (1989).

Michel, et al., "Synthesis in Animal Cells of Hepatitis B Surface Antigen Particles Carrying a Receptor for Polymerzied Human Serum Albumin", *Proc. Natl. Acad. Sci. USA*, 81:7708–7712 (1984).

Colomb, et al., "Characterization of a Plasmin–Digest Fragment of Immunoglobulin Gamma that Binds Antigen and Complement", *Boochem. J.*, 145:177–183 (1975).

Prokop, et al., Editors, *Annals of the New York Academy of Sciences*, 646:Table of Contents and Prefaces, Dec. 27, 1991.

Hale, et al., "Remission Induction in Non–Hodgkin Lymphoma with Reshaped Human Monoclonal Antibody Campath–1H", *The Lancet*, 332(8265):1394–1399 (1988).

\* cited by examiner

US 5,876,961 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 11, lines 54-60:

FIGS. [1(a) and 1(b)] *2(a) and 2(b)* and FIGS. [2(a) and 2(b)] *3(a) and 3(b)*. Nucleotide and deduced amino acid sequences of Antibody D heavy chain and light chain respectively. The complete sequence of the pH210H2 insert is shown. The signal peptide and CDR sequences are underlined, and the predicted polyadenylation signal overlined. Amino acids are numbered according to Kabat et al. (1987).

Column 11, line 65 to column 12, line 2:

FIGS. [3(a) and 3(b)] *4(a) and 4(b)*. Nucleotide alignment of cynomologus kappa light chain variable regions with human, rabbit and mouse sequences. CDRs are indicated and dots indicate identity to the human Walker sequence. Codons are numbered according to Kabat et al.

Column 12, lines 6-10:

FIGS. [4(a)] *5A* and [4(b)] *5B*. Amino acid alignment of cynomolgus kappa light chain variable regions with human, rabbit and mouse sequences. CDRs are indicated and dots indicate identity to the human Walker sequence. Amino acid residues are numbered according to Kabat et al.

Column 12, lines 14-19:

FIG. [5] *6*. Nucleotide alignment of cynomolgus kappa light chain constant region with human, rabbit and mouse sequences. Dots indicate identity to the human germline sequence. Codons are numbered according to Kabat et al. One of the ten monkey sequences possessed a G at the nucleotide position underlined.

Column 12, lines 22-27:

FIG. [6] *7*. Amino acid alignment of cynomolgus kappa light chain constant regions with human, rabbit and mouse sequences. Dots indicate identity to the human germline sequence. Amino acid residues are numbered according to Kabat et al.

Column 16, lines 58-59:

The sequence of the variable region is shown in FIGS. [1(a) and 1(b)] *2(a) and 2(b) and FIGS. 3(a) and 3(b)*.

AS A RESULT OF REEXAMINATION, IT HAS BEEN DETERMINED THAT:

Claims 1-14 are cancelled.

\* \* \* \* \*

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GACATTCAGC TGACCCAGTC TCCA 24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GATCAAGCTT CTAACACTCT CCCC 24

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GATCAAGCTT GACATTCAGC TGACCCAGTC TCCA 34

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AACAGCTATG ACCATG 16

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GTTTTCCCAG TCACGAC 17

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GCGTCAGGGT GCTGCTGAGG 20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GGCGGGAAGA TGAAGACAGA                                                      20
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
TTCAGCAGGC ACACAACAGA                                                      20
```

( 2 ) INFORMATION FOR SEQ ID NO:9:

( i ) SEQUENCE CHARACTERISTICS:
        ( A ) LENGTH: 1617 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: sig_peptide
        ( B ) LOCATION: 35..92

( i x ) FEATURE:
        ( A ) NAME/KEY: mat_peptide
        ( B ) LOCATION: 93..1465

( i x ) FEATURE:
        ( A ) NAME/KEY: CDS
        ( B ) LOCATION: 35..1465

( x i ) SEQUENCE DESCRIPTION: SEQ ID NO:9:

```
TCTAAAGAAG CCCCTGGGAG CACAGCTCAT CACC ATG GAC TGG ACC TGG AGG              52
                                     Met Asp Trp Thr Trp Arg
                                     -19              -15

TTC CTC TTT GTG GTG GCA GCA GCT ACA GGT GTC CAG TCC CAG ATG CAG           100
Phe Leu Phe Val Val Ala Ala Ala Thr Gly Val Gln Ser Gln Met Gln
        -10                  -5                       1

GTG GTG CAG TCT GGG GCT GAA GTA AAG AAG CCT GGG TCC TCG GTG ACG           148
Val Val Gln Ser Gly Ala Glu Val Lys Lys Pro Gly Ser Ser Val Thr
         5                  10                  15

GTC TCC TGC AAG GCA TCT GGA GGC ACC TTC AGC AAC TAT GCT ATC AGC           196
Val Ser Cys Lys Ala Ser Gly Gly Thr Phe Ser Asn Tyr Ala Ile Ser
 20                  25                  30                  35

TGG GTG CGA CAG GCC CCT GGA CAA GGG CTT GAG TGG ATG GGA GGG ATC           244
Trp Val Arg Gln Ala Pro Gly Gln Gly Leu Glu Trp Met Gly Gly Ile
             40                  45                  50
```

| | | | | | | | | | | | | | | | | |
|---|---|---|---|---|---|---|---|---|---|---|---|---|---|---|---|---|
| ATC | CCT | CTT | TTT | GGT | ACA | CCA | ACC | TAC | TCA | CAG | AAC | TTC | CAG | GGC | AGA | 292 |
| Ile | Pro | Leu | Phe | Gly | Thr | Pro | Thr | Tyr | Ser | Gln | Asn | Phe | Gln | Gly | Arg | |
| | | | 55 | | | | 60 | | | | | | 65 | | | |
| GTC | ACG | ATT | ACC | GCG | GAC | AAA | TCC | ACC | AGC | ACA | GCC | CAC | ATG | GAG | CTG | 340 |
| Val | Thr | Ile | Thr | Ala | Asp | Lys | Ser | Thr | Ser | Thr | Ala | His | Met | Glu | Leu | |
| | | 70 | | | | 75 | | | | | 80 | | | | | |
| ACT | AGC | CTG | AGA | TCT | GAG | GAC | ACG | GCC | GTG | TAT | TAC | TGT | GCG | ACA | GAT | 388 |
| Thr | Ser | Leu | Arg | Ser | Glu | Asp | Thr | Ala | Val | Tyr | Tyr | Cys | Ala | Thr | Asp | |
| | 85 | | | | 90 | | | | | 95 | | | | | | |
| CGC | TAC | AGG | CAG | GCA | AAT | TTT | GAC | CGG | GCC | CGG | GTT | GGC | TGG | TTC | GAC | 436 |
| Arg | Tyr | Arg | Gln | Ala | Asn | Phe | Asp | Arg | Ala | Arg | Val | Gly | Trp | Phe | Asp | |
| 100 | | | | | 105 | | | | | 110 | | | | | 115 | |
| CCC | TGG | GGC | CAG | GGC | ACC | CTG | GTC | ACC | GTC | TCC | TCA | GCC | TCC | ACC | AAG | 484 |
| Pro | Trp | Gly | Gln | Gly | Thr | Leu | Val | Thr | Val | Ser | Ser | Ala | Ser | Thr | Lys | |
| | | | | 120 | | | | | 125 | | | | | 130 | | |
| GGC | CCA | TCG | GTC | TTC | CCC | CTG | GCA | CCC | TCC | TCC | AAG | AGC | ACC | TCT | GGG | 532 |
| Gly | Pro | Ser | Val | Phe | Pro | Leu | Ala | Pro | Ser | Ser | Lys | Ser | Thr | Ser | Gly | |
| | | | 135 | | | | 140 | | | | | 145 | | | | |
| GGC | ACA | GCG | GCC | CTG | GGC | TGC | CTG | GTC | AAG | GAC | TAC | TTC | CCC | GAA | CCG | 580 |
| Gly | Thr | Ala | Ala | Leu | Gly | Cys | Leu | Val | Lys | Asp | Tyr | Phe | Pro | Glu | Pro | |
| | | 150 | | | | 155 | | | | | 160 | | | | | |
| GTG | ACG | GTG | TCG | TGG | AAC | TCA | GGC | GCC | CTG | ACC | AGC | GGC | GTG | CAC | ACC | 628 |
| Val | Thr | Val | Ser | Trp | Asn | Ser | Gly | Ala | Leu | Thr | Ser | Gly | Val | His | Thr | |
| | 165 | | | | 170 | | | | | 175 | | | | | | |
| TTC | CCG | GCT | GTC | CTA | CAG | TCC | TCA | GGA | CTC | TAC | TCC | CTC | AGC | AGC | GTG | 676 |
| Phe | Pro | Ala | Val | Leu | Gln | Ser | Ser | Gly | Leu | Tyr | Ser | Leu | Ser | Ser | Val | |
| 180 | | | | | 185 | | | | | 190 | | | | | 195 | |
| GTG | ACC | GTG | CCC | TCC | AGC | AGC | TTG | GGC | ACC | CAG | ACC | TAC | ATC | TGC | AAC | 724 |
| Val | Thr | Val | Pro | Ser | Ser | Ser | Leu | Gly | Thr | Gln | Thr | Tyr | Ile | Cys | Asn | |
| | | | | 200 | | | | | 205 | | | | | 210 | | |
| GTG | AAT | CAC | AAG | CCC | AGC | AAC | ACC | AAG | GTG | GAC | AAG | AAA | GTT | GAG | CCC | 772 |
| Val | Asn | His | Lys | Pro | Ser | Asn | Thr | Lys | Val | Asp | Lys | Lys | Val | Glu | Pro | |
| | | | 215 | | | | | 220 | | | | | 225 | | | |
| AAA | TCT | TGT | GAC | AAA | ACT | CAC | ACA | TGC | CCA | CCG | TGC | CCA | GCA | CCT | GAA | 820 |
| Lys | Ser | Cys | Asp | Lys | Thr | His | Thr | Cys | Pro | Pro | Cys | Pro | Ala | Pro | Glu | |
| | | | 230 | | | | 235 | | | | | 240 | | | | |
| CTC | CTG | GGG | GGA | CCG | TCA | GTC | TTC | CTC | TTC | CCC | CCA | AAA | CCC | AAG | GAC | 868 |
| Leu | Leu | Gly | Gly | Pro | Ser | Val | Phe | Leu | Phe | Pro | Pro | Lys | Pro | Lys | Asp | |
| | 245 | | | | | 250 | | | | | 255 | | | | | |
| ACC | CTC | ATG | ATC | TCC | CGG | ACC | CCT | GAG | GTC | ACA | TGC | GTG | GTG | GTG | GAC | 916 |
| Thr | Leu | Met | Ile | Ser | Arg | Thr | Pro | Glu | Val | Thr | Cys | Val | Val | Val | Asp | |
| 260 | | | | | 265 | | | | | 270 | | | | | 275 | |
| GTG | AGC | CAC | GAA | GAC | CCT | GAG | GTC | AAG | TTC | AAC | TGG | TAC | GTG | GAC | GGC | 964 |
| Val | Ser | His | Glu | Asp | Pro | Glu | Val | Lys | Phe | Asn | Trp | Tyr | Val | Asp | Gly | |
| | | | | 280 | | | | | 285 | | | | | 290 | | |
| GTG | GAG | GTG | CAT | AAT | GCC | AAG | ACA | AAG | CCG | CGG | GAG | GAG | CAG | TAC | AAC | 1012 |
| Val | Glu | Val | His | Asn | Ala | Lys | Thr | Lys | Pro | Arg | Glu | Glu | Gln | Tyr | Asn | |
| | | | 295 | | | | | 300 | | | | | 305 | | | |
| AGC | ACG | TAC | CGT | GTG | GTC | AGC | GTC | CTC | ACC | GTC | CTG | CAC | CAG | GAC | TGG | 1060 |
| Ser | Thr | Tyr | Arg | Val | Val | Ser | Val | Leu | Thr | Val | Leu | His | Gln | Asp | Trp | |
| | | 310 | | | | 315 | | | | | 320 | | | | | |
| CTG | AAT | GGC | AAG | GAG | TAC | AAG | TGC | AAG | GTC | TCC | AAC | AAA | GCC | CTC | CCA | 1108 |
| Leu | Asn | Gly | Lys | Glu | Tyr | Lys | Cys | Lys | Val | Ser | Asn | Lys | Ala | Leu | Pro | |
| | 325 | | | | | 330 | | | | | 335 | | | | | |
| GCC | CCC | ATC | GAG | AAA | ACC | ATC | TCC | AAA | GCC | AAA | GGG | CAG | CCC | CGA | GAA | 1156 |
| Ala | Pro | Ile | Glu | Lys | Thr | Ile | Ser | Lys | Ala | Lys | Gly | Gln | Pro | Arg | Glu | |
| 340 | | | | | 345 | | | | | 350 | | | | | 355 | |
| CCA | CAG | GTG | TAC | ACC | CTG | CCC | CCA | TCC | CGG | GAT | GAG | CTG | ACC | AAG | AAC | 1204 |
| Pro | Gln | Val | Tyr | Thr | Leu | Pro | Pro | Ser | Arg | Asp | Glu | Leu | Thr | Lys | Asn | |
| | | | | 360 | | | | | 365 | | | | | 370 | | |

```
CAG GTC AGC CTG ACC TGC CTG GTC AAA GGC TTC TAT CCC AGC GAC ATC         1252
Gln Val Ser Leu Thr Cys Leu Val Lys Gly Phe Tyr Pro Ser Asp Ile
            375                 380                 385

GCC GTG GAG TGG GAG AGC AAT GGG CAG CCG GAG AAC AAC TAC AAG ACC         1300
Ala Val Glu Trp Glu Ser Asn Gly Gln Pro Glu Asn Asn Tyr Lys Thr
            390                 395                 400

ACG CCT CCC GTG CTG GAC TCC GAC GGC TCC TTC TTC CTC TAC AGC AAG         1348
Thr Pro Pro Val Leu Asp Ser Asp Gly Ser Phe Phe Leu Tyr Ser Lys
    405                 410                 415

CTC ACC GTG GAC AAG AGC AGG TGG CAG CAG GGG AAC GTC TTC TCA TGC         1396
Leu Thr Val Asp Lys Ser Arg Trp Gln Gln Gly Asn Val Phe Ser Cys
420                 425                 430                 435

TCC GTG ATG CAT GAG GCT CTG CAC AAC CAC TAC ACG CAG AAG AGC CTC         1444
Ser Val Met His Glu Ala Leu His Asn His Tyr Thr Gln Lys Ser Leu
                440                 445                 450

TCC CTG TCT CCG GGT AAA TGAGTGCGAC GGCCGGCAAG CCCCCGCTCC                1492
Ser Leu Ser Pro Gly Lys
                455

CCGGGCTCTC GCGGTCGCAC GAGGATGCTT GGCACGTACC CCGTGTACAT ACTTCCCGGG       1552

CGCCCAGCAT GGAAATAAAG CACCCAGCGC TGCCCTGGGC CCCTGCGAAA AAAAAAAAAA       1612

AAAAA                                                                   1617
```

( 2 ) INFORMATION FOR SEQ ID NO:10:

( i ) SEQUENCE CHARACTERISTICS:
        ( A ) LENGTH: 476 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Asp Trp Thr Trp Arg Phe Leu Phe Val Val Ala Ala Ala Thr Gly
-19             -15                 -10                 -5

Val Gln Ser Gln Met Gln Val Gln Ser Gly Ala Glu Val Lys Lys
            1               5               10

Pro Gly Ser Ser Val Thr Val Ser Cys Lys Ala Ser Gly Gly Thr Phe
        15              20              25

Ser Asn Tyr Ala Ile Ser Trp Val Arg Gln Ala Pro Gly Gln Gly Leu
30              35              40                          45

Glu Trp Met Gly Gly Ile Ile Pro Leu Phe Gly Thr Pro Thr Tyr Ser
                50              55                      60

Gln Asn Phe Gln Gly Arg Val Thr Ile Thr Ala Asp Lys Ser Thr Ser
            65              70              75

Thr Ala His Met Glu Leu Thr Ser Leu Arg Ser Glu Asp Thr Ala Val
        80              85              90

Tyr Tyr Cys Ala Thr Asp Arg Tyr Arg Gln Ala Asn Phe Asp Arg Ala
    95              100             105

Arg Val Gly Trp Phe Asp Pro Trp Gly Gln Gly Thr Leu Val Thr Val
110             115             120                     125

Ser Ser Ala Ser Thr Lys Gly Pro Ser Val Phe Pro Leu Ala Pro Ser
                130             135                     140

Ser Lys Ser Thr Ser Gly Gly Thr Ala Ala Leu Gly Cys Leu Val Lys
            145             150             155

Asp Tyr Phe Pro Glu Pro Val Thr Val Ser Trp Asn Ser Gly Ala Leu
        160             165             170

Thr Ser Gly Val His Thr Phe Pro Ala Val Leu Gln Ser Ser Gly Leu
    175             180             185
```

Tyr Ser Leu Ser Ser Val Val Thr Val Pro Ser Ser Ser Leu Gly Thr
190                     195                 200                     205

Gln Thr Tyr Ile Cys Asn Val Asn His Lys Pro Ser Asn Thr Lys Val
            210                 215                     220

Asp Lys Lys Val Glu Pro Lys Ser Cys Asp Lys Thr His Thr Cys Pro
            225             230                 235

Pro Cys Pro Ala Pro Glu Leu Leu Gly Gly Pro Ser Val Phe Leu Phe
        240             245                 250

Pro Pro Lys Pro Lys Asp Thr Leu Met Ile Ser Arg Thr Pro Glu Val
    255             260                 265

Thr Cys Val Val Val Asp Val Ser His Glu Asp Pro Glu Val Lys Phe
270             275             280                     285

Asn Trp Tyr Val Asp Gly Val Glu Val His Asn Ala Lys Thr Lys Pro
                290             295                     300

Arg Glu Glu Gln Tyr Asn Ser Thr Tyr Arg Val Val Ser Val Leu Thr
            305                 310                 315

Val Leu His Gln Asp Trp Leu Asn Gly Lys Glu Tyr Lys Cys Lys Val
        320             325                 330

Ser Asn Lys Ala Leu Pro Ala Pro Ile Glu Lys Thr Ile Ser Lys Ala
    335             340                 345

Lys Gly Gln Pro Arg Glu Pro Gln Val Tyr Thr Leu Pro Pro Ser Arg
350                 355                 360                     365

Asp Glu Leu Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
        385             390                 395

Glu Asn Asn Tyr Lys Thr Thr Pro Pro Val Leu Asp Ser Asp Gly Ser
        400             405                 410

Phe Phe Leu Tyr Ser Lys Leu Thr Val Asp Lys Ser Arg Trp Gln Gln
    415             420                 425

Gly Asn Val Phe Ser Cys Ser Val Met His Glu Ala Leu His Asn His
430             435                 440                     445

Tyr Thr Gln Lys Ser Leu Ser Leu Ser Pro Gly Lys
            450                 455

(2) INFORMATION FOR SEQ ID NO:11:

(i) SEQUENCE CHARACTERISTICS:
        (A) LENGTH: 902 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 32..739

(ix) FEATURE:
        (A) NAME/KEY: mat_peptide
        (B) LOCATION: 89..739

(ix) FEATURE:
        (A) NAME/KEY: sig_peptide
        (B) LOCATION: 32..86

(xi) SEQUENCE DESCRIPTION: SEQ ID NO:11:

| | | | | | | | | | | | | | | | | |
|---|---|---|---|---|---|---|---|---|---|---|---|---|---|---|---|---|
| CAAGAGGCAG | CGCTCTCGGG | ACGTCTCCAC | C | ATG | GCC | TGG | GCT | CTG | CTG | CTC | | | | | | 52 |
| | | | | Met | Ala | Trp | Ala | Leu | Leu | Leu | | | | | | |
| | | | | -19 | | | | -15 | | | | | | | | |

| CTC | ACC | CTC | CTC | ACT | CAG | GAC | ACA | GGG | TCC | TGG | GCC | CAG | TCT | GCC | CTG | 100 |
|---|---|---|---|---|---|---|---|---|---|---|---|---|---|---|---|---|
| Leu | Thr | Leu | Leu | Thr | Gln | Asp | Thr | Gly | Ser | Trp | Ala | Gln | Ser | Ala | Leu | |
| | | -10 | | | | -5 | | | | | | 1 | | | | |

| ACT | CAG | CCT | GCC | TCC | GTG | TCT | GGG | TCT | CCT | GGA | CAG | TCG | ATC | ACC | ATC | 148 |
|---|---|---|---|---|---|---|---|---|---|---|---|---|---|---|---|---|
| Thr | Gln | Pro | Ala | Ser | Val | Ser | Gly | Ser | Pro | Gly | Gln | Ser | Ile | Thr | Ile | |
| 5 | | | | | 10 | | | | | 15 | | | | | 20 | |

| TCC | TGC | ACT | GGA | ACC | AAC | AAT | GAT | GTT | GGG | AGT | TAT | AAC | CTT | GTC | TCC | 196 |
|---|---|---|---|---|---|---|---|---|---|---|---|---|---|---|---|---|
| Ser | Cys | Thr | Gly | Thr | Asn | Asn | Asp | Val | Gly | Ser | Tyr | Asn | Leu | Val | Ser | |
| | | | | 25 | | | | | 30 | | | | | 35 | | |

| TGG | TAC | CAG | CAG | CAC | CCA | GGC | AAA | GCC | CCC | AAA | ATC | ATG | ATT | TAT | GAG | 244 |
|---|---|---|---|---|---|---|---|---|---|---|---|---|---|---|---|---|
| Trp | Tyr | Gln | Gln | His | Pro | Gly | Lys | Ala | Pro | Lys | Ile | Met | Ile | Tyr | Glu | |
| | | | 40 | | | | | 45 | | | | | 50 | | | |

| GTC | AGT | AAG | CGG | CCC | TCA | GGG | GTT | TCT | AAT | CGC | TTC | TCT | GGC | TCC | AAG | 292 |
|---|---|---|---|---|---|---|---|---|---|---|---|---|---|---|---|---|
| Val | Ser | Lys | Arg | Pro | Ser | Gly | Val | Ser | Asn | Arg | Phe | Ser | Gly | Ser | Lys | |
| | | 55 | | | | | 60 | | | | | 65 | | | | |

| TCT | GGC | AAC | ACG | GCC | TCC | CTG | ACA | ATC | TCT | GGG | CTC | CAG | GCT | GAG | GAC | 340 |
|---|---|---|---|---|---|---|---|---|---|---|---|---|---|---|---|---|
| Ser | Gly | Asn | Thr | Ala | Ser | Leu | Thr | Ile | Ser | Gly | Leu | Gln | Ala | Glu | Asp | |
| | 70 | | | | | 75 | | | | | 80 | | | | | |

| GAG | GCT | GAT | TAT | TAC | TGC | TGC | TCA | TAT | GCA | GGT | AGT | TAC | ACT | GTG | GTT | 388 |
|---|---|---|---|---|---|---|---|---|---|---|---|---|---|---|---|---|
| Glu | Ala | Asp | Tyr | Tyr | Cys | Cys | Ser | Tyr | Ala | Gly | Ser | Tyr | Thr | Val | Val | |
| 85 | | | | | 90 | | | | | 95 | | | | | 100 | |

| TTC | GGC | GGA | GGG | ACC | AAA | CTG | ACC | GTC | CTA | GGT | CAG | CCC | AAG | GCT | GCC | 436 |
|---|---|---|---|---|---|---|---|---|---|---|---|---|---|---|---|---|
| Phe | Gly | Gly | Gly | Thr | Lys | Leu | Thr | Val | Leu | Gly | Gln | Pro | Lys | Ala | Ala | |
| | | | | 105 | | | | | 110 | | | | | 115 | | |

| CCC | TCG | GTC | ACT | CTG | TTC | CCG | CCC | TCC | TCT | GAG | GAG | CTT | CAA | GCC | AAC | 484 |
|---|---|---|---|---|---|---|---|---|---|---|---|---|---|---|---|---|
| Pro | Ser | Val | Thr | Leu | Phe | Pro | Pro | Ser | Ser | Glu | Glu | Leu | Gln | Ala | Asn | |
| | | | 120 | | | | | 125 | | | | | 130 | | | |

| AAG | GCC | ACA | CTG | GTG | TGT | CTC | ATA | AGT | GAC | TTC | TAC | CCG | GGA | GCC | GTG | 532 |
|---|---|---|---|---|---|---|---|---|---|---|---|---|---|---|---|---|
| Lys | Ala | Thr | Leu | Val | Cys | Leu | Ile | Ser | Asp | Phe | Tyr | Pro | Gly | Ala | Val | |
| | | 135 | | | | | 140 | | | | | 145 | | | | |

| ACA | GTG | GCC | TGG | AAG | GCA | GAT | AGC | AGC | CCC | GTC | AAG | GCG | GGA | GTG | GAG | 580 |
|---|---|---|---|---|---|---|---|---|---|---|---|---|---|---|---|---|
| Thr | Val | Ala | Trp | Lys | Ala | Asp | Ser | Ser | Pro | Val | Lys | Ala | Gly | Val | Glu | |
| | 150 | | | | | 155 | | | | | 160 | | | | | |

| ACC | ACC | ACA | CCC | TCC | AAA | CAA | AGC | AAC | AAC | AAG | TAC | GCG | GCC | AGC | AGC | 628 |
|---|---|---|---|---|---|---|---|---|---|---|---|---|---|---|---|---|
| Thr | Thr | Thr | Pro | Ser | Lys | Gln | Ser | Asn | Asn | Lys | Tyr | Ala | Ala | Ser | Ser | |
| 165 | | | | | 170 | | | | | 175 | | | | | 180 | |

| TAT | CTG | AGC | CTG | ACG | CCT | GAG | CAG | TGG | AAG | TCC | CAC | AGA | AGC | TAC | AGC | 676 |
|---|---|---|---|---|---|---|---|---|---|---|---|---|---|---|---|---|
| Tyr | Leu | Ser | Leu | Thr | Pro | Glu | Gln | Trp | Lys | Ser | His | Arg | Ser | Tyr | Ser | |
| | | | | 185 | | | | | 190 | | | | | 195 | | |

| TGC | CAG | GTC | ACG | CAT | GAA | GGG | AGC | ACC | GTG | GAG | AAG | ACA | GTG | GCC | CCT | 724 |
|---|---|---|---|---|---|---|---|---|---|---|---|---|---|---|---|---|
| Cys | Gln | Val | Thr | His | Glu | Gly | Ser | Thr | Val | Glu | Lys | Thr | Val | Ala | Pro | |
| | | | 200 | | | | | 205 | | | | | 210 | | | |

| ACA | GAA | TGT | TCA | TAGGTTCTAA | ACCCTCACCC | CCCCCACGGG | AGACTAGAGC | | 776 |
|---|---|---|---|---|---|---|---|---|---|
| Thr | Glu | Cys | Ser | | | | | | |
| | | | 215 | | | | | | |

| | | | | |
|---|---|---|---|---|
| TGCAGGATCC | CAGGGGAGGG | GTCTCTCCTC | CCACCCCAAG | GCATCAAGCC | CTTCTCCCTG | 836 |
| CACTCAATAA | ACCCTCAATA | AATATTCTCA | TTGTCAATCA | CAAAAAAAAA | AAAAAAAAA | 896 |
| AAAAAA | | | | | | 902 |

( 2 ) INFORMATION FOR SEQ ID NO:12:

( i ) SEQUENCE CHARACTERISTICS:
        ( A ) LENGTH: 235 amino acids
        ( B ) TYPE: amino acid
        ( D ) TOPOLOGY: linear ( i i ) MOLECULE TYPE: protein (xi) SEQUENCE DESCRIPTION: SEQ ID NO:12:

| Met | Ala | Trp | Ala | Leu | Leu | Leu | Leu | Thr | Leu | Leu | Thr | Gln | Asp | Thr | Gly |
|---|---|---|---|---|---|---|---|---|---|---|---|---|---|---|---|
| -19 | | | | -15 | | | | | -10 | | | | | -5 | |

| Ser | Trp | Ala | Gln | Ser | Ala | Leu | Thr | Gln | Pro | Ala | Ser | Val | Ser | Gly | Ser |
|---|---|---|---|---|---|---|---|---|---|---|---|---|---|---|---|
| | | | 1 | | | | 5 | | | | | 10 | | | |

| Pro | Gly | Gln | Ser | Ile | Thr | Ile | Ser | Cys | Thr | Gly | Thr | Asn | Asn | Asp | Val |
|---|---|---|---|---|---|---|---|---|---|---|---|---|---|---|---|
| | 15 | | | | 20 | | | | | 25 | | | | | |

| Gly | Ser | Tyr | Asn | Leu | Val | Ser | Trp | Tyr | Gln | Gln | His | Pro | Gly | Lys | Ala |
|---|---|---|---|---|---|---|---|---|---|---|---|---|---|---|---|
| 30 | | | | | 35 | | | | | 40 | | | | | 45 |

| Pro | Lys | Ile | Met | Ile | Tyr | Glu | Val | Ser | Lys | Arg | Pro | Ser | Gly | Val | Ser |
|---|---|---|---|---|---|---|---|---|---|---|---|---|---|---|---|
| | | | | 50 | | | | | 55 | | | | | 60 | |

| Asn | Arg | Phe | Ser | Gly | Ser | Lys | Ser | Gly | Asn | Thr | Ala | Ser | Leu | Thr | Ile |
|---|---|---|---|---|---|---|---|---|---|---|---|---|---|---|---|
| | | | 65 | | | | | 70 | | | | | 75 | | |

| Ser | Gly | Leu | Gln | Ala | Glu | Asp | Glu | Ala | Asp | Tyr | Tyr | Cys | Cys | Ser | Tyr |
|---|---|---|---|---|---|---|---|---|---|---|---|---|---|---|---|
| | | 80 | | | | | 85 | | | | | 90 | | | |

| Ala | Gly | Ser | Tyr | Thr | Val | Val | Phe | Gly | Gly | Gly | Thr | Lys | Leu | Thr | Val |
|---|---|---|---|---|---|---|---|---|---|---|---|---|---|---|---|
| | 95 | | | | | 100 | | | | | 105 | | | | |

| Leu | Gly | Gln | Pro | Lys | Ala | Ala | Pro | Ser | Val | Thr | Leu | Phe | Pro | Pro | Ser |
|---|---|---|---|---|---|---|---|---|---|---|---|---|---|---|---|
| 110 | | | | | 115 | | | | | 120 | | | | | 125 |

| Ser | Glu | Glu | Leu | Gln | Ala | Asn | Lys | Ala | Thr | Leu | Val | Cys | Leu | Ile | Ser |
|---|---|---|---|---|---|---|---|---|---|---|---|---|---|---|---|
| | | | | 130 | | | | | 135 | | | | | 140 | |

| Asp | Phe | Tyr | Pro | Gly | Ala | Val | Thr | Val | Ala | Trp | Lys | Ala | Asp | Ser | Ser |
|---|---|---|---|---|---|---|---|---|---|---|---|---|---|---|---|
| | | | 145 | | | | | 150 | | | | | 155 | | |

| Pro | Val | Lys | Ala | Gly | Val | Glu | Thr | Thr | Thr | Pro | Ser | Lys | Gln | Ser | Asn |
|---|---|---|---|---|---|---|---|---|---|---|---|---|---|---|---|
| | | 160 | | | | | 165 | | | | | 170 | | | |

| Asn | Lys | Tyr | Ala | Ala | Ser | Ser | Tyr | Leu | Ser | Leu | Thr | Pro | Glu | Gln | Trp |
|---|---|---|---|---|---|---|---|---|---|---|---|---|---|---|---|
| | 175 | | | | | 180 | | | | | 185 | | | | |

| Lys | Ser | His | Arg | Ser | Tyr | Ser | Cys | Gln | Val | Thr | His | Glu | Gly | Ser | Thr |
|---|---|---|---|---|---|---|---|---|---|---|---|---|---|---|---|
| 190 | | | | | 195 | | | | | 200 | | | | | 205 |

| Val | Glu | Lys | Thr | Val | Ala | Pro | Thr | Glu | Cys | Ser |
|---|---|---|---|---|---|---|---|---|---|---|
| | | | | 210 | | | | | 215 | |

(2) INFORMATION FOR SEQ ID NO:13:

(i) SEQUENCE CHARACTERISTICS:
        (A) LENGTH: 321 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..321

(xi) SEQUENCE DESCRIPTION: SEQ ID NO:13:

| GAC | ATC | CAG | ATG | ACC | CAG | TCT | CCA | TCC | TCC | CTG | TCT | GCA | TCT | GTA | GGA | 48 |
|---|---|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly | |
| 1 | | | | 5 | | | | | 10 | | | | | 15 | | |

| GAC | AGA | GTC | ACC | ATC | ACT | TGC | CGG | GCA | AGT | CAG | AGC | ATT | AGC | AAT | TAT | 96 |
|---|---|---|---|---|---|---|---|---|---|---|---|---|---|---|---|---|
| Asp | Arg | Val | Thr | Ile | Thr | Cys | Arg | Ala | Ser | Gln | Ser | Ile | Ser | Asn | Tyr | |
| | | | 20 | | | | | 25 | | | | | 30 | | | |

| TTA | AAT | TGG | TAT | CAA | CAG | AAA | CCA | GGG | AAA | GCC | CCT | AAG | CTC | CTG | ATC | 144 |
|---|---|---|---|---|---|---|---|---|---|---|---|---|---|---|---|---|
| Leu | Asn | Trp | Tyr | Gln | Gln | Lys | Pro | Gly | Lys | Ala | Pro | Lys | Leu | Leu | Ile | |
| | | 35 | | | | | 40 | | | | | 45 | | | | |

```
TAT  GCT  GCA  TCC  AGT  TTG  CAA  AGT  GGG  GTC  ACA  TCA  AGG  TTC  AGT  GGC     192
Tyr  Ala  Ala  Ser  Ser  Leu  Gln  Ser  Gly  Val  Thr  Ser  Arg  Phe  Ser  Gly
     50                       55                       60

AGT  GGA  TCT  GGG  ACA  GAC  TTC  ACT  CTC  ACC  ATC  AGC  AGT  CTG  CAA  CCT     240
Ser  Gly  Ser  Gly  Thr  Asp  Phe  Thr  Leu  Thr  Ile  Ser  Ser  Leu  Gln  Pro
65                            70                       75                       80

GAA  GAT  TCT  GCA  ACT  TAC  TAC  TGT  CAA  CAG  AGT  TAC  AGT  ACC  CTG  ATC     288
Glu  Asp  Ser  Ala  Thr  Tyr  Tyr  Cys  Gln  Gln  Ser  Tyr  Ser  Thr  Leu  Ile
                    85                       90                       95

ACC  TTC  GGC  CAA  GGG  ACA  CGA  CTG  GAG  ATT  AAA                              321
Thr  Phe  Gly  Gln  Gly  Thr  Arg  Leu  Glu  Ile  Lys
               100                      105
```

(2) INFORMATION FOR SEQ ID NO:14:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:14:

```
Asp  Ile  Gln  Met  Thr  Gln  Ser  Pro  Ser  Ser  Leu  Ser  Ala  Ser  Val  Gly
1                  5                      10                      15

Asp  Arg  Val  Thr  Ile  Thr  Cys  Arg  Ala  Ser  Gln  Ser  Ile  Ser  Asn  Tyr
               20                       25                      30

Leu  Asn  Trp  Tyr  Gln  Gln  Lys  Pro  Gly  Lys  Ala  Pro  Lys  Leu  Leu  Ile
               35                       40                      45

Tyr  Ala  Ala  Ser  Ser  Leu  Gln  Ser  Gly  Val  Thr  Ser  Arg  Phe  Ser  Gly
     50                       55                       60

Ser  Gly  Ser  Gly  Thr  Asp  Phe  Thr  Leu  Thr  Ile  Ser  Ser  Leu  Gln  Pro
65                            70                       75                       80

Glu  Asp  Ser  Ala  Thr  Tyr  Tyr  Cys  Gln  Gln  Ser  Tyr  Ser  Thr  Leu  Ile
                    85                       90                       95

Thr  Phe  Gly  Gln  Gly  Thr  Arg  Leu  Glu  Ile  Lys
               100                      105
```

(2) INFORMATION FOR SEQ ID NO:15:

(i) SEQUENCE CHARACTERISTICS:
        (A) LENGTH: 324 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..324

(xi) SEQUENCE DESCRIPTION: SEQ ID NO:15:

```
GAC  ATT  CAG  CTG  ACC  CAG  TCT  CCA  TCT  TCC  CTG  TCT  GCA  TCG  GTA  GGA     48
Asp  Ile  Gln  Leu  Thr  Gln  Ser  Pro  Ser  Ser  Leu  Ser  Ala  Ser  Val  Gly
1                  5                       10                      15

GAC  AGA  GTC  ACC  ATC  ACC  TGC  AGG  GCA  AGT  CAG  GGC  ATT  AGC  GAT  TAT     96
Asp  Arg  Val  Thr  Ile  Thr  Cys  Arg  Ala  Ser  Gln  Gly  Ile  Ser  Asp  Tyr
               20                       25                      30

TTA  AGT  TGG  TAT  CAG  CAG  AAA  CCA  GGG  AAA  GCC  CCT  GAG  CTC  CTG  ATC     144
```

| Leu | Ser | Trp | Tyr | Gln | Gln | Lys | Pro | Gly | Lys | Ala | Pro | Glu | Leu | Leu | Ile | |
|-----|-----|-----|-----|-----|-----|-----|-----|-----|-----|-----|-----|-----|-----|-----|-----|--|
|     |     | 35  |     |     |     |     | 40  |     |     |     |     | 45  |     |     |     |  |

| TAT | GCT | GCT | TCC | AGT | TTG | CAA | AGT | GGG | ATT | CCC | TCT | CGG | TTC | AGC | GGC | 192 |
|-----|-----|-----|-----|-----|-----|-----|-----|-----|-----|-----|-----|-----|-----|-----|-----|-----|
| Tyr | Ala | Ala | Ser | Ser | Leu | Gln | Ser | Gly | Ile | Pro | Ser | Arg | Phe | Ser | Gly |     |
|     | 50  |     |     |     | 55  |     |     |     |     | 60  |     |     |     |     |     |     |

| AGT | GGA | TCT | GGG | ACA | GAT | TTC | ACT | CTC | ACC | ATC | AGC | AGC | CTG | CAG | CCT | 240 |
|-----|-----|-----|-----|-----|-----|-----|-----|-----|-----|-----|-----|-----|-----|-----|-----|-----|
| Ser | Gly | Ser | Gly | Thr | Asp | Phe | Thr | Leu | Thr | Ile | Ser | Ser | Leu | Gln | Pro |     |
| 65  |     |     |     |     | 70  |     |     |     |     | 75  |     |     |     |     | 80  |     |

| GAA | GAT | TCT | GCA | GTT | TAT | TAC | TGT | CAA | CAC | ACT | TAT | AGT | GAC | CCG | TAC | 288 |
|-----|-----|-----|-----|-----|-----|-----|-----|-----|-----|-----|-----|-----|-----|-----|-----|-----|
| Glu | Asp | Ser | Ala | Val | Tyr | Tyr | Cys | Gln | His | Thr | Tyr | Ser | Asp | Pro | Tyr |     |
|     |     |     |     | 85  |     |     |     |     | 90  |     |     |     |     | 95  |     |     |

| AGT | TTT | GGC | CAG | GGG | ACC | AAA | GTG | GAC | ATC | AAA | CGA | 324 |
|-----|-----|-----|-----|-----|-----|-----|-----|-----|-----|-----|-----|-----|
| Ser | Phe | Gly | Gln | Gly | Thr | Lys | Val | Asp | Ile | Lys | Arg |     |
|     |     |     | 100 |     |     |     |     | 105 |     |     |     |     |

(2) INFORMATION FOR SEQ ID NO:16:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:16:

| Asp | Ile | Gln | Leu | Thr | Gln | Ser | Pro | Ser | Ser | Leu | Ser | Ala | Ser | Val | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Arg | Val | Thr | Ile | Thr | Cys | Arg | Ala | Ser | Gln | Gly | Ile | Ser | Asp | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Ser | Trp | Tyr | Gln | Gln | Lys | Pro | Gly | Lys | Ala | Pro | Glu | Leu | Leu | Ile |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Tyr | Ala | Ala | Ser | Ser | Leu | Gln | Ser | Gly | Ile | Pro | Ser | Arg | Phe | Ser | Gly |
|-----|-----|-----|-----|-----|-----|-----|-----|-----|-----|-----|-----|-----|-----|-----|-----|
|     | 50  |     |     |     | 55  |     |     |     |     | 60  |     |     |     |     |     |

| Ser | Gly | Ser | Gly | Thr | Asp | Phe | Thr | Leu | Thr | Ile | Ser | Ser | Leu | Gln | Pro |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Glu | Asp | Ser | Ala | Val | Tyr | Tyr | Cys | Gln | His | Thr | Tyr | Ser | Asp | Pro | Tyr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ser | Phe | Gly | Gln | Gly | Thr | Lys | Val | Asp | Ile | Lys | Arg |
|-----|-----|-----|-----|-----|-----|-----|-----|-----|-----|-----|-----|
|     |     |     | 100 |     |     |     |     | 105 |     |     |     |

(2) INFORMATION FOR SEQ ID NO:17:

(i) SEQUENCE CHARACTERISTICS:
        (A) LENGTH: 324 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..324

(xi) SEQUENCE DESCRIPTION: SEQ ID NO:17:

| GAC | ATT | CAG | CTG | ACC | CAG | TCT | CCA | TCC | TCC | CTG | TCT | GCT | TCT | GTA | GGA | 48 |
|-----|-----|-----|-----|-----|-----|-----|-----|-----|-----|-----|-----|-----|-----|-----|-----|----|
| Asp | Ile | Gln | Leu | Thr | Gln | Ser | Pro | Ser | Ser | Leu | Ser | Ala | Ser | Val | Gly |    |
| 1   |     |     |     | 5   |     |     |     |     | 10  |     |     |     |     | 15  |     |    |

| GAC | AGA | GTC | ACC | ATC | ACT | TGC | CGG | GCA | AGT | CAG | GGC | ATT | AGC | ACT | TAT | 96 |
|-----|-----|-----|-----|-----|-----|-----|-----|-----|-----|-----|-----|-----|-----|-----|-----|----|
| Asp | Arg | Val | Thr | Ile | Thr | Cys | Arg | Ala | Ser | Gln | Gly | Ile | Ser | Thr | Tyr |    |
|     |     |     | 20  |     |     |     |     | 25  |     |     |     |     | 30  |     |     |    |

| | | | | | | | | | | | | | | | | |
|---|---|---|---|---|---|---|---|---|---|---|---|---|---|---|---|---|
| TTA | AGT | TGG | TAT | CAG | CAG | AAA | CCA | GGG | AAA | GCC | CCT | AAG | CTC | CTG | ATC | 144 |
| Leu | Ser | Trp | Tyr | Gln | Gln | Lys | Pro | Gly | Lys | Ala | Pro | Lys | Leu | Leu | Ile | |
| | | 35 | | | | 40 | | | | | 45 | | | | | |
| TAT | TAT | GCA | AAC | AGT | TTG | GCA | AGT | GGG | GTC | CCA | TCA | AGG | TTC | AGC | GGC | 192 |
| Tyr | Tyr | Ala | Asn | Ser | Leu | Ala | Ser | Gly | Val | Pro | Ser | Arg | Phe | Ser | Gly | |
| | 50 | | | | | 55 | | | | | 60 | | | | | |
| AGT | GGA | TCT | GGG | ACA | GAA | TTC | ACT | CTC | ACC | ATC | AGC | AGC | CTG | CAG | CCT | 240 |
| Ser | Gly | Ser | Gly | Thr | Glu | Phe | Thr | Leu | Thr | Ile | Ser | Ser | Leu | Gln | Pro | |
| 65 | | | | | 70 | | | | | 75 | | | | | 80 | |
| GAA | GAT | TCT | GCA | ACT | TAT | TAC | TGT | GGA | CAG | GGT | AAT | AGT | TAC | CCT | CTC | 288 |
| Glu | Asp | Ser | Ala | Thr | Tyr | Tyr | Cys | Gly | Gln | Gly | Asn | Ser | Tyr | Pro | Leu | |
| | | | | 85 | | | | | 90 | | | | | 95 | | |
| ACT | TTC | GGC | GGA | GGG | ACC | AAG | GTG | GAG | ATC | AAA | CGA | | | | | 324 |
| Thr | Phe | Gly | Gly | Gly | Thr | Lys | Val | Glu | Ile | Lys | Arg | | | | | |
| | | | 100 | | | | | 105 | | | | | | | | |

( 2 ) INFORMATION FOR SEQ ID NO:18:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| | | | | | | | | | | | | | | |
|---|---|---|---|---|---|---|---|---|---|---|---|---|---|---|
| Asp | Ile | Gln | Leu | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Gly | Ile | Ser | Thr | Tyr |
| | | | 20 | | | | | 25 | | | | | 30 | | |
| Leu | Ser | Trp | Tyr | Gln | Gln | Lys | Pro | Gly | Lys | Ala | Pro | Lys | Leu | Leu | Ile |
| | | | 35 | | | | 40 | | | | | 45 | | | |
| Tyr | Tyr | Ala | Asn | Ser | Leu | Ala | Ser | Gly | Val | Pro | Ser | Arg | Phe | Ser | Gly |
| | 50 | | | | | 55 | | | | | 60 | | | | |
| Ser | Gly | Ser | Gly | Thr | Glu | Phe | Thr | Leu | Thr | Ile | Ser | Ser | Leu | Gln | Pro |
| 65 | | | | | 70 | | | | | 75 | | | | | 80 |
| Glu | Asp | Ser | Ala | Thr | Tyr | Tyr | Cys | Gly | Gln | Gly | Asn | Ser | Tyr | Pro | Leu |
| | | | | 85 | | | | | 90 | | | | | 95 | |
| Thr | Phe | Gly | Gly | Gly | Thr | Lys | Val | Glu | Ile | Lys | Arg | | | | |
| | | | 100 | | | | | 105 | | | | | | | |

( 2 ) INFORMATION FOR SEQ ID NO:19:

( i ) SEQUENCE CHARACTERISTICS:
        ( A ) LENGTH: 324 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..324

( x i ) SEQUENCE DESCRIPTION: SEQ ID NO:19:

| | | | | | | | | | | | | | | | | |
|---|---|---|---|---|---|---|---|---|---|---|---|---|---|---|---|---|
| GAC | ATT | CAG | CTG | ACC | CAG | TCT | CCA | TCC | TCT | CAG | TCT | GCA | TCT | GTA | GGA | 48 |
| Asp | Ile | Gln | Leu | Thr | Gln | Ser | Pro | Ser | Ser | Gln | Ser | Ala | Ser | Val | Gly | |
| 1 | | | | 5 | | | | | 10 | | | | | 15 | | |
| GAC | AGA | GTG | ACC | ATT | ACT | TGC | CAG | GCG | AGT | CAA | AGC | CTT | AGC | AAT | TAT | 96 |

```
Asp Arg Val Thr  Ile Thr Cys Gln  Ala Ser Gln Ser  Leu Ser Asn Tyr
         20                 25                 30

TTA AAT TGG TAT  CAG CAG AAA CCA  GGG AAA ATT CCT  AAG CTC CTG ATC    144
Leu Asn Trp Tyr  Gln Gln Lys Pro  Gly Lys Ile Pro  Lys Leu Leu Ile
         35                 40                 45

TAT AGG GCA TCC  AGT TTG CAA AGT  GGG ATT CCC TCT  CGG TTC AGC GGC    192
Tyr Arg Ala Ser  Ser Leu Gln Ser  Gly Ile Pro Ser  Arg Phe Ser Gly
         50                 55                 60

AGT GGA TCT GGG  ACG GAT TTC ACT  CTC ACC ATC AGC  AGC CTG CAG CCT    240
Ser Gly Ser Gly  Thr Asp Phe Thr  Leu Thr Ile Ser  Ser Leu Gln Pro
 65                      70                 75                 80

GAA GAT TTT GCC  ACT TAT TAC TGT  CAG CAT AAT TAT  GGT ACC CCT CTC    288
Glu Asp Phe Ala  Thr Tyr Tyr Cys  Gln His Asn Tyr  Gly Thr Pro Leu
                      85                 90                 95

ACT TTC GGC GGA  GGG ACC AAG GTG  GAG ATC AAA CGA                     324
Thr Phe Gly Gly  Gly Thr Lys Val  Glu Ile Lys Arg
             100                 105
```

(2) INFORMATION FOR SEQ ID NO:20:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:20:

```
Asp Ile Gln Leu  Thr Gln Ser Pro  Ser Ser Gln Ser  Ala Ser Val Gly
 1                5                 10                 15

Asp Arg Val Thr  Ile Thr Cys Gln  Ala Ser Gln Ser  Leu Ser Asn Tyr
         20                 25                 30

Leu Asn Trp Tyr  Gln Gln Lys Pro  Gly Lys Ile Pro  Lys Leu Leu Ile
         35                 40                 45

Tyr Arg Ala Ser  Ser Leu Gln Ser  Gly Ile Pro Ser  Arg Phe Ser Gly
         50                 55                 60

Ser Gly Ser Gly  Thr Asp Phe Thr  Leu Thr Ile Ser  Ser Leu Gln Pro
 65                      70                 75                 80

Glu Asp Phe Ala  Thr Tyr Tyr Cys  Gln His Asn Tyr  Gly Thr Pro Leu
                      85                 90                 95

Thr Phe Gly Gly  Gly Thr Lys Val  Glu Ile Lys Arg
             100                 105
```

(2) INFORMATION FOR SEQ ID NO:21:

(i) SEQUENCE CHARACTERISTICS:
        (A) LENGTH: 324 base pairs
        (B) TYPE: nucleic acid
        (C) STRANDEDNESS: both
        (D) TOPOLOGY: linear (ii) MOLECULE TYPE: DNA (genomic)

(ix) FEATURE:
        (A) NAME/KEY: CDS
        (B) LOCATION: 1..324

(xi) SEQUENCE DESCRIPTION: SEQ ID NO:21:

```
GACATTCAGC  TGACCCAGTC  TCCACTCTCC  CTGCCCGTCA  GTCTTGGAGA  GTCGGCCTCC     60

ATCTCCTNNN  NNNNNNNNN   NNNNNNNNNN  NNNNNNNNNN  NNNNNNNNNN  NNNNNNNNNN    120

NNNNNNNNNN  NNNNNNNNNN  NNNNNNNNNN  NNNNNNNNNN  NNNNNNNNNN  NNTCCAGAC     180

AGGTTCACTG  GCAGTGGGTC  AGGCACTGAT  TTCACACTGA  AAATCAGCAG  AGTGGAGGCT    240
```

```
GAGGATGTTG  GGGTTTATTA  CTGCATGCAA  GCTCTTCGGT  CTCCTTGGAC  GTTCGGCCAA      300

GGGACCAAGG  TGGAAATCAG  ACGA                                                324
```

( 2 ) INFORMATION FOR SEQ ID NO:22:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Asp Ile Gln Leu Thr Gln Ser Pro Leu Ser Leu Pro Val Ser Leu Gly
 1               5                  10                  15

Glu Ser Ala Ser Ile Thr Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Pro Asp Arg Phe Thr Gly
            50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Met Gln Ala Leu Arg Ser Pro Trp
                85                  90                  95

Thr Phe Gly Gln Gly Thr Lys Val Glu Ile Arg Arg
                100                 105
```

( 2 ) INFORMATION FOR SEQ ID NO:23:

( i ) SEQUENCE CHARACTERISTICS:
        ( A ) LENGTH: 324 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..324

( x i ) SEQUENCE DESCRIPTION: SEQ ID NO:23:

```
GAC ATT CAG CTG ACC CAG TCT CCA TCT TCC CTG TCT GCA TCG GTA GGA    48
Asp Ile Gln Leu Thr Gln Ser Pro Ser Ser Leu Ser Ala Ser Val Gly
 1               5                  10                  15

GAC AGA GTC ACC ATC ACC TGC AGG GCA AGT CAG GGC ATT AGC GAT TAT    96
Asp Arg Val Thr Ile Thr Cys Arg Ala Ser Gln Gly Ile Ser Asp Tyr
            20                  25                  30

TTA AGT TGG TAT CAG CAG AAA CCA GGA AAA GCT CCT AAG CTC CTG ATC   144
Leu Ser Trp Tyr Gln Gln Lys Pro Gly Lys Ala Pro Lys Leu Leu Ile
            35                  40                  45

TAT GCT GCA TCC AGT TTG CAA AGT GGG GTC CCA TCA AGG TTC AGC GGC   192
Tyr Ala Ala Ser Ser Leu Gln Ser Gly Val Pro Ser Arg Phe Ser Gly
        50                  55                  60

AGT GGA TCT GGG ACA GAA TTC ACT CTC ACC ATC AGC AGC CTG CAA CCT   240
Ser Gly Ser Gly Thr Glu Phe Thr Leu Thr Ile Ser Ser Leu Gln Pro
65                  70                  75                  80

GAA GAT TTT GCA ACT TAT TAC TGT CTA CAG GGT TAT GGT ACC CCG TAC   288
```

```
Glu  Asp  Phe  Ala  Thr  Tyr  Tyr  Cys  Leu  Gln  Gly  Tyr  Gly  Thr  Pro  Tyr
               85                       90                            95

AGT  TTT  GGC  CAG  GGG  ACC  AAA  GTG  GAG  ATC  AAA  CGA                      324
Ser  Phe  Gly  Gln  Gly  Thr  Lys  Val  Glu  Ile  Lys  Arg
               100                      105
```

( 2 ) INFORMATION FOR SEQ ID NO:24:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Asp  Ile  Gln  Leu  Thr  Gln  Ser  Pro  Ser  Ser  Leu  Ser  Ala  Ser  Val  Gly
 1                   5                        10                       15

Asp  Arg  Val  Thr  Ile  Thr  Cys  Arg  Ala  Ser  Gln  Gly  Ile  Ser  Asp  Tyr
               20                       25                       30

Leu  Ser  Trp  Tyr  Gln  Gln  Lys  Pro  Gly  Lys  Ala  Pro  Lys  Leu  Leu  Ile
               35                       40                       45

Tyr  Ala  Ala  Ser  Ser  Leu  Gln  Ser  Gly  Val  Pro  Ser  Arg  Phe  Ser  Gly
      50                        55                       60

Ser  Gly  Ser  Gly  Thr  Glu  Phe  Thr  Leu  Thr  Ile  Ser  Ser  Leu  Gln  Pro
 65                       70                       75                        80

Glu  Asp  Phe  Ala  Thr  Tyr  Tyr  Cys  Leu  Gln  Gly  Tyr  Gly  Thr  Pro  Tyr
               85                       90                            95

Ser  Phe  Gly  Gln  Gly  Thr  Lys  Val  Glu  Ile  Lys  Arg
               100                      105
```

( 2 ) INFORMATION FOR SEQ ID NO:25:

( i ) SEQUENCE CHARACTERISTICS:
        ( A ) LENGTH: 324 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..324

( x i ) SEQUENCE DESCRIPTION: SEQ ID NO:25:

```
GAC  ATT  CAG  CTG  ACC  CAG  TCT  CCA  TCC  TCC  CTG  TCT  GCA  TCT  GTG  GGA    48
Asp  Ile  Gln  Leu  Thr  Gln  Ser  Pro  Ser  Ser  Leu  Ser  Ala  Ser  Val  Gly
 1                   5                        10                       15

GAC  ACA  GTC  ACC  ATC  ACT  TGT  CGG  GCA  AGT  CAG  GAC  ATT  AGC  AAT  AAT    96
Asp  Thr  Val  Thr  Ile  Thr  Cys  Arg  Ala  Ser  Gln  Asp  Ile  Ser  Asn  Asn
               20                       25                       30

TTA  GTC  TGG  TAT  CAG  CAG  AAA  CCA  GGG  AAA  GCC  CCT  AAG  CTC  CTG  ATC   144
Leu  Val  Trp  Tyr  Gln  Gln  Lys  Pro  Gly  Lys  Ala  Pro  Lys  Leu  Leu  Ile
               35                       40                       45

TAT  GCT  GCA  TCC  AGA  TTG  CAA  GAT  GGG  GTC  CCA  TCA  AGG  TTC  AGC  GGC   192
Tyr  Ala  Ala  Ser  Arg  Leu  Gln  Asp  Gly  Val  Pro  Ser  Arg  Phe  Ser  Gly
      50                        55                       60

AGT  GGG  TCT  GGG  ACC  GAT  TTC  ACC  CTC  ACA  ATT  AAT  CCT  GTG  GAA  GCT   240
Ser  Gly  Ser  Gly  Thr  Asp  Phe  Thr  Leu  Thr  Ile  Asn  Pro  Val  Glu  Ala
 65                       70                       75                        80
```

```
GAC  GAT  GCT  GCG  GAT  TAC  TAC  TGT  CTA  CAG  ACT  AAG  AGT  TCT  CCT  CGG      288
Asp  Asp  Ala  Ala  Asp  Tyr  Tyr  Cys  Leu  Gln  Thr  Lys  Ser  Ser  Pro  Arg
                    85                      90                      95

ACG  TTC  GGC  CAA  GGG  ACC  AAG  GTG  GAA  ATC  AAA  CGA                          324
Thr  Phe  Gly  Gln  Gly  Thr  Lys  Val  Glu  Ile  Lys  Arg
               100                      105
```

( 2 ) INFORMATION FOR SEQ ID NO:26:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Asp  Ile  Gln  Leu  Thr  Gln  Ser  Pro  Ser  Ser  Leu  Ser  Ala  Ser  Val  Gly
 1                    5                      10                      15

Asp  Thr  Val  Thr  Ile  Thr  Cys  Arg  Ala  Ser  Gln  Asp  Ile  Ser  Asn  Asn
                    20                      25                      30

Leu  Val  Trp  Tyr  Gln  Gln  Lys  Pro  Gly  Lys  Ala  Pro  Lys  Leu  Leu  Ile
                35                      40                      45

Tyr  Ala  Ala  Ser  Arg  Leu  Gln  Asp  Gly  Val  Pro  Ser  Arg  Phe  Ser  Gly
     50                      55                      60

Ser  Gly  Ser  Gly  Thr  Asp  Phe  Thr  Leu  Thr  Ile  Asn  Pro  Val  Glu  Ala
 65                      70                      75                      80

Asp  Asp  Ala  Ala  Asp  Tyr  Tyr  Cys  Leu  Gln  Thr  Lys  Ser  Ser  Pro  Arg
                    85                      90                      95

Thr  Phe  Gly  Gln  Gly  Thr  Lys  Val  Glu  Ile  Lys  Arg
               100                      105
```

( 2 ) INFORMATION FOR SEQ ID NO:27:

( i ) SEQUENCE CHARACTERISTICS:
        ( A ) LENGTH: 324 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: CDS
        ( B ) LOCATION: 1..324

( i x ) FEATURE:
        ( A ) NAME/KEY: mat_peptide
        ( B ) LOCATION: 31..324

( x i ) SEQUENCE DESCRIPTION: SEQ ID NO:27:

```
GACATTCAGC  TGACCCAGTC  TCCANNNNNN  NNNNNNNNNN  NNNNNNNNNN  NNNNNNNNNN       60

NNNNNNNNNN  NNNNNNNNNN  NNNNNNNNNN  NNNNNNNNNN  NNNNNNNNNN  NNNNNNNNNN      120

NNNNNNNNNN  NNCAGCCCTT  GATTTATGAG  GTTTCCAACC  GGGCCTCTGG  AGTCCAGAC       180

AGGTTCAGTG  GCAGTGGGTC  GGACACTGAT  TTCACACTCA  AAATCAGCAG  AGTGGAGGCT      240

GAGGATGTTG  GGGTTTATTA  CTGCATGCAA  TATACACACA  TTCCATTCAC  TTTCGGCCCC      300

GGGACCAAAC  TGGATATCAA  ACGA                                               324
```

( 2 ) INFORMATION FOR SEQ ID NO:28:

( i ) SEQUENCE CHARACTERISTICS:
        ( A ) LENGTH: 108 amino acids (B) TYPE: amino acid
(D) TOPOLOGY: linear (i i) MOLECULE TYPE: protein (x i) SEQUENCE DESCRIPTION: SEQ ID NO:28:

| Asp | Ile | Gln | Leu | Thr | Gln | Ser | Pro | Xaa | Xaa | Xaa | Xaa | Xaa | Xaa | Xaa | Xaa |
|---|---|---|---|---|---|---|---|---|---|---|---|---|---|---|---|
| 1 | | | | 5 | | | | | 10 | | | | | 15 | |
| Xaa | Xaa | Xaa | Xaa | Xaa | Xaa | Xaa | Xaa | Xaa | Xaa | Xaa | Xaa | Xaa | Xaa | Xaa | Xaa |
| | | | 20 | | | | | 25 | | | | | 30 | | |
| Xaa | Xaa | Xaa | Xaa | Xaa | Xaa | Xaa | Xaa | Xaa | Xaa | Xaa | Xaa | Gln | Pro | Leu | Ile |
| | | | 35 | | | | | 40 | | | | | 45 | | |
| Tyr | Glu | Val | Ser | Asn | Arg | Ala | Ser | Gly | Val | Pro | Asp | Arg | Phe | Ser | Gly |
| | | 50 | | | | | 55 | | | | | 60 | | | |
| Ser | Gly | Ser | Asp | Thr | Asp | Phe | Thr | Leu | Lys | Ile | Ser | Arg | Val | Glu | Ala |
| 65 | | | | | 70 | | | | | 75 | | | | | 80 |
| Glu | Asp | Val | Gly | Val | Tyr | Tyr | Cys | Met | Gln | Tyr | Thr | His | Ile | Pro | Phe |
| | | | | 85 | | | | | 90 | | | | | 95 | |
| Thr | Phe | Gly | Pro | Gly | Thr | Lys | Leu | Asp | Ile | Lys | Arg | | | | |
| | | | 100 | | | | | 105 | | | | | | | |

(2) INFORMATION FOR SEQ ID NO:29:

(i) SEQUENCE CHARACTERISTICS:
(A) LENGTH: 324 base pairs
(B) TYPE: nucleic acid
(C) STRANDEDNESS: both
(D) TOPOLOGY: linear (i i) MOLECULE TYPE: cDNA (i i i) HYPOTHETICAL: NO (i v) ANTI-SENSE: NO (i x) FEATURE:
(A) NAME/KEY: CDS
(B) LOCATION: 1..324

(x i) SEQUENCE DESCRIPTION: SEQ ID NO:29:

| GAC | ATT | CAG | CTG | ACC | CAG | TCT | CCA | TCC | TCC | CTG | TCT | GCA | TCT | GTA | GGA | | 48 |
|---|---|---|---|---|---|---|---|---|---|---|---|---|---|---|---|---|---|
| Asp | Ile | Gln | Leu | Thr | Gln | Ser | Pro | Ser | Ser | Leu | Ser | Ala | Ser | Val | Gly | | |
| 1 | | | | 5 | | | | | 10 | | | | | 15 | | | |
| GAC | AGA | GTC | ACC | ATC | ACT | TGC | CGG | GCA | AGT | CAG | AGC | ATT | AGC | AAT | TAT | | 96 |
| Asp | Arg | Val | Thr | Ile | Thr | Cys | Arg | Ala | Ser | Gln | Ser | Ile | Ser | Asn | Tyr | | |
| | | | 20 | | | | | 25 | | | | | 30 | | | | |
| TTA | AAT | TGG | TAT | CAA | CAG | AAA | CCA | GGG | AAA | GCC | CCT | CAG | CCC | TTG | ATT | | 144 |
| Leu | Asn | Trp | Tyr | Gln | Gln | Lys | Pro | Gly | Lys | Ala | Pro | Gln | Pro | Leu | Ile | | |
| | | | 35 | | | | | 40 | | | | | 45 | | | | |
| TAT | GAG | GTT | TCC | AAC | CGG | GCC | TCT | GGA | GTC | CCA | GAC | AGG | TTC | AGT | GGC | | 192 |
| Tyr | Glu | Val | Ser | Asn | Arg | Ala | Ser | Gly | Val | Pro | Asp | Arg | Phe | Ser | Gly | | |
| | | 50 | | | | | 55 | | | | | 60 | | | | | |
| AGT | GGG | TCG | GAC | ACT | GAT | TTC | ACA | CTC | AAA | ATC | AGC | AGA | GTG | GAG | GCT | | 240 |
| Ser | Gly | Ser | Asp | Thr | Asp | Phe | Thr | Leu | Lys | Ile | Ser | Arg | Val | Glu | Ala | | |
| 65 | | | | | 70 | | | | | 75 | | | | | 80 | | |
| GAG | GAT | GTT | GGG | GTT | TAT | TAC | TGC | ATG | CAA | TAT | ACA | CAC | ATT | CCA | TTC | | 288 |
| Glu | Asp | Val | Gly | Val | Tyr | Tyr | Cys | Met | Gln | Tyr | Thr | His | Ile | Pro | Phe | | |
| | | | | 85 | | | | | 90 | | | | | 95 | | | |
| ACT | TTC | GGC | CCC | GGG | ACC | AAA | CTG | GAT | ATC | AAA | CGA | | | | | | 324 |
| Thr | Phe | Gly | Pro | Gly | Thr | Lys | Leu | Asp | Ile | Lys | Arg | | | | | | |
| | | | 100 | | | | | 105 | | | | | | | | | |

(2) INFORMATION FOR SEQ ID NO:30:

( i ) SEQUENCE CHARACTERISTICS:
  ( A ) LENGTH: 108 amino acids
  ( B ) TYPE: amino acid
  ( D ) TOPOLOGY: linear ( i i ) MOLECULE TYPE: protein ( x i ) SEQUENCE DESCRIPTION: SEQ ID NO:30:

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Gln Pro Leu Ile
            35                  40                  45

Tyr Glu Val Ser Asn Arg Ala Ser Gly Val Pro Asp Arg Phe Ser Gly
        50                  55                  60

Ser Gly Ser Asp Thr Asp Phe Thr Leu Lys Ile Ser Arg Val Glu Ala
65                  70                  75                  80

Glu Asp Val Gly Val Tyr Tyr Cys Met Gln Tyr Thr His Ile Pro Phe
                85                  90                  95

Thr Phe Gly Pro Gly Thr Lys Leu Asp Ile Lys Arg
                100                 105
```

( 2 ) INFORMATION FOR SEQ ID NO:31:

( i ) SEQUENCE CHARACTERISTICS:
    ( A ) LENGTH: 324 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 1..324

( x i ) SEQUENCE DESCRIPTION: SEQ ID NO:31:

```
GAC ATT CAG CTG ACC CAG TCT CCA TCC TCC CTG TCT GCA TCT GTG GGA     48
Asp Ile Gln Leu Thr Gln Ser Pro Ser Ser Leu Ser Ala Ser Val Gly
 1               5                  10                  15

GAC ACA GTC ACC ATC ACT TGT CGG GCA AGT CAG GGC ATT AGC AAT AAT     96
Asp Thr Val Thr Ile Thr Cys Arg Ala Ser Gln Gly Ile Ser Asn Asn
                20                  25                  30

TTA GCC TGG TAT CAG CAG AAA CCA GGA AAA GCT CCT AAG CGC CTG ATC    144
Leu Ala Trp Tyr Gln Gln Lys Pro Gly Lys Ala Pro Lys Arg Leu Ile
            35                  40                  45

TAT GCT GCA TCC AGT TTG GAA AGT GGG GTC CCA TCA AGG TTC AGT GGC    192
Tyr Ala Ala Ser Ser Leu Glu Ser Gly Val Pro Ser Arg Phe Ser Gly
        50                  55                  60

AGT GGA TCT GGG ACA GAA TTC ACT CTC ACC ATC AGC AGC CTG CAG CCT    240
Ser Gly Ser Gly Thr Glu Phe Thr Leu Thr Ile Ser Ser Leu Gln Pro
65                  70                  75                  80

GAA GAT TTT GCA ACT TAT TAC TGT CAA CAG GAT AAC AGT TAT CCT TTC    288
Glu Asp Phe Ala Thr Tyr Tyr Cys Gln Gln Asp Asn Ser Tyr Pro Phe
                85                  90                  95

ACT TTC GGC GGA GGG ACC AAG GTG GAG ATC AAA CGA                    324
Thr Phe Gly Gly Gly Thr Lys Val Glu Ile Lys Arg
                100                 105
```

( 2 ) INFORMATION FOR SEQ ID NO:32:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Asp Ile Gln Leu Thr Gln Ser Pro Ser Ser Leu Ser Ala Ser Val Gly
 1               5                  10                  15
Asp Thr Val Thr Ile Thr Cys Arg Ala Ser Gln Gly Ile Ser Asn Asn
             20                  25                  30
Leu Ala Trp Tyr Gln Gln Lys Pro Gly Lys Ala Pro Lys Arg Leu Ile
             35                  40                  45
Tyr Ala Ala Ser Ser Leu Glu Ser Gly Val Pro Ser Arg Phe Ser Gly
         50                  55                  60
Ser Gly Ser Gly Thr Glu Phe Thr Leu Thr Ile Ser Ser Leu Gln Pro
65                   70                  75                  80
Glu Asp Phe Ala Thr Tyr Tyr Cys Gln Gln Asp Asn Ser Tyr Pro Phe
                     85                  90                  95
Thr Phe Gly Gly Gly Thr Lys Val Glu Ile Lys Arg
                 100                 105
```

( 2 ) INFORMATION FOR SEQ ID NO:33:

( i ) SEQUENCE CHARACTERISTICS:
        ( A ) LENGTH: 324 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..324

( x i ) SEQUENCE DESCRIPTION: SEQ ID NO:33:

```
GAC ATT CAG CTG ACC CAG TCT CCA TCC TCC CTG TCT GCA TCT GTG GGA      48
Asp Ile Gln Leu Thr Gln Ser Pro Ser Ser Leu Ser Ala Ser Val Gly
 1               5                  10                  15
GAC ACA GTC ACC ATC ACT TGT CGG GCA AGT CAG GGC ATT AGC AAT AAT      96
Asp Thr Val Thr Ile Thr Cys Arg Ala Ser Gln Gly Ile Ser Asn Asn
             20                  25                  30
TTA GCC TGG TAT CAG CAG AAA CCA GGA AAA GCT CCT AAG CGC CTG ATC     144
Leu Ala Trp Tyr Gln Gln Lys Pro Gly Lys Ala Pro Lys Arg Leu Ile
             35                  40                  45
TAT GCT GCA TCC AGT TTG GAA AGT GGG GTC CCA TCA AGG TTC AGT GGC     192
Tyr Ala Ala Ser Ser Leu Glu Ser Gly Val Pro Ser Arg Phe Ser Gly
         50                  55                  60
AGT GGA TCT GGG ACA GAA TTC ACT CTC ACC ATC AGC AGC CTG CAG CCT     240
Ser Gly Ser Gly Thr Glu Phe Thr Leu Thr Ile Ser Ser Leu Gln Pro
65                   70                  75                  80
GAA GAT TTT GCA ACT TAT TAC TGT CAA CAG GAT AAC AGT TAT CCT TTC     288
Glu Asp Phe Ala Thr Tyr Tyr Cys Gln Gln Asp Asn Ser Tyr Pro Phe
                     85                  90                  95
ACT TTC GGC GGA GGG ACC AAG GTG GAG ATC AAA CGA                     324
Thr Phe Gly Gly Gly Thr Lys Val Glu Ile Lys Arg
                 100                 105
```

( 2 ) INFORMATION FOR SEQ ID NO:34:

( i ) SEQUENCE CHARACTERISTICS:
  ( A ) LENGTH: 108 amino acids
  ( B ) TYPE: amino acid
  ( D ) TOPOLOGY: linear ( i i ) MOLECULE TYPE: protein ( x i ) SEQUENCE DESCRIPTION: SEQ ID NO:34:

```
Asp  Ile  Gln  Leu  Thr  Gln  Ser  Pro  Ser  Ser  Leu  Ser  Ala  Ser  Val  Gly
 1                   5                        10                       15

Asp  Thr  Val  Thr  Ile  Thr  Cys  Arg  Ala  Ser  Gln  Gly  Ile  Ser  Asn  Asn
                20                       25                  30

Leu  Ala  Trp  Tyr  Gln  Gln  Lys  Pro  Gly  Lys  Ala  Pro  Lys  Arg  Leu  Ile
           35                       40                       45

Tyr  Ala  Ala  Ser  Ser  Leu  Glu  Ser  Gly  Val  Pro  Ser  Arg  Phe  Ser  Gly
      50                       55                       60

Ser  Gly  Ser  Gly  Thr  Glu  Phe  Thr  Leu  Thr  Ile  Ser  Ser  Leu  Gln  Pro
 65                       70                       75                       80

Glu  Asp  Phe  Ala  Thr  Tyr  Tyr  Cys  Gln  Gln  Asp  Asn  Ser  Tyr  Pro  Phe
                85                       90                       95

Thr  Phe  Gly  Gly  Gly  Thr  Lys  Val  Glu  Ile  Lys  Arg
               100                      105
```

( 2 ) INFORMATION FOR SEQ ID NO:35:

( i ) SEQUENCE CHARACTERISTICS:
  ( A ) LENGTH: 342 base pairs
  ( B ) TYPE: nucleic acid
  ( C ) STRANDEDNESS: both
  ( D ) TOPOLOGY: linear ( i i ) MOLECULE TYPE: cDNA ( i x ) FEATURE:
  ( A ) NAME/KEY: CDS
  ( B ) LOCATION: 1..342

( x i ) SEQUENCE DESCRIPTION: SEQ ID NO:35:

```
GAC  ATT  GTG  ATG  ACT  CAG  TCT  CCA  ACT  TTC  CTT  GCT  GTG  ACA  GCA  AGT    48
Asp  Ile  Val  Met  Thr  Gln  Ser  Pro  Thr  Phe  Leu  Ala  Val  Thr  Ala  Ser
 1                   5                        10                       15

AAG  AAG  GTC  ACC  ATT  AGT  TGC  ACT  GCC  TCT  GAG  AGC  CTT  TAT  TCA  AGC    96
Lys  Lys  Val  Thr  Ile  Ser  Cys  Thr  Ala  Ser  Glu  Ser  Leu  Tyr  Ser  Ser
                20                       25                       30

AAA  CAC  AAG  GTG  CAC  TAC  TTG  GCT  TGG  TAC  CAG  AAG  AAA  CCA  GAG  CAA   144
Lys  His  Lys  Val  His  Tyr  Leu  Ala  Trp  Tyr  Gln  Lys  Lys  Pro  Glu  Gln
           35                       40                       45

TCT  CCT  AAA  CTG  CTG  ATA  TAC  GGG  GCA  TCC  AAC  CGA  TAC  ATT  GGG  GTC   192
Ser  Pro  Lys  Leu  Leu  Ile  Tyr  Gly  Ala  Ser  Asn  Arg  Tyr  Ile  Gly  Val
      50                       55                       60

CCT  GAT  CGC  TTC  ACA  GGC  AGT  GGA  TCT  GGG  ACA  GAT  TTC  ACT  CTG  ACC   240
Pro  Asp  Arg  Phe  Thr  Gly  Ser  Gly  Ser  Gly  Thr  Asp  Phe  Thr  Leu  Thr
 65                       70                       75                       80

ATC  AGC  AGT  GTA  CAG  GTT  GAA  GAC  CTC  ACA  CAT  TAT  TAC  TGT  GCA  CAG   288
Ile  Ser  Ser  Val  Gln  Val  Glu  Asp  Leu  Thr  His  Tyr  Tyr  Cys  Ala  Gln
                85                       90                       95

TTT  TAC  AGC  TAT  CCT  CTC  ACG  TTC  GGT  GCT  GGG  ACC  AAG  CTG  GAG  CTG   336
Phe  Tyr  Ser  Tyr  Pro  Leu  Thr  Phe  Gly  Ala  Gly  Thr  Lys  Leu  Glu  Leu
               100                      105                      110

AAA  CGG                                                                          342
```

Lys Arg (2) INFORMATION FOR SEQ ID NO:36:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:36:

```
Asp Ile Val Met Thr Gln Ser Pro Thr Phe Leu Ala Val Thr Ala Ser
 1               5                  10                  15
Lys Lys Val Thr Ile Ser Cys Thr Ala Ser Glu Ser Leu Tyr Ser Ser
                20                  25                  30
Lys His Lys Val His Tyr Leu Ala Trp Tyr Gln Lys Lys Pro Glu Gln
            35                  40                  45
Ser Pro Lys Leu Leu Ile Tyr Gly Ala Ser Asn Arg Tyr Ile Gly Val
        50                  55                  60
Pro Asp Arg Phe Thr Gly Ser Gly Ser Gly Thr Asp Phe Thr Leu Thr
65                  70                  75                  80
Ile Ser Ser Val Gln Val Glu Asp Leu Thr His Tyr Tyr Cys Ala Gln
                85                  90                  95
Phe Tyr Ser Tyr Pro Leu Thr Phe Gly Ala Gly Thr Lys Leu Glu Leu
                100                 105                 110
Lys Arg
```

(2) INFORMATION FOR SEQ ID NO:37:

(i) SEQUENCE CHARACTERISTICS:
        (A) LENGTH: 327 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..327

(xi) SEQUENCE DESCRIPTION: SEQ ID NO:37:

```
GCC CTC GTG ATG ACC CAG ACT CCA GCC TCC GTG TCT GCA GCT GTG GGA    48
Ala Leu Val Met Thr Gln Thr Pro Ala Ser Val Ser Ala Ala Val Gly
 1               5                  10                  15

GGC ACA GTC ACC ATC AAG TGC CAG GCC AGT GAG AAC ATT TAC AGC TCT    96
Gly Thr Val Thr Ile Lys Cys Gln Ala Ser Glu Asn Ile Tyr Ser Ser
                20                  25                  30

TTA GCC TGG TAT CAG CAG AAA CCA GGG CAG CCT CCC AAG CTC CTG ATC   144
Leu Ala Trp Tyr Gln Gln Lys Pro Gly Gln Pro Pro Lys Leu Leu Ile
            35                  40                  45

TAT GGT GCA TCC ACT CTG GCA TCT GGG GTC CCA TCG CGG TTC AAA GGC   192
Tyr Gly Ala Ser Thr Leu Ala Ser Gly Val Pro Ser Arg Phe Lys Gly
        50                  55                  60

AGT AGA TCT GGG ACA GAG TAC ACT CTC ACC ATC AGC GGC GTG CAG CGT   240
Ser Arg Ser Gly Thr Glu Tyr Thr Leu Thr Ile Ser Gly Val Gln Arg
65                  70                  75                  80

GAG GAT GCT GCC ACC TAC TAC TGT CTA GGC AGT GAT AGT AGT AGC GAT   288
Glu Asp Ala Ala Thr Tyr Tyr Cys Leu Gly Ser Asp Ser Ser Ser Asp
```

|     |     |     |     |     | 85  |     |     |     | 90  |     |     |     | 95  |     |     |
| --- | --- | --- | --- | --- | --- | --- | --- | --- | --- | --- | --- | --- | --- | --- | --- |
| ACT | GCT | TTC | GGC | GGA | GGG | ACC | GAG | CTG | GAG | ATC | CTA | TGT |     |     | 327 |
| Thr | Ala | Phe | Gly | Gly | Gly | Thr | Glu | Leu | Glu | Ile | Leu | Cys |     |     |     |
|     |     |     | 100 |     |     |     |     | 105 |     |     |     |     |     |     |     |

( 2 ) INFORMATION FOR SEQ ID NO:38:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

| Ala | Leu | Val | Met | Thr | Gln | Thr | Pro | Ala | Ser | Val | Ser | Ala | Ala | Val | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gly | Thr | Val | Thr | Ile | Lys | Cys | Gln | Ala | Ser | Glu | Asn | Ile | Tyr | Ser | Ser |
|     |     |     | 20  |     |     |     |     | 25  |     |     |     |     | 30  |     |     |
| Leu | Ala | Trp | Tyr | Gln | Gln | Lys | Pro | Gly | Gln | Pro | Pro | Lys | Leu | Leu | Ile |
|     |     |     | 35  |     |     |     |     | 40  |     |     |     |     | 45  |     |     |
| Tyr | Gly | Ala | Ser | Thr | Leu | Ala | Ser | Gly | Val | Pro | Ser | Arg | Phe | Lys | Gly |
|     | 50  |     |     |     |     | 55  |     |     |     |     | 60  |     |     |     |     |
| Ser | Arg | Ser | Gly | Thr | Glu | Tyr | Thr | Leu | Thr | Ile | Ser | Gly | Val | Gln | Arg |
| 65  |     |     |     |     | 70  |     |     |     |     | 75  |     |     |     |     | 80  |
| Glu | Asp | Ala | Ala | Thr | Tyr | Tyr | Cys | Leu | Gly | Ser | Asp | Ser | Ser | Ser | Asp |
|     |     |     |     | 85  |     |     |     |     | 90  |     |     |     |     | 95  |     |
| Thr | Ala | Phe | Gly | Gly | Gly | Thr | Glu | Leu | Glu | Ile | Leu | Cys |     |     |     |
|     |     |     | 100 |     |     |     |     | 105 |     |     |     |     |     |     |     |

( 2 ) INFORMATION FOR SEQ ID NO:39:

( i ) SEQUENCE CHARACTERISTICS:
        ( A ) LENGTH: 321 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..321

( x i ) SEQUENCE DESCRIPTION: SEQ ID NO:39:

| ACT | GTG | GCT | GCA | CCA | TCT | GTC | TTC | ATC | TTC | CCG | CCA | TCT | GAT | GAG | CAG | 48  |
| --- | --- | --- | --- | --- | --- | --- | --- | --- | --- | --- | --- | --- | --- | --- | --- | --- |
| Thr | Val | Ala | Ala | Pro | Ser | Val | Phe | Ile | Phe | Pro | Pro | Ser | Asp | Glu | Gln |     |
| 1   |     |     |     | 5   |     |     |     |     | 10  |     |     |     |     | 15  |     |     |
| TTG | AAA | TCT | GGA | ACT | GCC | TCT | GTT | GTG | TGC | CTG | CTG | AAT | AAC | TTC | TAT | 96  |
| Leu | Lys | Ser | Gly | Thr | Ala | Ser | Val | Val | Cys | Leu | Leu | Asn | Asn | Phe | Tyr |     |
|     |     |     | 20  |     |     |     |     | 25  |     |     |     |     | 30  |     |     |     |
| CCC | AGA | GAG | GCC | AAA | GTA | CAG | TGG | AAG | GTG | GAT | AAC | GCC | CTC | CAA | TCG | 144 |
| Pro | Arg | Glu | Ala | Lys | Val | Gln | Trp | Lys | Val | Asp | Asn | Ala | Leu | Gln | Ser |     |
|     |     |     | 35  |     |     |     |     | 40  |     |     |     |     | 45  |     |     |     |
| GGT | AAC | TCC | CAG | GAG | AGT | GTC | ACA | GAG | CAG | GAC | AGC | AAG | GAC | AGC | ACC | 192 |
| Gly | Asn | Ser | Gln | Glu | Ser | Val | Thr | Glu | Gln | Asp | Ser | Lys | Asp | Ser | Thr |     |
|     |     |     | 50  |     |     |     |     | 55  |     |     |     |     | 60  |     |     |     |
| TAC | AGC | CTC | AGC | AGC | ACC | CTG | ACG | CTG | AGC | AAA | GCA | GAC | TAC | GAG | AAA | 240 |
| Tyr | Ser | Leu | Ser | Ser | Thr | Leu | Thr | Leu | Ser | Lys | Ala | Asp | Tyr | Glu | Lys |     |
| 65  |     |     |     |     | 70  |     |     |     |     | 75  |     |     |     |     | 80  |     |

| | | | | | | | | | | | | | | | | |
|---|---|---|---|---|---|---|---|---|---|---|---|---|---|---|---|---|
| CAC | AAA | GTC | TAC | GCC | TGC | GAA | GTC | ACC | CAT | CAG | GGC | CTG | AGC | TCG | CCC | 288 |
| His | Lys | Val | Tyr | Ala | Cys | Glu | Val | Thr | His | Gln | Gly | Leu | Ser | Ser | Pro | |
| | | | | 85 | | | | 90 | | | | | | 95 | | |
| GTC | ACA | AAG | AGC | TTC | AAC | AGG | GGA | GAG | TGT | TAG | | | | | | 321 |
| Val | Thr | Lys | Ser | Phe | Asn | Arg | Gly | Glu | Cys | | | | | | | |
| | | | 100 | | | | | 105 | | | | | | | | |

( 2 ) INFORMATION FOR SEQ ID NO:40:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

| | | | | | | | | | | | | | | |
|---|---|---|---|---|---|---|---|---|---|---|---|---|---|---|
| Thr | Val | Ala | Ala | Pro | Ser | Val | Phe | Ile | Phe | Pro | Pro | Ser | Asp | Glu | Gln |
| 1 | | | | 5 | | | | | 10 | | | | | 15 |
| Leu | Lys | Ser | Gly | Thr | Ala | Ser | Val | Val | Cys | Leu | Leu | Asn | Asn | Phe | Tyr |
| | | | 20 | | | | | 25 | | | | | 30 | |
| Pro | Arg | Glu | Ala | Lys | Val | Gln | Trp | Lys | Val | Asp | Asn | Ala | Leu | Gln | Ser |
| | | 35 | | | | | 40 | | | | | 45 | | |
| Gly | Asn | Ser | Gln | Glu | Ser | Val | Thr | Glu | Gln | Asp | Ser | Lys | Asp | Ser | Thr |
| | 50 | | | | | 55 | | | | | 60 | | | |
| Tyr | Ser | Leu | Ser | Ser | Thr | Leu | Thr | Leu | Ser | Lys | Ala | Asp | Tyr | Glu | Lys |
| 65 | | | | | 70 | | | | 75 | | | | | 80 |
| His | Lys | Val | Tyr | Ala | Cys | Glu | Val | Thr | His | Gln | Gly | Leu | Ser | Ser | Pro |
| | | | | 85 | | | | 90 | | | | | | 95 |
| Val | Thr | Lys | Ser | Phe | Asn | Arg | Gly | Glu | Cys | | | | | | |
| | | | 100 | | | | | 105 | | | | | | |

( 2 ) INFORMATION FOR SEQ ID NO:41:

( i ) SEQUENCE CHARACTERISTICS:
        ( A ) LENGTH: 321 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: YES ( i v ) ANTI-SENSE: NO ( i x ) FEATURE:
        ( A ) NAME/KEY: CDS
        ( B ) LOCATION: 1..321

( x i ) SEQUENCE DESCRIPTION: SEQ ID NO:41:

| | | | | | | | | | | | | | | | | |
|---|---|---|---|---|---|---|---|---|---|---|---|---|---|---|---|---|
| GCT | GTG | GCT | GCA | CCA | TCT | GTC | TTC | ATC | TTC | CCG | CCA | TCT | GAG | GAT | CAG | 48 |
| Ala | Val | Ala | Ala | Pro | Ser | Val | Phe | Ile | Phe | Pro | Pro | Ser | Glu | Asp | Gln | |
| 1 | | | | 5 | | | | | 10 | | | | | 15 | | |
| GTG | AAA | TCT | GGA | ACT | GTC | TCT | GTT | GTG | TGC | CTG | CTG | AAT | AAC | TTC | TAT | 96 |
| Val | Lys | Ser | Gly | Thr | Val | Ser | Val | Val | Cys | Leu | Leu | Asn | Asn | Phe | Tyr | |
| | | | 20 | | | | | 25 | | | | | 30 | | | |
| CCC | AGA | GAG | GCC | AGC | GTA | AAG | TGG | AAG | GTG | GAT | GGT | GCC | CTC | AAA | ACG | 144 |
| Pro | Arg | Glu | Ala | Ser | Val | Lys | Trp | Lys | Val | Asp | Gly | Ala | Leu | Lys | Thr | |
| | | | 35 | | | | | 40 | | | | | 45 | | | |
| GAT | AAC | TCC | CAG | GAG | AGT | GTC | ACA | GAG | CAG | GAC | AGC | AAG | GAC | AAC | ACC | 192 |
| Asp | Asn | Ser | Gln | Glu | Ser | Val | Thr | Glu | Gln | Asp | Ser | Lys | Asp | Asn | Thr | |
| | | | 50 | | | | | 55 | | | | | 60 | | | |
| TAC | AGC | CTG | AGC | AGC | ACC | CTG | ACG | CTG | AGC | AGC | ACA | GAC | TAC | CAG | AGT | 240 |
| Tyr | Ser | Leu | Ser | Ser | Thr | Leu | Thr | Leu | Ser | Ser | Thr | Asp | Tyr | Gln | Ser | |

| | | | | | | | | | 65 | | | | | 70 | | | | | 75 | | | | | 80 | | |
|---|---|---|---|---|---|---|---|---|---|---|---|---|---|---|---|---|---|---|---|---|---|---|---|---|---|---|

```
CAC  AAT  GTC  TAT  GCC  TGC  GAA  GTC  ACC  CAT  CAG  GGC  CTG  AGC  TCG  CCC         288
His  Asn  Val  Tyr  Ala  Cys  Glu  Val  Thr  His  Gln  Gly  Leu  Ser  Ser  Pro
                         85                      90                      95

GTC  ACC  AAG  AGC  TTC  AAC  AGG  GGA  GAG  TGT  TAG                                  321
Val  Thr  Lys  Ser  Phe  Asn  Arg  Gly  Glu  Cys
               100                 105
```

( 2 ) INFORMATION FOR SEQ ID NO:42:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

```
Ala  Val  Ala  Ala  Pro  Ser  Val  Phe  Ile  Phe  Pro  Pro  Ser  Glu  Asp  Gln
 1                   5                    10                       15

Val  Lys  Ser  Gly  Thr  Val  Ser  Val  Cys  Leu  Leu  Asn  Asn  Phe  Tyr
               20                   25                        30

Pro  Arg  Glu  Ala  Ser  Val  Lys  Trp  Lys  Val  Asp  Gly  Ala  Leu  Lys  Thr
               35                   40                        45

Asp  Asn  Ser  Gln  Glu  Ser  Val  Thr  Glu  Gln  Asp  Ser  Lys  Asp  Asn  Thr
      50                        55                        60

Tyr  Ser  Leu  Ser  Ser  Thr  Leu  Thr  Leu  Ser  Ser  Thr  Asp  Tyr  Gln  Ser
 65                       70                        75                   80

His  Asn  Val  Tyr  Ala  Cys  Glu  Val  Thr  His  Gln  Gly  Leu  Ser  Ser  Pro
                         85                      90                      95

Val  Thr  Lys  Ser  Phe  Asn  Arg  Gly  Glu  Cys
               100                 105
```

( 2 ) INFORMATION FOR SEQ ID NO:43:

( i ) SEQUENCE CHARACTERISTICS:
        ( A ) LENGTH: 321 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..321

( x i ) SEQUENCE DESCRIPTION: SEQ ID NO:43:

```
GAT  CCA  ATT  GCG  CCT  ACT  GTC  CTC  CTC  TTC  CCA  CCA  TCT  GCT  GAT  CAG         48
Asp  Pro  Ile  Ala  Pro  Thr  Val  Leu  Leu  Phe  Pro  Pro  Ser  Ala  Asp  Gln
 1                   5                    10                       15

CTG  ACA  ACT  GAA  ACA  GTC  ACC  ATC  GTG  TGC  GTG  GCA  AAT  AAA  TTC  CGT         96
Leu  Thr  Thr  Glu  Thr  Val  Thr  Ile  Val  Cys  Val  Ala  Asn  Lys  Phe  Arg
                    20                   25                        30

CCC  AAT  GAC  ATC  ACC  GTC  ACC  TGG  AAG  GTG  GAT  GAC  GAA  ATC  CAA  CAG        144
Pro  Asn  Asp  Ile  Thr  Val  Thr  Trp  Lys  Val  Asp  Asp  Glu  Ile  Gln  Gln
               35                   40                        45

AGC  GGC  TTC  GAG  AAC  AGT  ACA  ACA  CCG  CAG  AGC  CCC  GAG  GAC  TGT  ACC        192
Ser  Gly  Phe  Glu  Asn  Ser  Thr  Thr  Pro  Gln  Ser  Pro  Glu  Asp  Cys  Thr
      50                        55                        60
```

| | | | | | | | | | | | | | | | | |
|---|---|---|---|---|---|---|---|---|---|---|---|---|---|---|---|---|
| TAC | AAC | CTC | AGC | AGC | ACT | CTG | TCA | CTG | ACC | AAA | GCA | CAG | TAC | AAC | AGC | 240 |
| Tyr | Asn | Leu | Ser | Ser | Thr | Leu | Ser | Leu | Thr | Lys | Ala | Gln | Tyr | Asn | Ser | |
| 65 | | | | | 70 | | | | 75 | | | | | | 80 | |
| CAC | AGC | GTG | TAC | ACC | TGC | GAG | GTG | GTC | CAT | CAC | AAC | TCG | GGC | TCA | GCG | 288 |
| His | Ser | Val | Tyr | Thr | Cys | Glu | Val | Val | His | His | Asn | Ser | Gly | Ser | Ala | |
| | | | | 85 | | | | | 90 | | | | | 95 | | |
| ATC | GTC | CAG | AGC | TTC | AAT | AGG | GGT | GAC | TGT | TAG | | | | | | 321 |
| Ile | Val | Gln | Ser | Phe | Asn | Arg | Gly | Asp | Cys | | | | | | | |
| | | | 100 | | | | | 105 | | | | | | | | |

( 2 ) INFORMATION FOR SEQ ID NO:44:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

| | | | | | | | | | | | | | | |
|---|---|---|---|---|---|---|---|---|---|---|---|---|---|---|
| Asp | Pro | Ile | Ala | Pro | Thr | Val | Leu | Leu | Phe | Pro | Pro | Ser | Ala | Asp | Gln |
| 1 | | | | 5 | | | | | 10 | | | | | 15 |
| Leu | Thr | Thr | Glu | Thr | Val | Thr | Ile | Val | Cys | Val | Ala | Asn | Lys | Phe | Arg |
| | | | 20 | | | | | 25 | | | | | 30 | |
| Pro | Asn | Asp | Ile | Thr | Val | Thr | Trp | Lys | Val | Asp | Asp | Glu | Ile | Gln | Gln |
| | | | 35 | | | | | 40 | | | | | 45 | |
| Ser | Gly | Phe | Glu | Asn | Ser | Thr | Thr | Pro | Gln | Ser | Pro | Glu | Asp | Cys | Thr |
| | | | 50 | | | | | 55 | | | | | 60 | |
| Tyr | Asn | Leu | Ser | Ser | Thr | Leu | Ser | Leu | Thr | Lys | Ala | Gln | Tyr | Asn | Ser |
| 65 | | | | | 70 | | | | 75 | | | | | | 80 |
| His | Ser | Val | Tyr | Thr | Cys | Glu | Val | Val | His | His | Asn | Ser | Gly | Ser | Ala |
| | | | | 85 | | | | | 90 | | | | | 95 | |
| Ile | Val | Gln | Ser | Phe | Asn | Arg | Gly | Asp | Cys | | | | | | |
| | | | 100 | | | | | 105 | | | | | | | |

( 2 ) INFORMATION FOR SEQ ID NO:45:

( i ) SEQUENCE CHARACTERISTICS:
        ( A ) LENGTH: 321 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..321

( x i ) SEQUENCE DESCRIPTION: SEQ ID NO:45:

| | | | | | | | | | | | | | | | | |
|---|---|---|---|---|---|---|---|---|---|---|---|---|---|---|---|---|
| GCT | GAT | GCT | GCA | CCA | ACT | GTA | TCC | ATC | TTC | CCA | CCA | TCC | AGT | GAG | CAG | 48 |
| Ala | Asp | Ala | Ala | Pro | Thr | Val | Ser | Ile | Phe | Pro | Pro | Ser | Ser | Glu | Gln | |
| 1 | | | | 5 | | | | | 10 | | | | | 15 | | |
| TTA | ACA | TCT | GGA | GGT | GCC | TCA | GTC | GTG | TGC | TTC | TTG | AAC | AAC | TTC | TAC | 96 |
| Leu | Thr | Ser | Gly | Gly | Ala | Ser | Val | Val | Cys | Phe | Leu | Asn | Asn | Phe | Tyr | |
| | | | 20 | | | | | 25 | | | | | 30 | | | |
| CCC | AAA | GAC | ATC | AAT | GTC | AAG | TGG | AAG | ATT | GAT | GGC | AGT | GAA | CGA | CAA | 144 |
| Pro | Lys | Asp | Ile | Asn | Val | Lys | Trp | Lys | Ile | Asp | Gly | Ser | Glu | Arg | Gln | |
| | | | 35 | | | | | 40 | | | | | 45 | | | |
| AAT | GGC | GTC | CTG | AAC | AGT | TGG | ACT | GAT | CAG | GAC | AGC | AAA | GAC | AGC | ACC | 192 |
| Asn | Gly | Val | Leu | Asn | Ser | Trp | Thr | Asp | Gln | Asp | Ser | Lys | Asp | Ser | Thr | |

-continued

```
                        50                              55                                  60
TAC  AGC  ATG  AGC  AGC  ACC  CTC  ACG  TTG  ACC  AAG  GAC  GAG  TAT  GAA  CGA              240
Tyr  Ser  Met  Ser  Ser  Thr  Leu  Thr  Leu  Thr  Lys  Asp  Glu  Tyr  Glu  Arg
65                       70                       75                            80

CAT  AAC  AGC  TAT  ACC  TGT  GAG  GCC  ACT  CAC  AAG  ACA  TCA  ACT  TCA  CCC              288
His  Asn  Ser  Tyr  Thr  Cys  Glu  Ala  Thr  His  Lys  Thr  Ser  Thr  Ser  Pro
                    85                       90                            95

ATT  GTC  AAG  AGC  TTC  AAC  AGG  AAT  GAG  TGT  TAG                                        321
Ile  Val  Lys  Ser  Phe  Asn  Arg  Asn  Glu  Cys
               100                      105
```

( 2 ) INFORMATION FOR SEQ ID NO:46:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

```
Ala  Asp  Ala  Ala  Pro  Thr  Val  Ser  Ile  Phe  Pro  Pro  Ser  Ser  Glu  Gln
 1                  5                        10                      15

Leu  Thr  Ser  Gly  Gly  Ala  Ser  Val  Val  Cys  Phe  Leu  Asn  Asn  Phe  Tyr
               20                       25                      30

Pro  Lys  Asp  Ile  Asn  Val  Lys  Trp  Lys  Ile  Asp  Gly  Ser  Glu  Arg  Gln
          35                       40                      45

Asn  Gly  Val  Leu  Asn  Ser  Trp  Thr  Asp  Gln  Asp  Ser  Lys  Asp  Ser  Thr
     50                       55                      60

Tyr  Ser  Met  Ser  Ser  Thr  Leu  Thr  Leu  Thr  Lys  Asp  Glu  Tyr  Glu  Arg
65                       70                       75                           80

His  Asn  Ser  Tyr  Thr  Cys  Glu  Ala  Thr  His  Lys  Thr  Ser  Thr  Ser  Pro
                    85                       90                           95

Ile  Val  Lys  Ser  Phe  Asn  Arg  Asn  Glu  Cys
               100                      105
```